US006476027B1

(12) United States Patent
Villamil et al.

(10) Patent No.: US 6,476,027 B1
(45) Date of Patent: *Nov. 5, 2002

(54) N-HYDROXY 4-SULFONYL BUTANAMIDE COMPOUNDS

(75) Inventors: Clara I. Villamil, Glenview, IL (US); John N. Freskos, Clayton, MO (US); Brent V. Mischke, Defiance, MO (US); Patrick B. Mullins, St. Louis, MO (US); Robert M. Heintz, Ballwin, MO (US); Daniel P. Getman, Chesterfield, MO (US); Joseph J. McDonald, Ballwin, MO (US); Gary A. DeCrescenzo, St. Charles, MO (US); Thomas E. Barta, Evanston; Daniel P. Becker, Glenview, both of IL (US)

(73) Assignee: Monsanto Company, St. Louis, MO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/254,531

(22) PCT Filed: Mar. 4, 1998

(86) PCT No.: PCT/US98/04297

§ 371 (c)(1),
(2), (4) Date: Dec. 6, 1999

(87) PCT Pub. No.: WO98/39316

PCT Pub. Date: Sep. 11, 1998

Related U.S. Application Data

(60) Provisional application No. 60/035,182, filed on Mar. 4, 1997.

(51) Int. Cl.[7] ................. A61K 31/16; A61K 31/4406; C07C 323/32; C07D 211/90
(52) U.S. Cl. ................. 514/237.8; 514/330; 514/331; 514/357; 514/428; 514/486; 514/575; 544/159; 546/225; 546/226; 546/233; 546/340; 548/568; 560/13; 562/621; 562/623
(58) Field of Search ................. 562/621, 623; 546/225, 226, 233, 340; 544/159; 548/568; 560/13; 514/237.8, 330, 331, 357, 428, 456, 575

(56) References Cited

U.S. PATENT DOCUMENTS 4,595,700 A    6/1986   Donald et al. ............... 514/616
6,057,369 A  * 5/2000   Groneberg et al. ......... 514/575
6,118,001 A    9/2000   Owen et al. ................. 546/229

FOREIGN PATENT DOCUMENTS

| EP | 780 386 | * 6/1997 |
|---|---|---|
| WO | WO 90/05719 | 5/1990 |
| WO | WO 93/20047 | 10/1993 |
| WO | WO 94/02466 | 2/1994 |
| WO | WO 94/24140 | 10/1994 |
| WO | WO 95/09841 | 4/1995 |
| WO | WO 95/12389 | 5/1995 |
| WO | WO 95/13289 | 5/1995 |
| WO | WO 95/29892 | 11/1995 |
| WO | WO 96/06074 | 2/1996 |
| WO | WO 96/11209 | 4/1996 |
| WO | WO 97/20824 | 6/1997 |
| WO | WO 97/24117 | 7/1997 |
| WO | WO 97/49679 | 12/1997 |
| WO | WO98/05636 | 2/1998 |

OTHER PUBLICATIONS

Groneberg et al., Chemical Abstracts, vol. 127, abstract 161589, 1997.*
Owen et al., Chemical Abstracts, vol. 128, abstract 179981, 1998.*
Salvino et al., Chemical Abstracts, vol. 132, abstract 63782, 1999.*
Schwartz et al., *Progr. Med. Chem.*, 29:271–334(1992).
Rasmussen et al., *Pharmacol. Ther.*, 75(1):69–75 (1997).
Denis et al., *Invest. New Drugs*, 15(3): 175–185 (1997).
Gearing et al. *Nature* 376, 555–557 (1994).
McGeehan et al., *Nature* 376, 558–561 (1994).
Mitchell et al., *J. Clin. Invest.*, 97:761–768 (1996).
Reboul et al., *J. Clin. Invest.*, 97:2011–2019 (1996).
*A Model of Angiogenesis in the Mouse Cornea*; Kenyon,BM, et al., Investigative Ophthalmology & Visual Science, Jul. 1996, vol. 37, No. 8.
Knight et al., FEBS Lett. 296(3):263 (1992).

* cited by examiner

*Primary Examiner*—Richard L. Raymond
(74) *Attorney, Agent, or Firm*—Harness, Dickey & Pierce, P.L.C.

(57) ABSTRACT

An N-hydroxy sulfonyl butanamide compound that inter alia inhibits matrix metalloprotease activity is disclosed as are a treatment process that comprises administering a contemplated N-hydroxy sulfonyl butanamide compound in a MMP enzyme-inhibiting effective amount to a host having a condition associated with pathological matrix metalloprotease activity.

47 Claims, No Drawings

N-HYDROXY 4-SULFONYL BUTANAMIDE COMPOUNDS

This application is a 317 of PCT/US 98/04297, filed Mar. 4, 1997 and claims priority from provisional application No. 60/035,182, filed Mar. 4, 1997.

TECHNICAL FIELD

This invention is directed to proteinase (protease) inhibitors, and more particularly to N-hydroxy sulfonyl butanamide (hydroxamic acid) compounds that, inter alia, inhibit the activity of matrix metalloproteinases, compositions of those inhibitors, intermediates for the syntheses of those compounds, processes for the preparation of the compounds and processes for treating pathological conditions associated with pathological matrix metalloproteinase activity.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals make up, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason is involved in a number of disease states. Inhibition of the enzymes responsible for a loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimer's Disease; multiple sclerosis; coronary thrombosis and bone disease. Defective injury repair processes can also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-α, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-α convertase is a metalloproteinase involved in the formation of active TNF-U. Inhibition of TNF-α convertase inhibits production of active TNF-α. Compounds that inhibit both MMPs activity have been disclosed in WIPO International Publication Nos. WO 94/24140, WO 94/02466 and WO 97/20824. There remains a need for effective MMP and TNF-α convertase inhibiting agents. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)).

MMPs are involved in other biochemical processes in mammals as well. Included is the control of ovulation, post-partum uterine involution, possibly implantation, cleavage of APP (β-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), $\alpha^2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75(1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases-and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and as yet not associated with any pathological condition. The disclosure that follows describes one family of hydroxamate MMP inhibitors that exhibit those desirable activities

BRIEF SUMMARY OF THE INVENTION

The present invention is directed to a family of molecules that among other properties inhibit matrix metalloprotease (MMP) activity, and particularly inhibit the activity of one or more of MMP-2, MMP-9, or MMP-13, while generally exhibiting little activity against MMP-1. The present invention is also directed to processes for preparing a contemplated compound and for treating a mammal having a condition associated with pathological matrix metalloprotease activity.

Briefly, one embodiment of the present invention is directed to a N-hydroxy sulfonyl butanamide (hydroxamic acid) compound that can act as a matrix metalloprotease enzyme inhibitor. That compound corresponds in structure to Formula I.

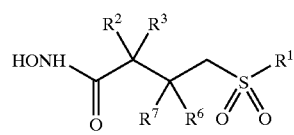

wherein $R^1$ is a substituent containing a 5- or 6-membered cyclohydrocarbyl, heterocyclo, aryl or heteroaryl radical bonded directly to the depicted $SO_2$-group and having a length greater than about the length of a fully extended hexyl group and less than about the length of a fully extended eicosyl group, said $R^1$ defining a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is equivalent to about that of one furanyl ring to about that of two phenyl rings;

$R^2$ and $R^3$ are independently selected from the group consisting of a hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfdonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl, aryl-$C_1$–$C_4$ hydrocarbyl, heteroaryl-$C_1$–$C_4$ hydrocarbyl and benzyloxy-$C_1$–$C_4$ hydrocarbyl, but only one of $R^2$ and $R^3$ is other than hydrido or $C_1$–$C_4$ hydrocarbyl; or $R^2$ and $R^3$ together with the depicted carbon atom to which they are bonded form a heterocyclic ring in which the heteroatom is oxygen, sulfur or nitrogen, said heteroatom being optionally substituted with one or two oxygens when sulfur and being substituted with a moiety $R^5$ that is selected from the group consisting of a hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl group when nitrogen; and $R^6$ and $R^7$ are independently selected from the group consisting of a hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfdonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl, aryl- $C_1$–$C_4$ hydrocarbyl, heteroaryl-$C_1$–$C_4$ hydrocarbyl and benzyloxy-$C_1$–$C_4$ hydrocarbyl, but only one of $R^6$ and $R^7$ is other than hydrido or $C_1$–$C_4$ hydrocarbyl; or $R^6$ and $R^7$ together with the depicted carbon atom to which they are bonded form a heterocyclic ring in which the heteroatom is oxygen, sulfur or nitrogen, said heteroatom being optionally substituted with one or two oxygens when sulfur and being substituted with a moiety $R^5$ that is selected from the group consisting of a hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl group when nitrogen;

only one of $R^2$, $R^3$, $R^6$ and $R^7$ is other than hydrido, $C_1$–$C_4$ hydrocarbyl or forms part of a heterocyclic ring structure as recited.

In preferred embodiments, $R^2$ is selected from the group consisting of a hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl and —Y—Z group, wherein —Y is —O or —$NR^{11}$, wherein $R^{11}$ is hydrido or $C_1$–$C_4$ hydrocarbyl, and —Z is selected from the group consisting of a hydrido, $C_1$–$C_4$ hydrocarbyl, benzoyl, (2-pyridinyl)methyl, (3-pyridinyl)methyl or (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone)ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-, 3-, or 4-pyridinyl, sulfonamido, $C_1$–$C_4$ hydrocarbylsulfonyl, $C_1$–$C_4$ hydrocarbylphosphonyl and C(O)—W wherein —W is selected from the group consisting of a hydrido, $C_1$–$C_4$ hydrocarbyl, $C_1$–$C_4$ hydrocarbyloxy —$CHR^{12}NH_2$ wherein $R^{12}$ is the side chain of a D or L amino acid, benzyloxy, benzylamino and amino group, or $R^2$ and $R^3$ together form a heterocyclic ring, and $R^6$ and $R^7$ are both either hydrido or methyl. In one of those embodiments, a contemplated compound corresponds in structure Formula II:

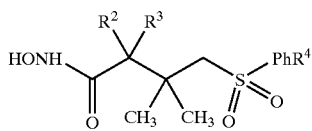

wherein

Ph is a phenyl radical bonded directly to the depicted $SO_2$-group that is itself substituted at its own 4-position with a substituent $R^4$ selected from the group consisting of one other single-ringed aryl or heteroaryl group, a $C_3$–$C_{14}$ hydrocarbyl group, a $C_2$–$C_{14}$ hydrocarbyloxy group, a phenoxy group, a thiophenoxy group, a 4-thiopyridyl group, a phenylazo group, a phenylureido group, a nicotinamido group, an isonicotinamido group, a picolinamido group, an anilino group and a benzamido group;

$R^2$ is selected from the group consisting of a hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl and —Y—Z group, wherein —Y is —O or —$NR_{11}$, wherein $R^{11}$ is hydrido or $C_1$–$C_4$ hydrocarbyl, and —Z is selected from the group consisting of a hydrido, $C_1$–$C_4$ hydrocarbyl, benzoyl, (2-pyridinyl)methyl, (3-pyridinyl)methyl or (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone)ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-, 3-, or 4-pyridinyl, sulfonamido, $C_1$–$C_4$ hydrocarbylsulfonyl, $C_1$–$C_4$ hydrocarbylphosphonyl and C(O)—W wherein —W is selected from the group consisting of a hydrido, $C_1$–$C_4$ hydrocarbyl, $C_1$–$C_4$ hydrocarbyloxy —$CHR^{12}NH_2$ wherein $R^{12}$ is the side chain of a D or L amino acid, benzyloxy, benzylamino and amino group;

$R^3$ is a hydrido or $C_1$–$C_4$ hydrocarbyl group; or $R^2$ and $R^3$ together with the depicted carbon atom to which they are bonded form a 6-membered heterocyclic ring in which the heteroatom is oxygen, sulfur or nitrogen, said heteroatom being optionally substituted with one or two oxygens when sulfur and being substituted with a moiety $R^5$ that is selected from the group consisting of a hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl group when nitrogen.

A process for treating a host mammal having a condition associated with pathological matrix metalloprotease activity is also contemplated. That process comprises administering a compound described hereinbefore in an enzyme-inhibiting effective amount to a mammalian host having such a condition. The use of repeated administrations is particularly contemplated.

Among the several benefits and advantages of the present invention are the provision of compounds and compositions effective as inhibitors of matrix metalloproteinase activity, and the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis, multiple sclerosis and bone disease.

An advantage of the invention is the provision of a method for preparing such compositions. Another benefit is the provision of a method for treating a pathological condition associated with abnormal matrix metalloproteinase activity.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Still further benefits and advantages of the invention will be apparent to the skilled worker from the disclosure that follows.

DETAILED DESCRIPTION OF PREFERRED EMBODIMENTS

In accordance with the present invention, it has been found that certain N-hydroxy sulfonyl butanamide (hydroxamic acid) compounds, also referred to herein as sulfonyl butanhydroxamate compounds, are effective, inter alia, for inhibition of matrix metalloproteinases ("MMPs") believed to be associated with uncontrolled or otherwise pathological breakdown of connective tissue. In particular, it has been found that these certain sulfonyl butanhydroxamate compounds are effective for inhibition of collagenase III (MMP-13) and also gelatinase A (MMP-2), which can be particularly destructive to tissue if present or generated in abnormal quantities or concentrations, and thus exhibit a pathological activity.

Moreover, it has been discovered that many of these sulfonyl butanhydroxamate compounds are selective in the inhibition of MMPs associated with diseased conditions without excessive inhibition of other collagenases essential to normal bodily function such as tissue turnover and repair. More particularly, it has been found that particularly preferred the sulfonyl butanhydroxamate compounds are particularly active in inhibiting of MMP-13 and/or MMP-2, while having a limited or minimal effect on MMP-1. This point is discussed in detail hereinafter and is illustrated in the Inhibition Table hereinafter.

One embodiment of the present invention is directed to a sulfonyl butanhydroxamate compound that can act as a matrix metalloprotease enzyme inhibitor. That compound corresponds in structure to Formula I

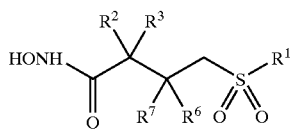

wherein
R$^1$ is a substituent containing a 5- or 6-membered cyclohydrocarbyl, heterocyclo, aryl or heteroaryl radical bonded directly to the depicted SO$_2$-group and having a length that is equivalent to a length that is greater than about that of a fully extended hexyl group and less than about that of a fully extended eicosyl group. In addition, R$^1$ defines a three-dimensional volume, when rotated about an axis drawn through the SO$_2$-bonded 1-position and the 4-position of a 6-membered ring radical or drawn through the SO$_2$-bonded 1-position and the center of 3,4-bond of a 5-membered ring radical, whose widest dimension in a direction transverse to the axis of rotation is equivalent to about that of one furanyl ring to about that of two phenyl rings;

R$^2$ and R$^3$ are independently selected from the group consisting of a hydrido, C$_1$–C$_4$ hydrocarbyl, heteroaryl-C$_1$–C$_4$ hydrocarbyl, aryl-C$_1$–C$_4$ hydrocarbyl, hydroxy-C$_1$–C$_4$ hydrocarbyl, C$_1$–C$_4$ hydrocarbyloxy-C$_1$–C$_4$ hydrocarbyl, aryloxy-C$_1$–C$_4$ hydrocarbyl, amino-C$_1$–C$_4$ hydrocarbyl, C$_1$–C$_4$ hydrocarbylthio-C$_1$–C$_4$ hydrocarbyl, C$_1$–C$_4$ hydrocarbylsulfdonyl-C$_1$–C$_4$ hydrocarbyl, aminosulfonylamino-C$_1$–C$_4$ hydrocarbyl, aminocarbonylamino-C$_1$–C$_4$ hydrocarbyl, C$_1$–C$_4$ hydrocarbylcarbonylamino-C$_1$–C$_4$ hydrocarbyl, aryl-C$_1$–C$_4$ hydrocarbyl, heteroaryl-C$_1$–C$_4$ hydrocarbyl and benzyloxy-C$_1$–C$_4$ hydrocarbyl, but only one of R$^2$ and R$^3$ is other than hydrido or C$_1$–C$_4$ hydrocarbyl; or R$^2$ and R$^3$ together with the depicted carbon atom to which they are bonded form a heterocyclic ring in which the heteroatom is oxygen, sulfur or nitrogen, said heteroatom being optionally substituted with one or two oxygens when sulfur and being substituted with a moiety R$^5$ that is selected from the group consisting of a hydrido, C$_1$–C$_4$ hydrocarbyl, C$_3$–C$_6$ cyclohydrocarbyl, C$_1$–C$_4$ carbonylhydrocarbyl, and sulfonyl C$_1$–C$_4$ hydrocarbyl group when nitrogen; and R$^6$ and R$^7$ are independently selected from the group consisting of a hydrido, C$_1$–C$_4$ hydrocarbyl, heteroaryl-C$_1$–C$_4$ hydrocarbyl, aryl-C$_1$–C$_4$ hydrocarbyl, hydroxy-C$_1$–C$_4$ hydrocarbyl, C$_1$–C$_4$ hydrocarbyloxy-C$_1$–C$_4$ hydrocarbyl, aryloxy-C$_1$–C$_4$ hydrocarbyl, amino-C$_1$–C$_4$ hydrocarbyl, C$_1$–C$_4$ hydrocarbylthio-C$_1$–C$_4$ hydrocarbyl, C$_1$–C$_4$ hydrocarbylsulfdonyl-C$_1$–C$_4$ hydrocarbyl, aminosulfonylamino-C$_1$–C$_4$ hydrocarbyl, aminocarbonylamino-C$_1$–C$_4$ hydrocarbyl, C$_1$–C$_4$ hydrocarbylcarbonylamino-C$_1$–C$_4$ hydrocarbyl, aryl-C$_1$–C$_4$ hydrocarbyl, heteroaryl-C$_1$–C$_4$ hydrocarbyl and benzyloxy-C$_1$–C$_4$ hydrocarbyl, but only one of R$^6$ and R$^7$ is other than hydrido or C$_1$–C$_4$ hydrocarbyl; or R$^6$ and R$^7$ together with the depicted carbon atom to which they are bonded form a heterocyclic ring in which the heteroatom is oxygen, sulfur or nitrogen, said heteroatom being optionally substituted with one or two oxygens when sulfur and being substituted with a moiety R$^5$ that is selected from the group consisting of a hydrido, C$_1$–C$_4$ hydrocarbyl, C$_3$–C$_6$ cyclohydrocarbyl, C$_1$–C$_4$ carbonylhydrocarbyl, and sulfonyl C$_1$–C$_4$ hydrocarbyl group when nitrogen;

only one of R$^2$, R$^3$, R$^6$ and R$^7$ is other than hydrido, C$_1$–C$_4$ hydrocarbyl or forms part of a heterocyclic ring structure as recited.

As noted above, an R$^1$ substituent contains a 5- or 6-membered cyclohydrocarbyl, heterocyclo, aryl or heteroaryl radical bonded directly to the depicted SO$_2$-group. An R$^1$ substituent also has length, width and substitution requirements that are discussed in detail below. It is noted here, however, that a single-ringed or fused ring cyclohydrocarbyl, heterocyclo, aryl or heteroaryl radical is not itself long enough to fulfill the length requirement. As such, that cyclohydrocarbyl, heterocyclo, aryl or heteroaryl radical must itself be substituted.

Exemplary 5- or 6-membered cyclohydrocarbyl, heterocyclo, aryl or heteroaryl radicals that can constitute a portion of a R$^1$ substituent and are themselves substituted as discussed herein include phenyl, 2-, 3-, or 4-pyridyl, 2-naththyl, 2-pyrazinyl, 2- or 5-pyrimidinyl, 2- or 3-benzo(b)thienyl, 8-purinyl, 2- or 3-furyl, 2- or 3-pyrrolyl, 2-imidazolyl, cyclopentyl, cyclohexyl, 2- or 3-piperidinyl, 2- or 3-morpholinyl, 2- or 3-tetrahydropyranyl, 2-imidazolidinyl, 2- or 3-pyrazolidinyl and the like. A phenyl radical is particularly preferred and is used illustratively herein.

When examined along its longest chain of atoms, an R$^1$ substituent, including its own substituent when present, has a total length equivalent to a length that is greater than that of a fully extended saturated chain of six carbon atoms (a hexyl group); i.e., a length of a fully extended heptyl chain or longer, and a length that is less than that of a fully extended saturated chain of about 20 carbons (an eicosyl group). Preferably, that length is equivalent to a length of a fully extended saturated chain of about 8 to about 18 carbon atoms, even though many more atoms may be present in ring structures or substituents. This length requirement is discussed further below.

Looked at more generally, and aside from specific moieties from which it is constructed, an R$^1$ substituent (radical, group or moiety) has a length equivalent to that of a fully extended heptyl group or greater. Such an R$^1$ substituent also has a length that is less than that of a fully extended eicosyl group. That is to say that a $R^1$ is a substituent having a length greater than that of a saturated six carbon chain and shorter than that of a saturated twenty carbon chain, and more preferably, a length greater than that of a octyl group and less than that of a palmityl group. The radical chain lengths are measured along the longest linear atom chain in the radical, following the skeletal atoms of a ring where necessary. Each atom in the chain, e.g. carbon, oxygen or nitrogen, is presumed to be carbon for ease in calculation.

Such lengths can be readily determined by using published bond angles, bond lengths and atomic radii, as needed, to draw and measure a chain, or by building models using commercially available kits whose bond angles, lengths and atomic radii are in accord with accepted, published values. Radical (substituent) lengths can also be determined somewhat less exactly by presuming, as is done here, that all atoms have bond lengths of saturated carbon, that unsaturated and aromatic bonds have the same lengths as saturated bonds and that bond angles for unsaturated bonds are the same as those for saturated bonds, although the above-mentioned modes of measurement are preferred. For example, a 4-phenyl or 4-pyridyl group has a length of a four carbon chain, as does a propoxy group, whereas a biphenyl group has a length of about an eight carbon chain using a contemplated measurement mode.

In addition, an $R^1$ substituent, when rotated about an axis drawn through the $SO_2$-bonded 1-position and the 4-position of a 6-membered ring radical or the $SO_2$-bonded 1-position and through the 3,4 bond of a 5-membered ring radical defines a three-dimensional volume whose widest dimension has the width equivalent to that of about one furanyl ring to about the width of two phenyl rings in a direction transverse to that axis to rotation.

When utilizing this width or volume criterion, a fused ring system such as a naphthyl or purinyl radical is considered to be a 6- or 5-membered ring that is substituted at appropriate positions numbered from the $SO_2$-linkage that is deemed to be at the 1-position as discussed before. Thus, a 2-naphthyl substituent or an 8-purinyl substituent is an appropriately sized $R^1$ radical as to width when examined using the above rotational width criterion. On the other hand, a 1-naphthyl group or a 7- or 9-purinyl group is too large upon rotation and is excluded.

As a consequence of these length and width requirements, $R^1$ substituents such as 4-(phenyl)phenyl [biphenyl], 4-(4'-methoxyphenyl)phenyl, 4-(phenoxy)phenyl, 4-(thiophenyl)phenyl [4-(phenylthio)phenyl], 4-(phenylazo)phenyl 4-(phenylureido)phenyl, 4-(anilino)phenyl, 4-(nicotinamido)phenyl, 4-(isonicotinamido)phenyl, 4-(picolinamido)phenyl and 4-(benzamido)phenyl are among particularly preferred $R^1$ substituents, with 4-(phenoxy)phenyl and 4-(thiophenyl)phenyl being most preferred.

An $SO_2$-linked cyclohydrocarbyl, heterocyclo, aryl or heteroaryl radical is a 5- or 6-membered single-ring that is itself substituted with one other substituent, $R^4$. The $SO_2$-linked single-ringed cyclohydrocarbyl, heterocyclo, aryl or heteroaryl radical is $R^4$-substituted at its own 4-position when a 6-membered ring and at its own 3-position when a 5-membered ring. The cyclohydrocarbyl, heterocyclo, aryl or heteroaryl radical to which $R^4$ is bonded is preferably a phenyl group, so that $R^1$ is preferably $PhR^4$ in which $R^4$ is bonded at the 4-position of the $SO_2$-linked phenyl (Ph) radical, and in which $R^4$ can itself be optionally substituted as is discussed hereinafter. Substitution at the 2-position of a $SO_2$-linked cyclohydrocarbyl, heterocyclo, aryl or heteroaryl .radical appears to greatly lessen inhibitory potency toward MMP enzymes, and is absent from a contemplated compound.

A contemplated $R^4$ substituent can be a single-ringed cyclohydrocarbyl, heterocyclo, aryl or heteroaryl group or another substituent having a chain length of 3 to about 14 carbon atoms such as a hydrocarbyl or hydrocarbyloxy group [e.g., $C_3$–$C_{14}$ hydrocarbyl or O-$C_2$–$C_{14}$ hydrocarbyl], a phenyl group, a phenoxy group [—$OC_6H_5$], a thiophenoxy group [phenylsulfanyl; —$SC_6H_5$], an anilino group [—$NHC_6H_5$], a phenylazo group [—$N_2C_6H_5$], a phenylureido group [aniline carbonylamino; —NHC(O)NH—$C_6H_5$], a benzamido group [—NHC(O)$C_6H_5$], a nicotinamido group [3-NHC(O)$C_5H_4N$], an isonicotinamido group [4-NHC(O)$C_5H_4N$], or a picolinamido group [2-NHC(O)$C_5H_4N$]. As noted before in conjunction with the discussion of $R^1$, most preferred $R^4$ substituents are phenoxy and thiophenoxy groups that are preferably themselves free of substitution. Additionally contemplated $R^4$ substituent groups include a heterocyclo, heterocyclohydrocarbyl, arylhydrocarbyl, arylheterocyclohydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and a heteroarylthio group.

A contemplated $R^4$ substituent can itself also be substituted with one or more substituent radicals at the meta- or para-position or both of a six-membered ring with a single atom or a substituent containing a longest chain of up to ten atoms, excluding hydrogen. Exemplary substituent radicals include a halo, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonyl-hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxy-carbonylhydrocarbyl, hydrocarbylhydroxycarbonyl-hydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbyl-sulfonylamino, cyclohydrocarbylsulfonylamino, heterocyclohydrocarbylsulfonylamino and N-monosubstituted or N,N-disubstituted aminohydrocarbyl group wherein the substituent(s) on the nitrogen are selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or wherein the nitrogen and two substituents attached thereto form a 5- to 8-membered heterocyclic or heteroaryl ring group.

Thus, initial studies indicate that so long as the length, substitution and width (volume upon rotation) requirements of an $SO_2$-linked $R^1$ substituent discussed herein are met, an $R^1$ substituent can be extremely varied.

A particularly preferred $R^4$ substituent of an $SO_2$-linked Ph group is a single-ringed aryl or heteroaryl, phenoxy, thiophenoxy, phenylazo, phenylureido, nicotinamido, isonicotinamido, picolinamido, anilino or benzamido group that is unsubstituted or is itself substituted (optionally substituted) at the para-position when a 6-membered ring or the 3-position when a 5-membered ring. Here, single atoms such as halogen moieties or substituents that contain one to a chain of about ten atoms other than hydrogen such as $C_1$–$C_{10}$ hydrocarbyl, $C_1$–$C_9$ hydrocarbyloxy or carboxyethyl groups can be used.

Exemplary particularly preferred substituted $PhR^4$ (particularly preferred substituted $R^1$) substituents include biphenyl, 4-phenoxyphenyl, 4-thiophenoxyphenyl, 4-benzamidophenyl, 4-phenylureido, 4-anilinophenyl, 4-nicotinamido, 4-isonicotinamido, and 4-picolinamido. Exemplary particularly preferred $R^4$ groups contain a 6-membered aromatic ring and include a phenyl group, a phenoxy group, a thiophenoxy group, a phenylazo group, a phenylureido group, an anilino group, a nicotinamido group, an isonicotinamido group, a picolinamido group and a benzamido group.

More specifically, a particularly preferred sulfonyl butanhydroxamate compounds has an $R^4$ substituent that is a phenyl group, a phenoxy group, a thiophenoxy group, a phenylazo group, a phenylureido group, an anilino group, a nicotinamido group, an isonicotinamido group, a picolinamido group or a benzamido group that is itself optionally substituted at its own meta or para-position or both with a moiety that is selected from the group consisting of a halogen, a $C_1$–$C_9$ hydrocarbyloxy (—O—$C_1$–$C_9$ hydrocarbyl) group, a $C_1$–$C_{10}$ hydrocarbyl group, a di-$C_1$–$C_9$ hydrocarbylamino [—N($C_1$–$C_9$ hydrocarbyl)($C_1$–$C_9$ hydrocarbyl)] group, a carboxyl $C_1$–$C_8$ hydrocarbyl ($C_1$–$C_8$ hydrocarbyl-$CO_2$H) group, a $C_1$–$C_4$ hydrocarbyloxycarbonyl $C_1$–$C_4$ hydrocarbyl [$C_1$–$C_4$ hydrocarbyl-O—(CO)—$C_1$–$C_4$ hydrocarbyl] group, a $C_1$–$C_4$ hydrocarbyloxycarbonyl $C_1$–$C_4$ hydrocarbyl [$C_1$–$C_4$ hydrocarbyl (CO)—O—$C_1$–$C_4$ hydrocarbyl] group and a $C_1$–$C_8$ hydrocarbyl carboxamido [—NH(CO)-$C_1$–$C_8$ hydrocarbyl] group, or is substituted at the meta- and para-positions by two methyl groups or by a $C_1$–$C_2$ alkylenedioxy group such as a methylenedioxy group.

Inasmuch as a contemplated $SO_2$-linked cyclohydrocarbyl, heterocyclo, aryl or heteroaryl radical is itself preferably substituted with a 6-membered aromatic ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked cyclohydrocarbyl, heterocyclo, aryl or heteroaryl radical. When a $R^4$ substituent is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked cyclohydrocarbyl, heterocyclo, aryl or heteroaryl radical is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

$R^2$ and $R^3$ are independently selected from the group consisting of a hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl and benzyloxy-$C_1$–$C_4$ hydrocarbyl. However, only one of $R^2$ and $R^3$ is other than hydrido or $C_1$–$C_4$ hydrocarbyl, with hydrido being the preferred substituent.

Alternatively, $R^2$ and $R^3$ together with the depicted carbon atom to which they are bonded form a heterocyclic ring, preferably a six-membered ring, in which the heteroatom is oxygen, sulfur or nitrogen. That heteroatom is optionally substituted with one or two oxygens when sulfur and is substituted with a moiety $R^5$ that is selected from the group consisting of a hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl group when nitrogen.

$R^6$ and $R^7$ are independently selected from the group consisting of a hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfdonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl and benzyloxy-$C_1$–$C_4$ hydrocarbyl. Again, only one of $R^6$ and $R^7$ is other than hydrido or $C_1$–$C_4$ hydrocarbyl, with both substituents preferably being either hydrido or methyl.

Alternatively, $R^6$ and $R^7$ together with the depicted carbon atom to which they are bonded form a heterocyclic ring in which the heteroatom is oxygen, sulfur or nitrogen. That heteroatom is optionally substituted with one or two oxygens when sulfur and is substituted with a moiety $R^5$ that is selected from the group consisting of a hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl group when nitrogen.

Preferred $R^6$ and $R^7$ substituents and heterocyclic rings are the same as those noted above for $R^2$ and $R^3$, and therefore will not be repeated here.

It is to be noted that only one of $R^2$, $R^3$, $R^6$ and $R^7$ is other than hydrido, $C_1$–$C_4$ hydrocarbyl or forms part of a heterocyclic ring structure as recited. Thus, the presence of two substituents on two adjacent carbon atoms other than hydrido or $C_1$–$C_4$ hydrocarbyl is not contemplated, nor is the presence of two heterocyclic rings on adjacent carbons.

In preferred embodiments, $R^6$ and $R^7$ are preferably both either hydrido or methyl.

In one particularly preferred embodiment, a contemplated compound corresponds in structure to Formula II, wherein preferred $R^2$ and $R^3$ substituents are as defined below, and $R^1$ is $PhR^4$ wherein Ph is phenyl substituted at the 4-position with substituent $R^4$ that is defined hereinabove. It is noted that preferred $R^2$ and $R^3$ substituents need not be present only when $R^1$ is $PhR^4$, and can be present with any $R^1$ substituent.

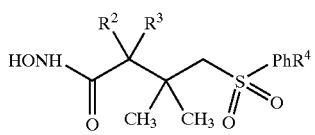

In preferred embodiments, an $R^2$ substituent is selected from the group consisting of a hydrido, $C_1$–$C_4$ hydrocarbyl, N-piperidinyl, N-piperazinyl, N-($C_1$–$C_4$ hydrocarbyl) piperazinyl, N-pyrrolidinyl, N-morpholinyl and a —Y—Z group, wherein —Y is —O or —$NR^{11}$, $R^{11}$ is hydrido or $C_1$–$C_4$ hydrocarbyl, and —Z is selected from the group consisting of a hydrido, $C_1$–$C_4$ hydrocarbyl, benzoyl, (2-pyridinyl)methyl, (3-pyridinyl)methyl or (4-pyridinyl) methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone)ethyl, 2-(succinimidyl)ethyl, 2-(hydantoinyl), 2-(3-methylhydantoinyl)ethyl, 2-(N-$C_1$–$C_4$ hydrocarbylamino) ethyl, 2-[N,N-di($C_1$–$C_4$ hydrocarbyl)amino]ethyl, carboxy $C_1$–$C_4$ hydrocarbyl, piperidinyl, 2-, 3-, or 4-pyridinyl, sulfonamido, $C_1$–$C_4$ hydrocarbylsulfonyl, $C_1$–$C_4$ hydrocarbylphosphonyl and C(O)—W wherein —W is selected from the group consisting of a hydrido, $C_1$–$C_4$ hydrocarbyl, $C_1$–$C_4$ hydrocarbyloxy —$CHR^{12}NH_2$ wherein $R^{12}$ is the side chain of a D or L amino acid, benzyloxy, benzylamino and amino group. Thus, where —Y is —O and —Z is hydrido, $R^2$ (—Y—Z) is hydroxyl. Similarly, where —Y is NH and —Z is hydrido, $R^2$ is amino (—$NH_2$).

Exemplary amino acid side chains are those of the naturally occurring L amino acids that can be present in D or L configuration or a mixture thereof. The side chains of the so-called modified and unusual amino acids listed in 37 C.F.R § 1.822 are also contemplated here, and those side chains can be present in a D or L configuration or as a mixture.

Preferably, $R^3$ is a hydrido or $C_1$–$C_4$ hydrocarbyl group. More preferably, $R^3$ is hydrido.

Alternatively, $R^2$ and $R^3$ together with the depicted carbon atom to which they are bonded form a 6-membered heterocyclic ring in which the heteroatom is oxygen, sulfur or nitrogen. That heteroatom can be optionally substituted with one or two oxygens when sulfur and can be optionally substituted with a moiety, $R^5$, selected from the group consisting of a $C_1$–$C_4$ hydrocarbyl, $C_3$–$C_6$ cyclohydrocarbyl such as cyclopropyl, cyclobutyl, cyclopentenyl and cyclohexenyl, $C_1$–$C_4$ carbonylhydrocarbyl such as formyl, acetyl, acryloyl, and butyryl, and sulfonyl $C_1$–$C_4$ hydrocarbyl group such as methylsulfonyl, ethylsulfonyl and the like when nitrogen. Thus, $R^2$ and $R^3$ together with their jointly-bonded carbon atom can form a 4-tetrahydrothiopyranyl group, its corresponding sulfoxide or sulfone, a 4-piperidinyl or a 4-tetrahydropyranyl group. When present, the 4-piperidinyl group can be N-substituted with an above-described $R^5$ substituent.

When $R^3$ is hydrido, as is more preferred, particularly preferred $R^2$ groups include amino, hydroxyl, 2-, 3- and 4-pyridylmethyl, N-pyrrolidinylmethyl and N-piperidinyl. Where $R^2$ and $R^3$ together with their jointly-bonded carbon atom form a six-membered heterocyclic ring, that heteroatom is preferably nitrogen that is optionally substituted as discussed before.

The length of an $R^1$ substituent bonded to the $SO_2$ group is believed to play a role in the overall activity of a contemplated inhibitor compound against MMP enzymes generally. Thus, a compound having an $R^1$ substituent that is shorter in length than a heptyl group, e.g., a 4-methoxyphenyl group (compound of Example 6), typically exhibits moderate to poor inhibitory activity against all of the MMP enzymes, whereas compounds whose $R^1$ substituents have a length of about an heptyl chain or longer, e.g., a 4-phenoxyphenyl group (compound of Example 5) that has a length of about a nine-carbon chain, typically exhibit good to excellent potencies against MMP-13 or MMP-2 and also selectivity against MMP-1. Exemplary data are provided in the Inhibition Table hereinafter in which the activities of the above two compounds can be compared.

The data of that Table also illustrate that compounds having an $R^3$ group that is hydrido and a nitrogen-containing $R^2$ substituent are particularly effective inhibitors of the activity of MMP-2, while maintaining minimal activity against MMP-1.

In view of the above-discussed preferences, compounds corresponding in structure to particular formulas constitute particularly preferred embodiments.

In one of those embodiments, a contemplated compound corresponds in structure to Formula II, below, wherein preferred $R^2$, $R^3$ substituents and $PhR^4$ are as defined above.

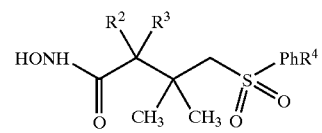

A compound of Formula II is preferably present in the stereoconfiguration of Formula IIA, below

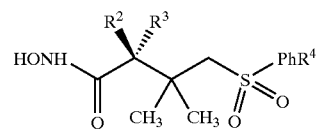

In yet another group of preferred compounds, $R^2$ and $R^3$ together with the carbon atom to which they are bonded form a six-membered heterocyclic ring whose heteroatom, X, is O, S, S(O), S(O$_2$) or $NR^5$, e.g., a 4-piperidinyl, tetrahydropyranyl or tetrahydrothiopyranyl group. The nitrogen of the 4-piperidinyl group is substituted with a moiety $R^5$ selected from the group consisting of a hydrido, $C_1$–$C_4$ hydrocarbyl, $C_3$–$C_6$ cyclohydrocarbyl, $C_1$–$C_4$ carbonylhydrocarbyl, and a sulfonyl $C_1$–$C_4$ hydrocarbyl group. The $R^6$ and $R^7$ substituents here are both a hydrido or $C_1$–$C_4$ hydrocarbyl group, preferably methyl. Those preferred compounds correspond in structure generally and specifically to Formulas III and IV, respectively

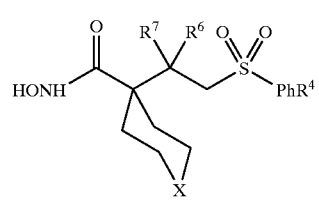

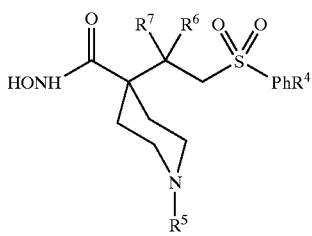

Following the preference that each of $R^6$ and $R^7$ be methyl, and the preference that $R^1$ be $PhR^4$, which in turn is phenpoxyphenyl or 4-thiophenoxyphenyl, another particularly preferred compound corresponds in structure to Formula V, below

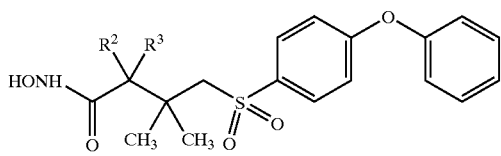

The preferred stereoconfiguration of a compound of Formula V is illustrated in Formula VA, below

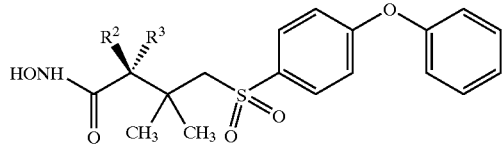

Taking in to consideration the further preference that $R^3$ be a hydrido group, a presently most preferred compound corresponds in stereoconfiguration to Formula VI, below

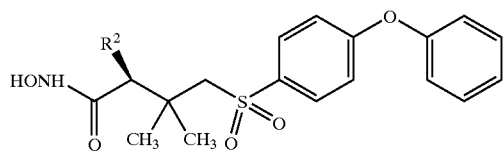

In another of those embodiments in which the preference for $R^6$ and $R^7$ both being hydrido, a contemplated compound corresponds in structure to Formula VII, below, wherein $R^2$, $R^3$ and $PhR^4$ are as defined above.

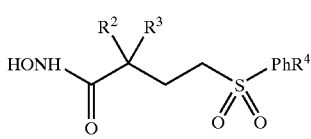

A above compound of this embodiment preferably has the stereoconfiguration shown in Formula VIIA, below

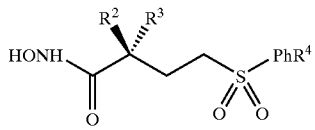

In a further group of preferred compounds of this embodiment, $R^2$ and $R^3$ together with the carbon atom to which they are bonded form a six-membered heterocyclic ring whose heteroatom, X, is O, S, S(O), S(O$_2$) or $NR^5$, e.g., a 4-piperidinyl, tetrahydropyranyl or tetrahydrothiopyranyl group. The nitrogen atom of the 4-piperidinyl group is substituted with a moiety $R^5$ selected from the group consisting of a hydrido, $C_1$–$C_4$ hydrocarbyl, $C_3$–$C_6$ cyclohydrocarbyl, $C_1$–$C_4$ carbonylhydrocarbyl, and a sulfonyl $C_1$–$C_4$ hydrocarbyl group. Those preferred compounds correspond in structure generally and specifically to Formulas VIII and IX, respectively, below

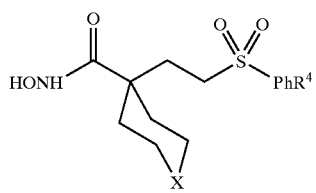

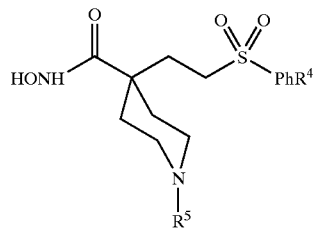

The word "hydrocarbyl" is used herein as a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., $C_1$–$C_4$ alkyl, methyl or dodecenyl. Exemplary hydrocarbyl groups contain a chain of 1 to about 12 carbon atoms, and preferably one to about 10 carbon atoms.

A particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a carbonyl group is referred to as a hydrocarboyl group inasmuch as there is no ambiguity in using that suffix. As a skilled worker will understand, a substituent that cannot exist such as a $C_1$ alkenyl group is not intended to be encompassed by the word "hydrocarbyl".

The term "carbonyl", alone or in combination, means a —C(=O)— group wherein the remaining two bonds (valences) are independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —$NH_2$ group, whereas the term mono-substituted amino, alone or in combination, means a substituted amine —N(H)(substituent) group wherein one hydrogen atom is replaced with a substituent, and disubstituted amine means a —N(substituent)2 wherein two hydrogen atoms of the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—N+ (substituent)$_4$) that is positively charged and accompanied by a counter ion or N-oxide means one substituent is oxygen and the group is represented as (—N+ (substituent)$_3$—$O^{31}$); i.e., the charges are internally compensated.

The term "cyano", alone or in combination, means a —C-triple bond-N (—CN) group. The term "azido", alone or in combination, means a —N-double bond-N-double bond-N— (—N=N=N—) group.

The term "hydroxyl", alone or in combination, means a —OH group. The term "nitro", alone or in combination, means a —$NO_2$ group.

The term "azo", alone or in combination, means a —N=N— group wherein the bonds at the terminal positions are independently substituted. The term "hydrazino", alone or in combination, means a —NH-NH— group wherein the remaining two bonds (valences) are independently substituted. The hydrogen atoms of the hydrazino group can be replaced, independently, with substituents and the nitrogen atoms can form acid addition salts or be quaternized.

The term "sulfonyl", alone or in combination, means a —S(O)$_2$— group wherein the remaining two bonds (valences) can be independently substituted. The term "sulfoxido", alone or in combination, means a —S(=O)$_1$— group wherein the remaining two bonds (valences) can be independently substituted. The term "sulfonylamide", alone or in combination, means a —S(=O)$_2$—N= group wherein the remaining three bonds (valences) are independently substituted. The term "sulfinamido", alone or in combination, means a —S(=O)$_1$N= group wherein the remaining three bonds (valences) are independently substituted. The term "sulfenamide", alone or in combination, means a —S—N= group wherein the remaining three bonds (valences) are independently substituted.

The term "hydrocarbyloxy", alone or in combination, means an hydrocarbyl ether radical wherein the term hydrocarbyl is as defined above. Examples of suitable hydrocarbyl ether radicals include methoxy, ethoxy, n-propoxy, isopropoxy, allyloxy, n-butoxy, iso-butoxy, sec-butoxy, tert-butoxy and the like. The term "cyclohydrocarbyl", alone or in combination, means a hydrocarbyl radical that contains 3 to about 8 carbon atoms, preferably from about 3 to about 6 carbon atoms, and is cyclic. The term "cyclohydrocarbylhydrocarbyl" means an hydrocarbyl radical as defined above which is substituted by a cyclohydrocarbyl as also defined above. Examples of such cyclohydrocarbylhydrocarbyl radicals include cyclopropyl, cyclobutyl, cyclopentenyl, cyclohexyl cyclooctynyl and the like.

The term "aryl", alone or in combination, means a phenyl or naphthyl radical that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means an hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O— arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

The terms "hydrocarbyloyl" or "hydrocarbylcarbonyl", alone or in combination, mean an acyl radical derived from an hydrocarbylcarboxylic acid, examples of which include acetyl, propionyl, acryloyl, butyryl, valeryl, 4-methylvaleryl, and the like. The term "cyclohydrocarbylcarbonyl" means an acyl group derived from a monocyclic or bridged cyclohydrocarbylcarboxylic acid such as cyclopropanecarbonyl, cyclohexenecarbonyl, adamantanecarbonyl, and the like, or from a benz-fused monocyclic cyclohydrocarbylcarboxylic acid that is optionally substituted by, for example, a hydrocarbyloylamino group, such as 1,2,3,4-tetrahydro-2-naphthoyl, 2-acetamido-1,2,3,4-tetrahydro-2-naphthoyl. The terms "arylhydrocarbyloyl" or "arylhydrocarbylcarbonyl" mean an acyl radical derived from an aryl-substituted hydrocarbylcarboxylic acid such as phenylacetyl, 3-phenylpropenyl (cinnamoyl), 4-phenylbutyryl, (2-naphthyl)acetyl, 4-chlorohydrocinnamoyl, 4-aminocinnamoyl, 4-methoxycinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocyclohydrocarbyl portion of a heterocyclylcarbonyl, heterocyclyloxycarbonyl, heterocyclylhydrocarbyloxycarbonyl, or heterocyclohydrocarbyl group or the like is a saturated or partially unsaturated monocyclic, bicyclic or tricyclic heterocycle that contains one to four hetero atoms selected from nitrogen, oxygen and sulphur, which is optionally substituted on one or more carbon atoms by a halogen, alkyl, alkoxy, oxo group, and the like, and/or on a secondary nitrogen atom (i.e., —NH—) by an hydrocarbyl, arylhydrocarbyloxycarbonyl, hydrocarbyloyl, aryl or arylhydrocarbyl or on a tertiary nitrogen atom (i.e. =N—) by oxido and that is attached via a carbon atom. The tertiary nitrogen atom with three substituents can also form a N-oxide [=N(O)—] group. Examples of such heterocyclyl groups are pyrrolidinyl, piperidinyl, piperazinyl, morpholinyl, thiamorpholinyl, and the like.

The heteroaryl portion of a heteroaroyl, heteroaryloxycarbonyl, or a heteroarylhydrocarbyloyl (heteroarylhydrocarbyl carbonyl) group or the like is an aromatic monocyclic, bicyclic, or tricyclic heterocycle that contains the hetero atoms and is optionally substituted as defined above with respect to the definition of heterocyclyl. A "heteroaryl" group is an aromatic heterocyclic ring substituent that can contain one, two, three or four atoms in the ring that are other than carbon. Those heteroatoms can be nitrogen, sulfur or oxygen. A heteroaryl group can contain a single five- or 6-membered ring or a fused ring system that contains two 6-membered rings or a five- and a 6-membered ring. Exemplary heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups ; six/5-membered fused ring substituents such as benzothiofuranyl, isobenzothiofuranyl, benzisoxazolyl, benzoxazolyl, purinyl and anthranilyl groups ; and six/6-membered fused rings such as 1,2-,.1,4-,.2,3- and 2,1-benzopyronyl, quinolinyl, isoquinolinyl, cinnolinyl, quinazolinyl, and 1,4-benzoxazinyl groups.

The term "cyclohydrocarbylhydrocarbyloxy-carbonyl" means an acyl group derived from a cyclohydrocarbylhydrocarbyloxycarboxylic acid of the formula cyclohydrocarbylhydrocarbyl-O—COOH wherein cyclohydrocarbylhydrocarbylhas the significance given above. The term "aryloxyhydrocarbyloyl" means an acyl radical of the formula aryl-O—hydrocarbyloyl wherein aryl and hydrocarbyloyl have the significance given above. The term "heterocyclyloxycarbonyl" means an acyl group derived from heterocyclyl-O—COOH wherein heterocyclyl is as defined above. The term "heterocyclylhydrocarbyloyl" is an acyl radical derived from a heterocyclyl-substituted hydrocarbylcarboxylic acid wherein heterocyclyl has the significance given above. The term "heterocyclylhydrocarbyloxycarbonyl" means an acyl radical derived from a heterocyclyl-substituted hydrocarbyl-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, hydrocarbyl, aryl, aralkyl, cyclohydrocarbyl, cyclohydrocarbylhydrocarbyl radicals and the like. The term "aminohydrocarbyloyl" means an acyl group derived from an amino-substituted hydrocarbylcarboxylic acid wherein the amino group can be a primary, secondary or tertiary amino group containing substituents independently selected from hydrogen, alkyl, aryl, aralkyl, cyclohydrocarbyl, cyclohydrocarbylhydrocarbyl radicals and the like.

The term "halogen" means fluorine, chlorine, bromine or iodine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1,1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl.

Table 1 through Table 37, below, show several contemplated N-hydroxy sulfonyl butanamide compounds as structural formulas that illustrate substituent groups. Each group of compounds is illustrated by a generic formula, followed by a series of preferred moieties or groups that constitute various substituents that can be attached at the position clearly shown in the generic structure. The substituent symbols, e.g., $R^1$, are as shown in each Table. One bond (straight line) is shown with those substituents to indicate the respective positions of attachment in the illustrated compound. This system is well known in the chemical communication arts and is widely used in scientific papers and presentations.

TABLE 1

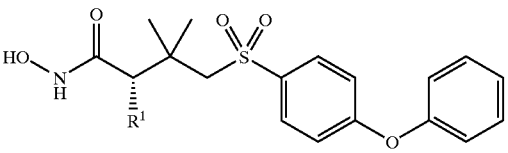

| Example | -$R^1$ |
|---|---|
| 1 | 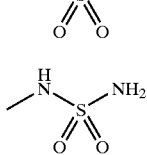 |
| 2 | 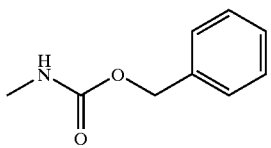 |
| 3 | 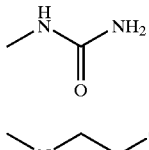 |
| 4 | 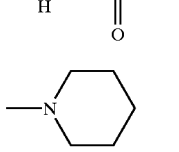 |
| 5 |  |
| 6 | —N⟨piperidinyl⟩ |

TABLE 1-continued
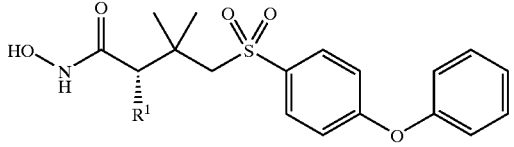
| Example | -R¹ |
|---|---|
| 7 | 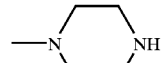 |
| 8 | 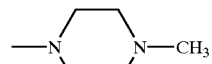 |
| 9 | 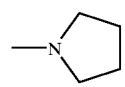 |
| 10 | 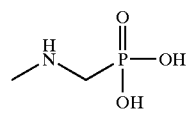 |
TABLE 2
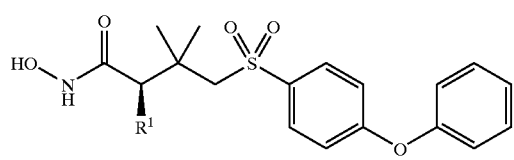
| Example | -R¹ |
|---|---|
| 1 | 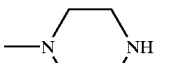 |
| 2 | 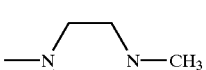 |
| 3 | 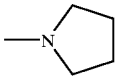 |
| 4 | 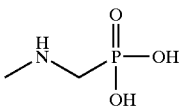 |
| 5 | 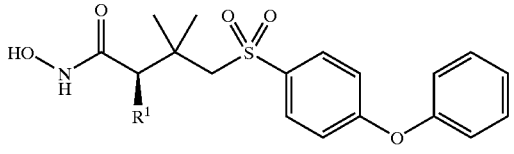 |
| 6 | 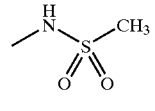 |
TABLE 2-continued
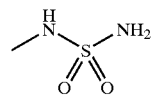
| Example | -R¹ |
|---|---|
| 7 | 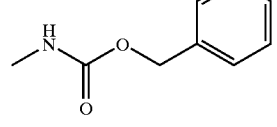 |
| 8 | 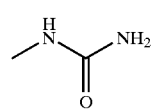 |
| 9 | 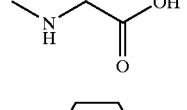 |
| 10 | 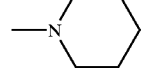 |
TABLE 3
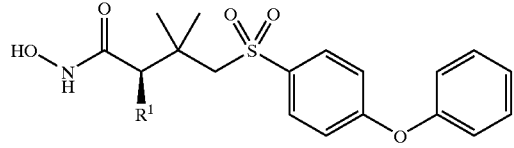
| Example | R¹ |
|---|---|
| 1 | 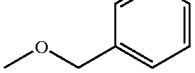 |
| 2 | 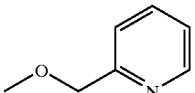 |
| 3 | 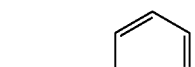 |
| 4 | 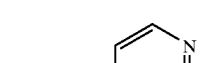 |
| 5 | 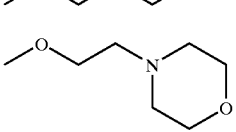 |

TABLE 3-continued

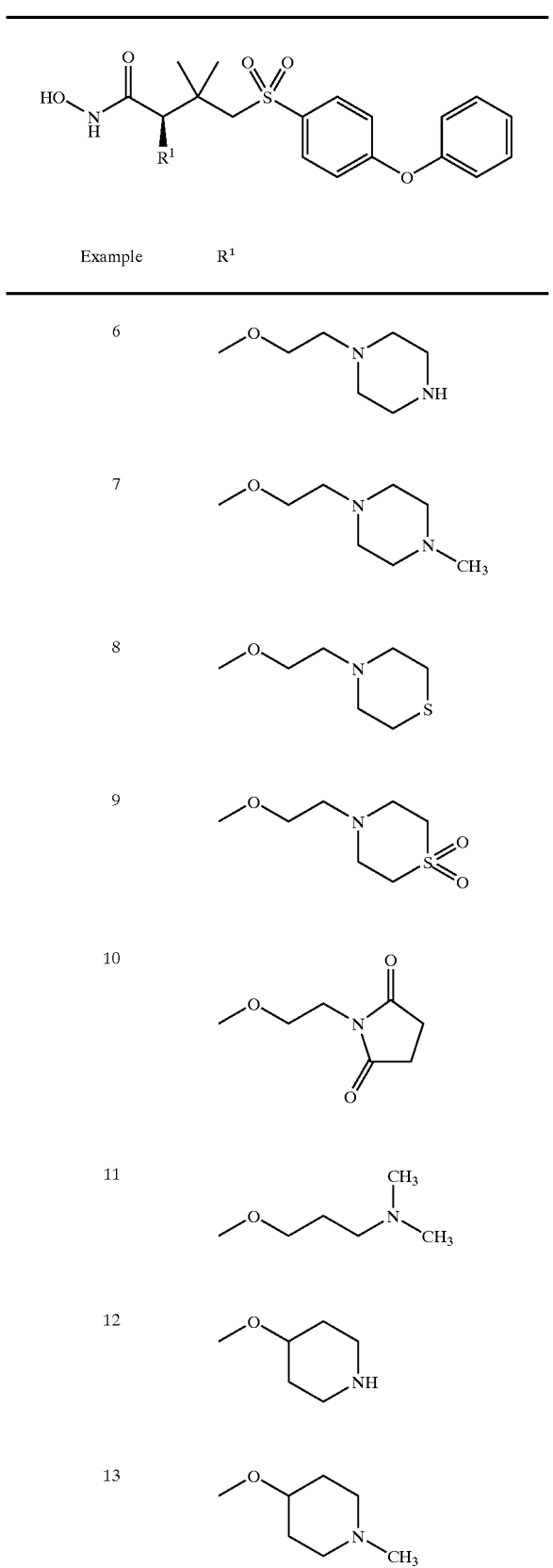

| Example | R¹ |
|---|---|
| 6 | (2-methoxyethyl)piperazine |
| 7 | 4-(2-methoxyethyl)-1-methylpiperazine |
| 8 | 4-(2-methoxyethyl)thiomorpholine |
| 9 | 4-(2-methoxyethyl)thiomorpholine 1,1-dioxide |
| 10 | 1-(2-methoxyethyl)pyrrolidine-2,5-dione |
| 11 | 3-methoxy-N,N-dimethylpropylamine |
| 12 | 4-methoxypiperidine |
| 13 | 4-methoxy-1-methylpiperidine |

TABLE 3-continued

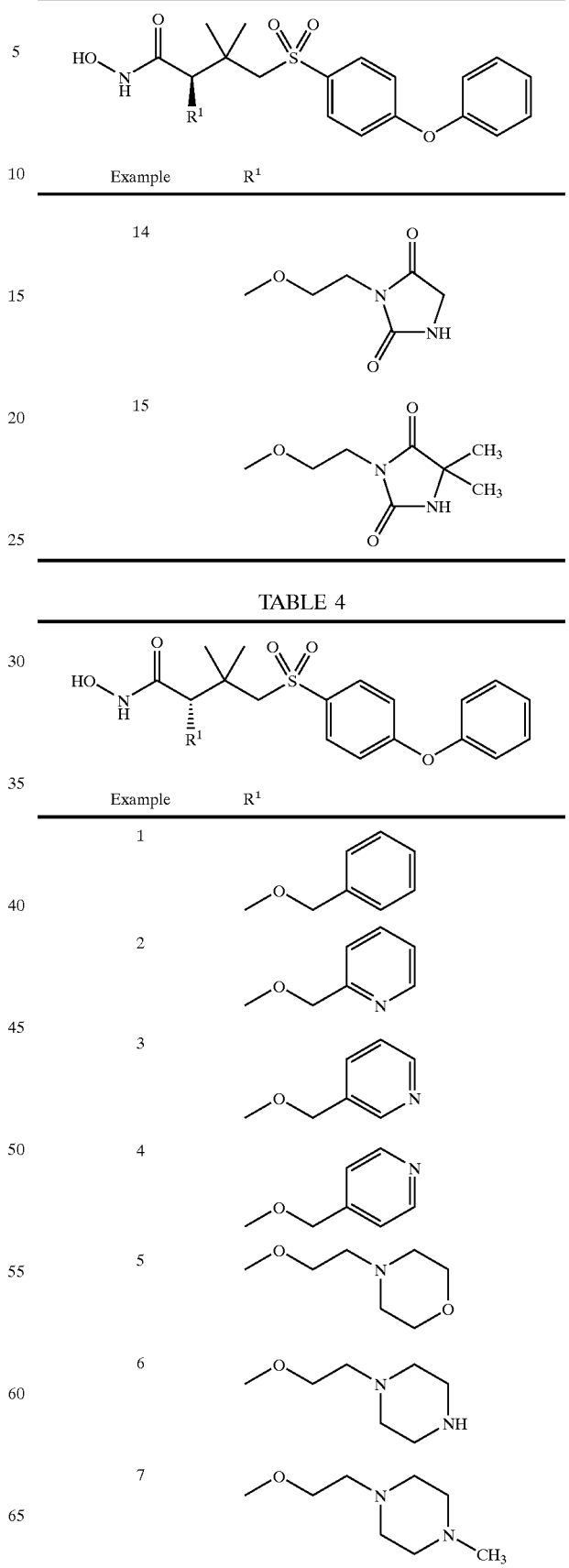

| Example | R¹ |
|---|---|
| 14 | 1-(2-methoxyethyl)imidazolidine-2,4-dione |
| 15 | 1-(2-methoxyethyl)-5,5-dimethylimidazolidine-2,4-dione |

TABLE 4

| Example | R¹ |
|---|---|
| 1 | benzyloxymethyl |
| 2 | (pyridin-2-yl)methoxymethyl |
| 3 | (pyridin-3-yl)methoxymethyl |
| 4 | (pyridin-4-yl)methoxymethyl |
| 5 | 2-(morpholin-4-yl)ethoxymethyl |
| 6 | 2-(piperazin-1-yl)ethoxymethyl |
| 7 | 2-(4-methylpiperazin-1-yl)ethoxymethyl |

TABLE 4-continued
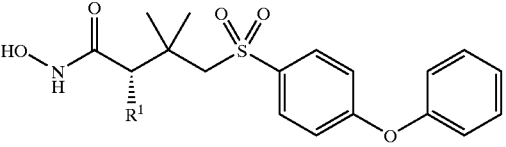
| Example | R¹ |
|---|---|
| 8 | 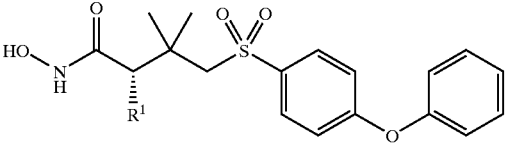 |
| 9 | 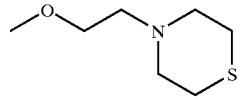 |
| 10 | 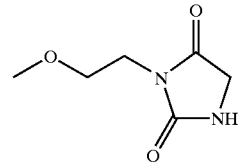 |
| 11 | 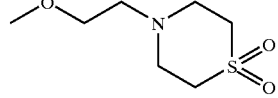 |
| 12 | 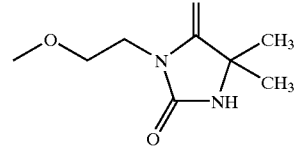 |
| 13 | 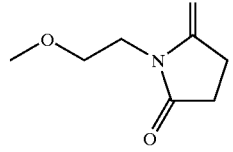 |
TABLE 4-continued
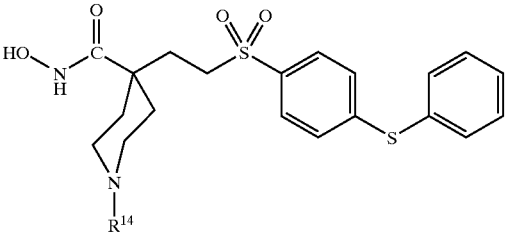
| Example | R¹ |
|---|---|
| 14 | 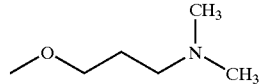 |
| 15 | 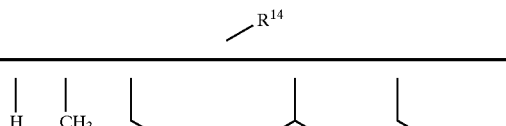 |
TABLE 5
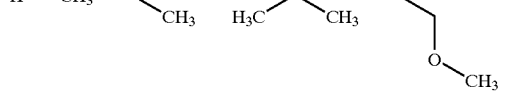
$R^{14}$
| H | CH₃ | 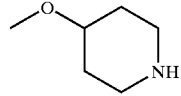 | 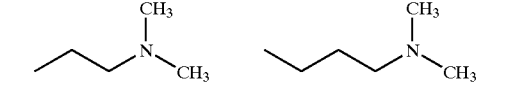 | 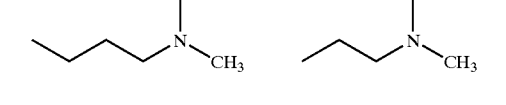 |
|---|---|---|---|---|
| 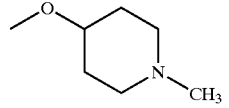 | 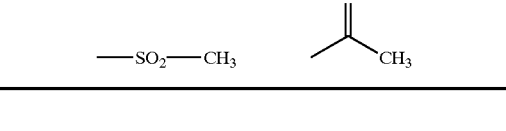 | | | |
|  | 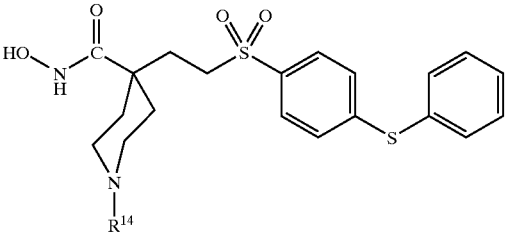 | | | |
| —SO₂—CH₃ | 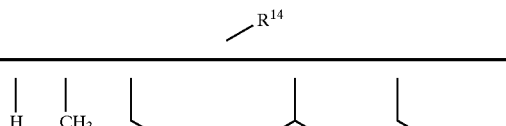 | | | |

TABLE 6
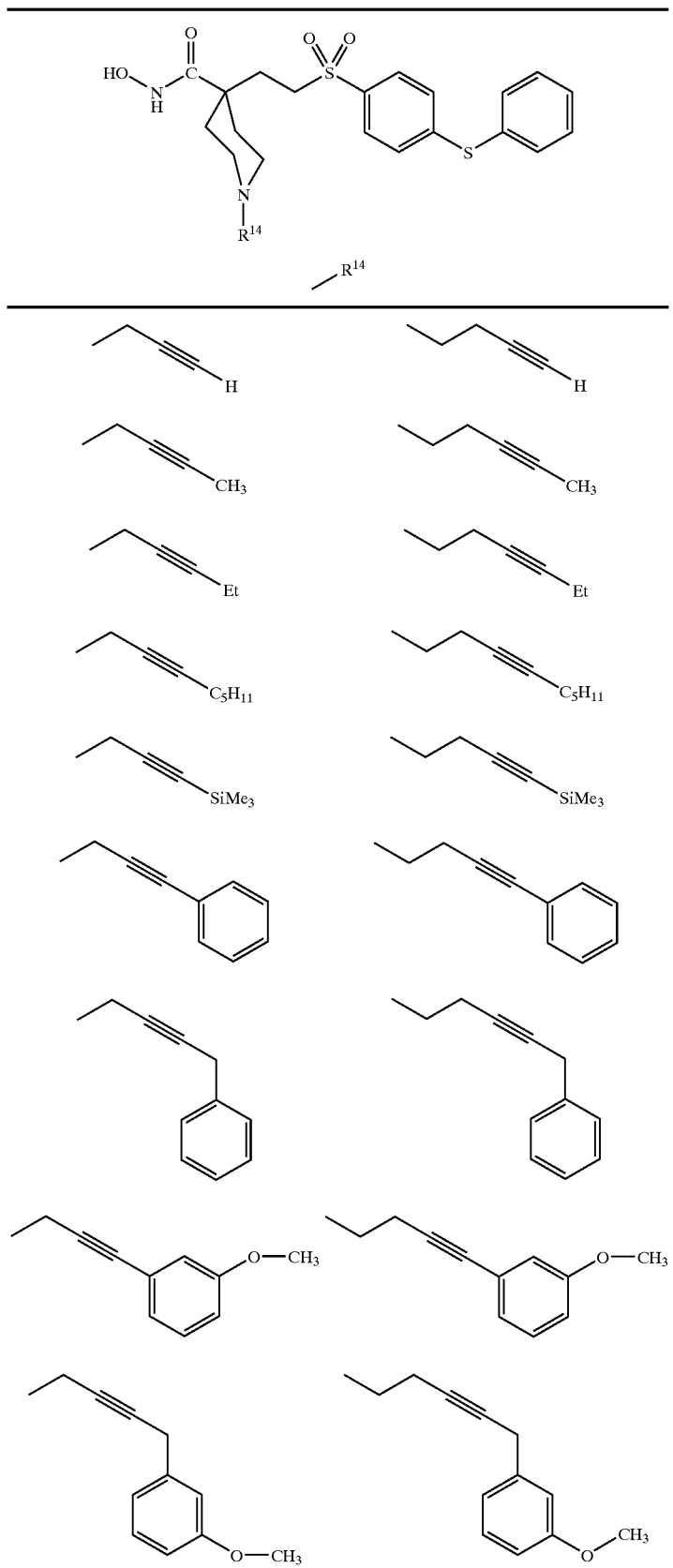

TABLE 6-continued
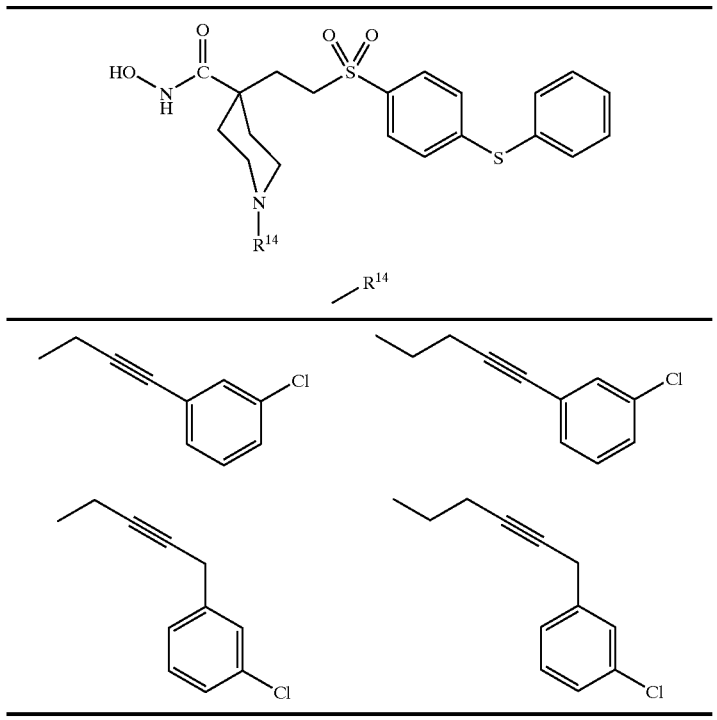
TABLE 7
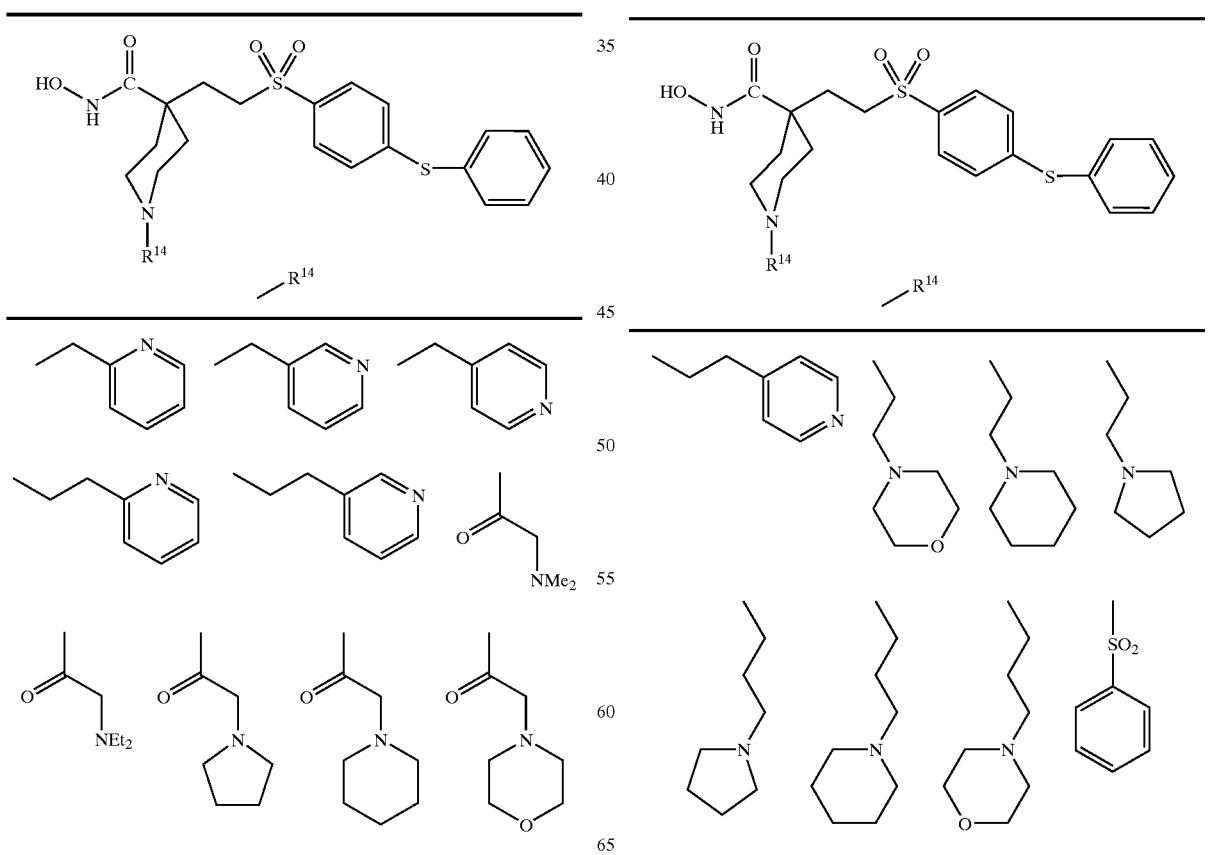

TABLE 7-continued
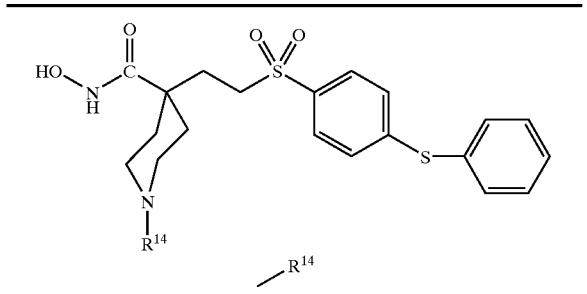
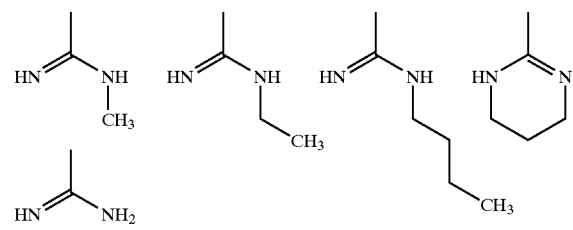
TABLE 8
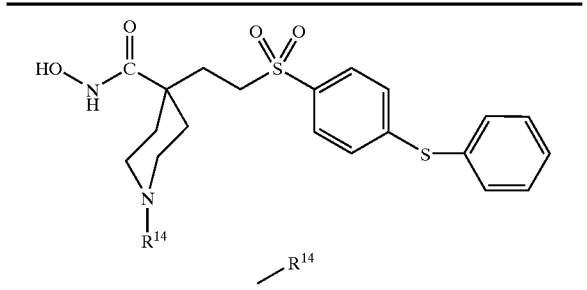
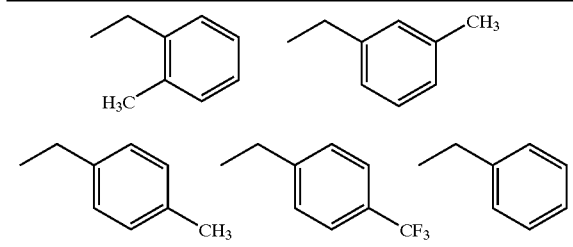
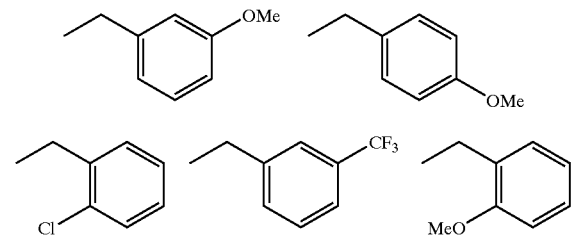
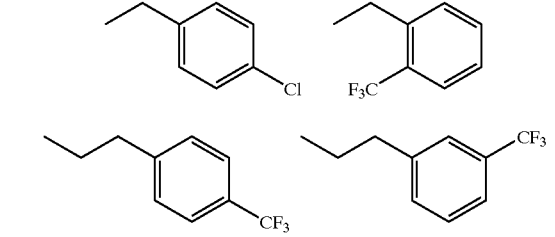
TABLE 8-continued
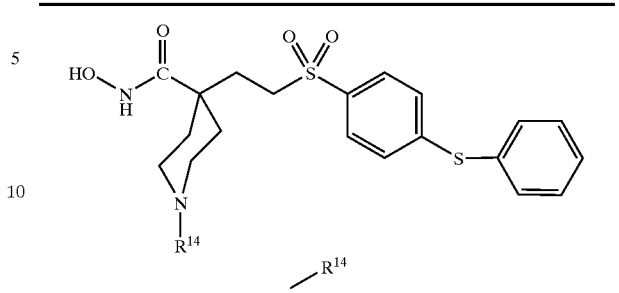
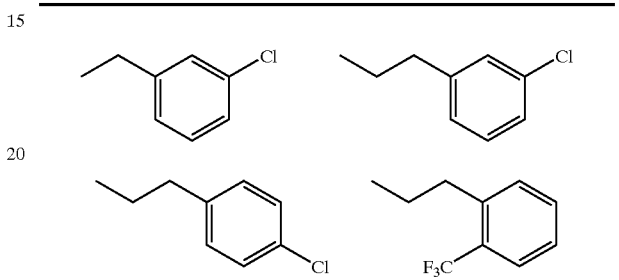
TABLE 9
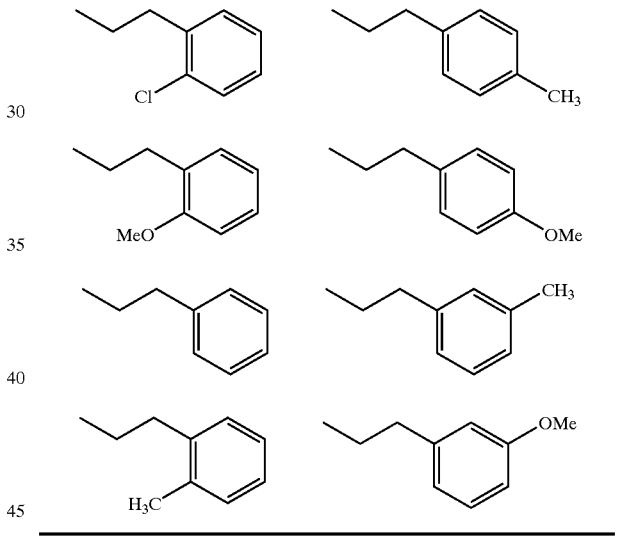
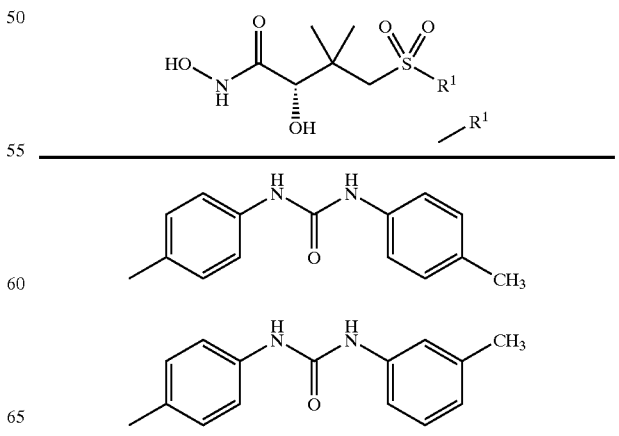

TABLE 9-continued
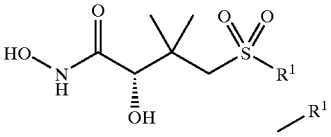

TABLE 9-continued

![structure with HO-NH-C(=O)-C*(OH)-C(CH3)2-CH2-S(=O)2-R1, R1 substituent]

TABLE 10-continued

![structure with HO-NH-C(=O)-C*(OH)-C(CH3)2-CH2-S(=O)2-R1, R1 substituent]

TABLE 10

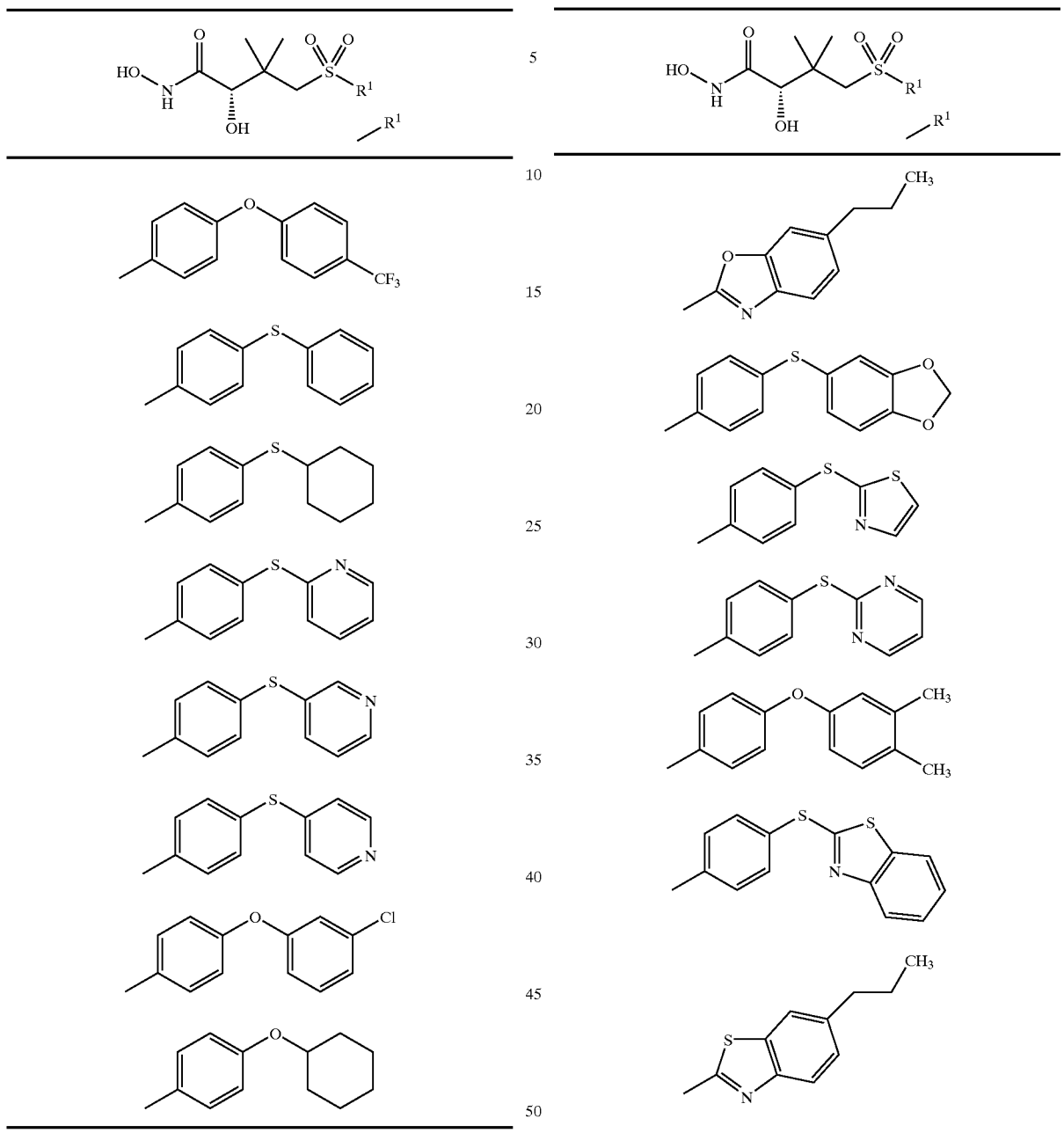

TABLE 11-continued
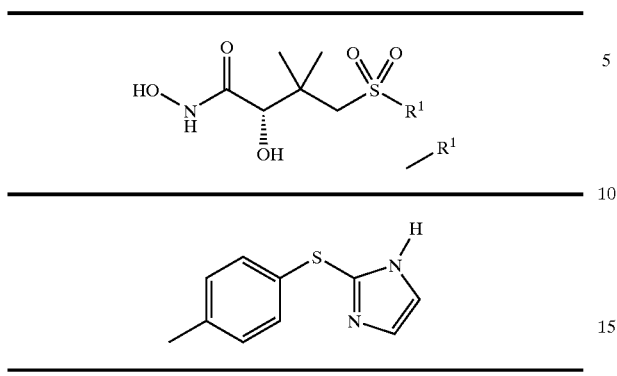
TABLE 12
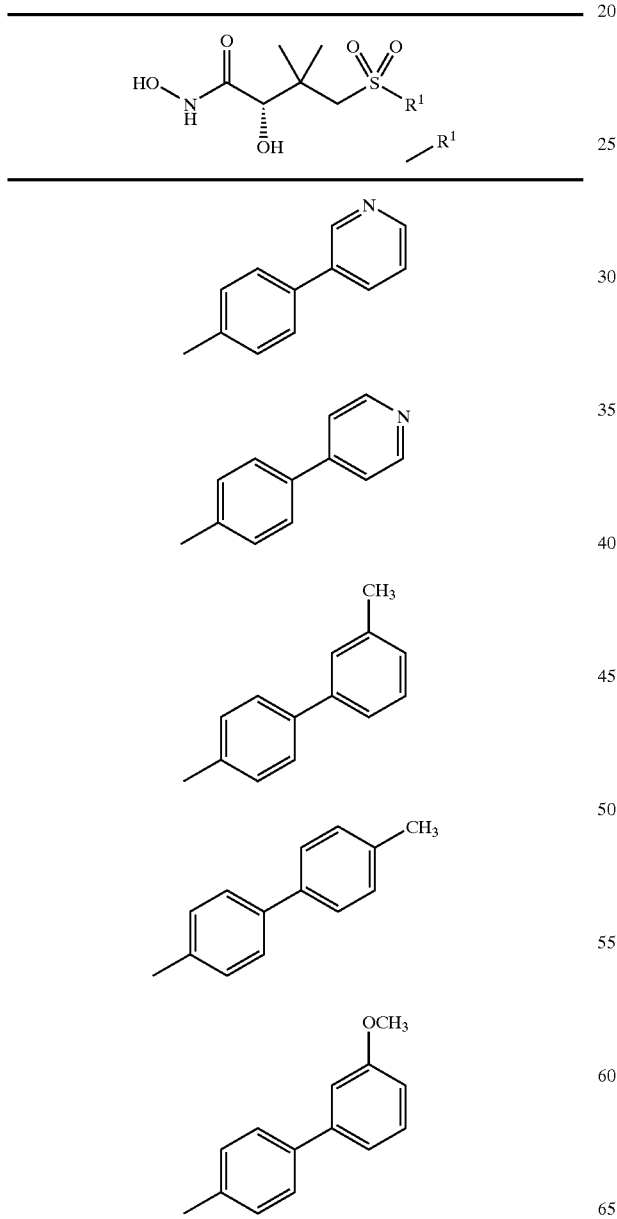
TABLE 12-continued
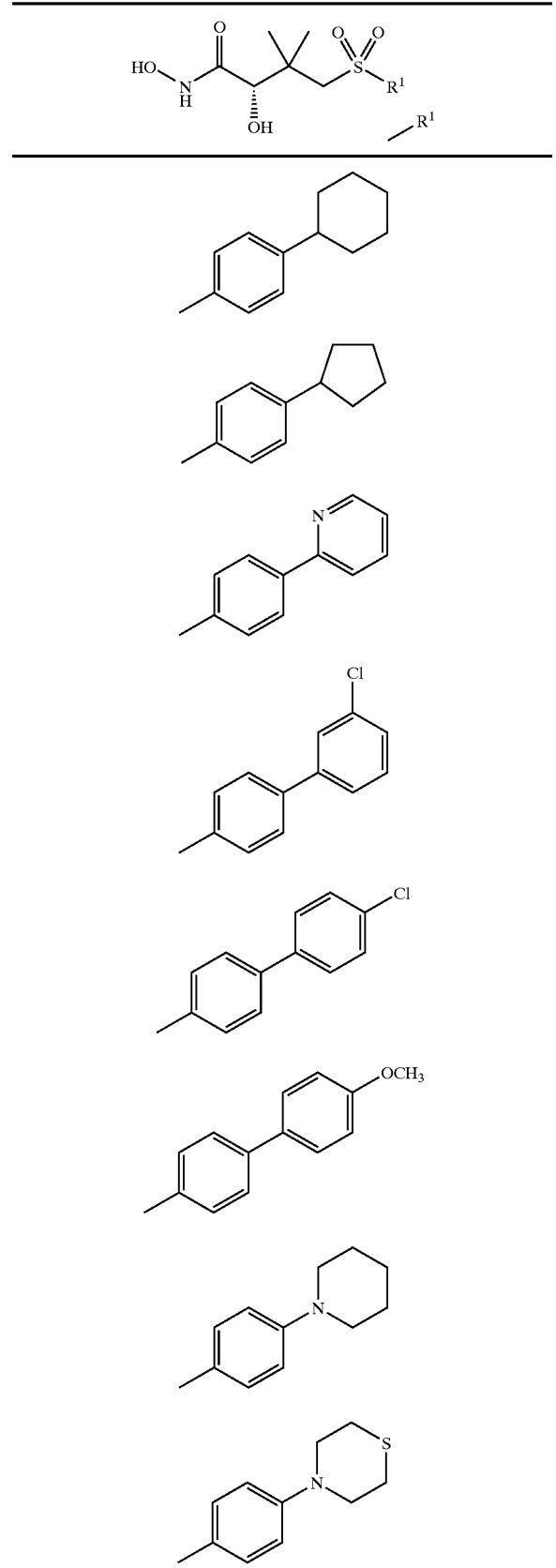

TABLE 12-continued

[Structure: (S)-N-hydroxy-2-hydroxy-3,3-dimethyl-4-(sulfonyl-R¹)butanamide core with R¹ substituents shown below]

R¹ groups:
- 4-methylbiphenyl
- 3'-trifluoromethyl-4-methylbiphenyl
- 4'-trifluoromethyl-4-methylbiphenyl
- 4'-isopropoxy-4-methylbiphenyl
- 4-(morpholin-4-yl)phenylmethyl

TABLE 13

[Structure: (S)-N-hydroxy-2-hydroxy-3,3-dimethyl-4-(sulfonyl-R¹)butanamide core with R¹ substituents shown below]

R¹ groups:
- 4-(phenylsulfonamido)phenylmethyl
- 4-(but-3-enyloxy)phenylmethyl
- 4-(trifluoroacetamido)phenylmethyl

TABLE 13-continued

R¹ groups:
- 4-(but-3-ynyloxy)phenylmethyl
- 4-(phenylcarbamoylmethoxy)phenylmethyl
- 4-acetamidophenylmethyl
- 5-(pentanoylamino)thiophen-2-ylmethyl
- 4-propionamidophenylmethyl
- 5-(pyridin-2-yl)thiophen-2-ylmethyl
- 4-butyramidophenylmethyl
- 4-(methanesulfonamido)phenylmethyl
- 4-(phenylacetamido)phenylmethyl
- 4-pentylphenylmethyl
- 4-(butylamino)phenylmethyl TABLE 13-continued
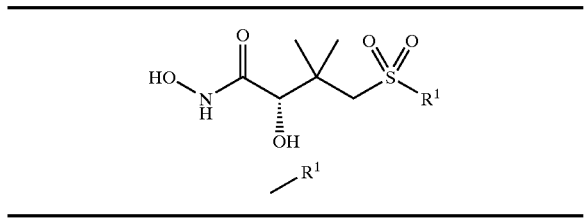
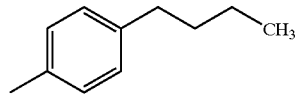
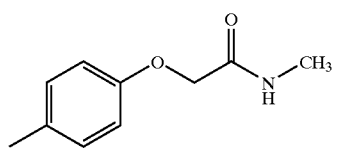
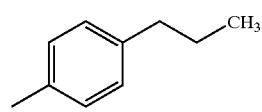
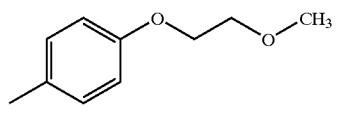
TABLE 14
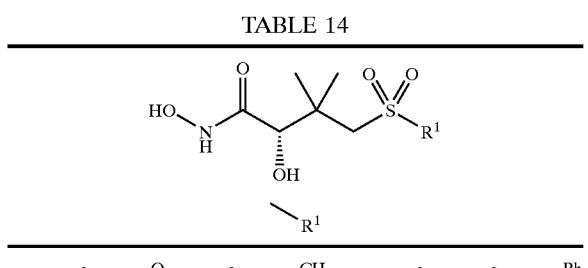
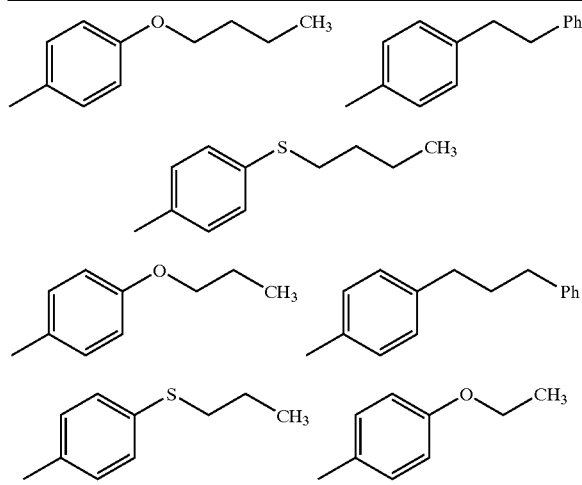
TABLE 14-continued
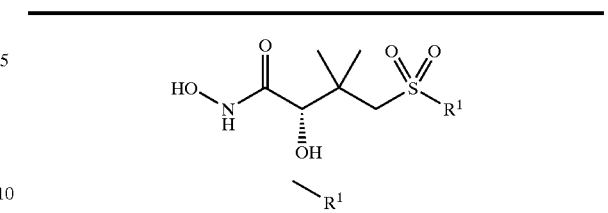
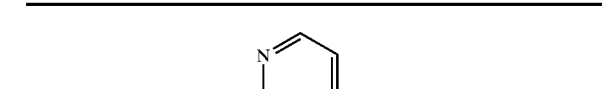
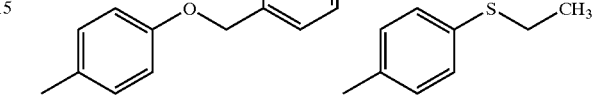
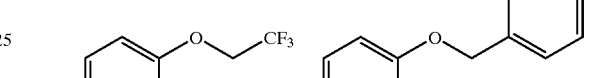
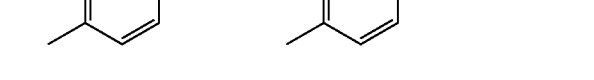
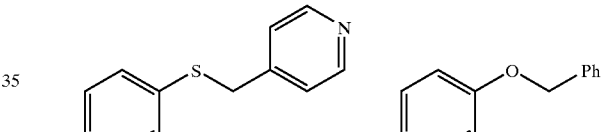
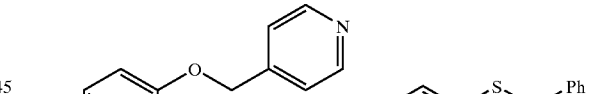
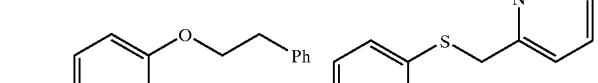
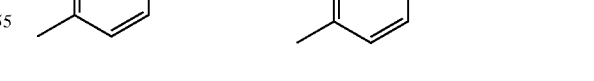
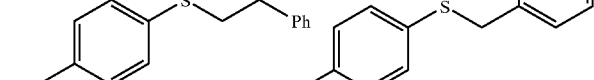
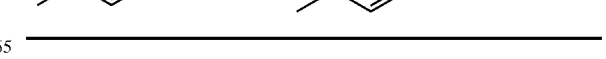

TABLE 15
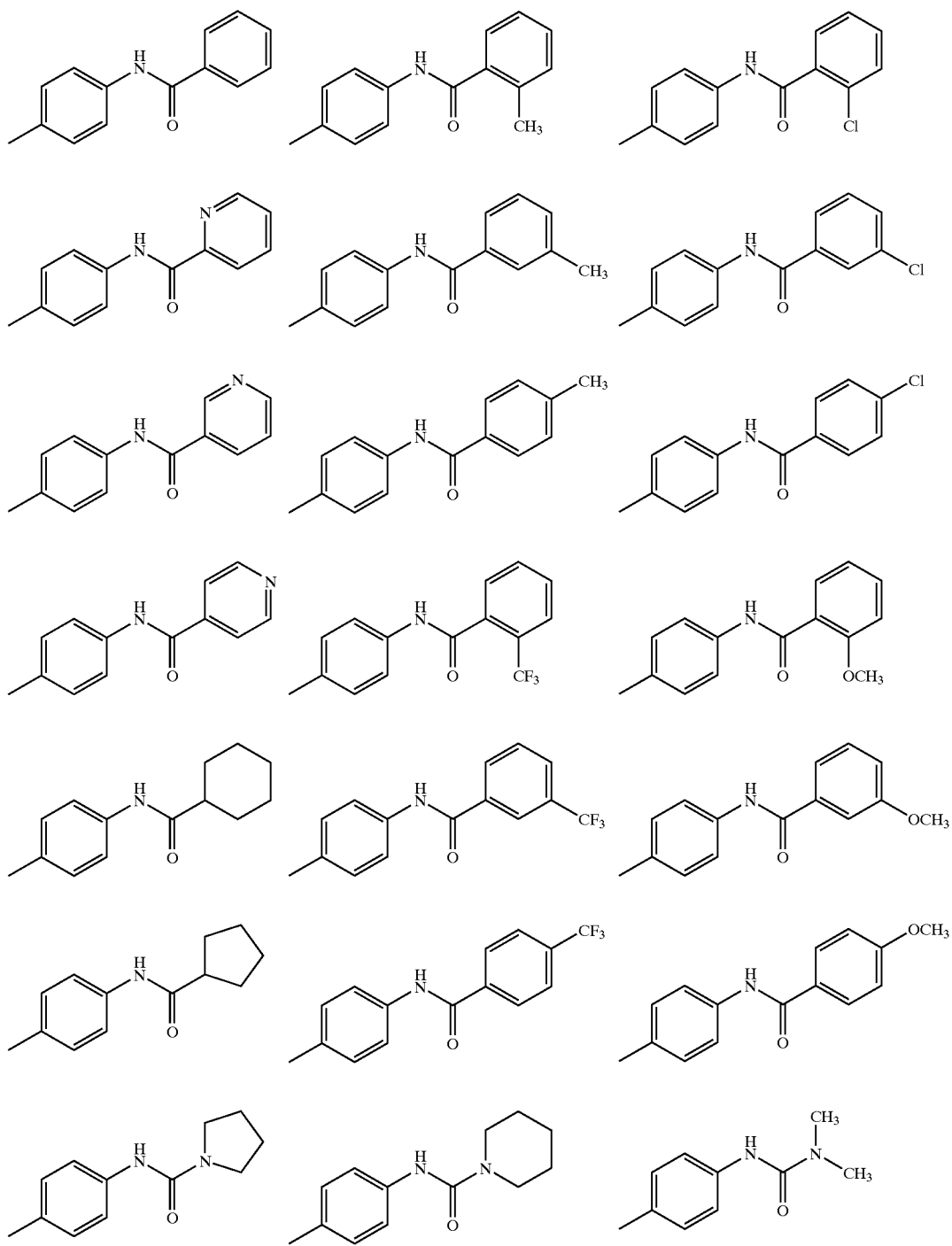

TABLE 16
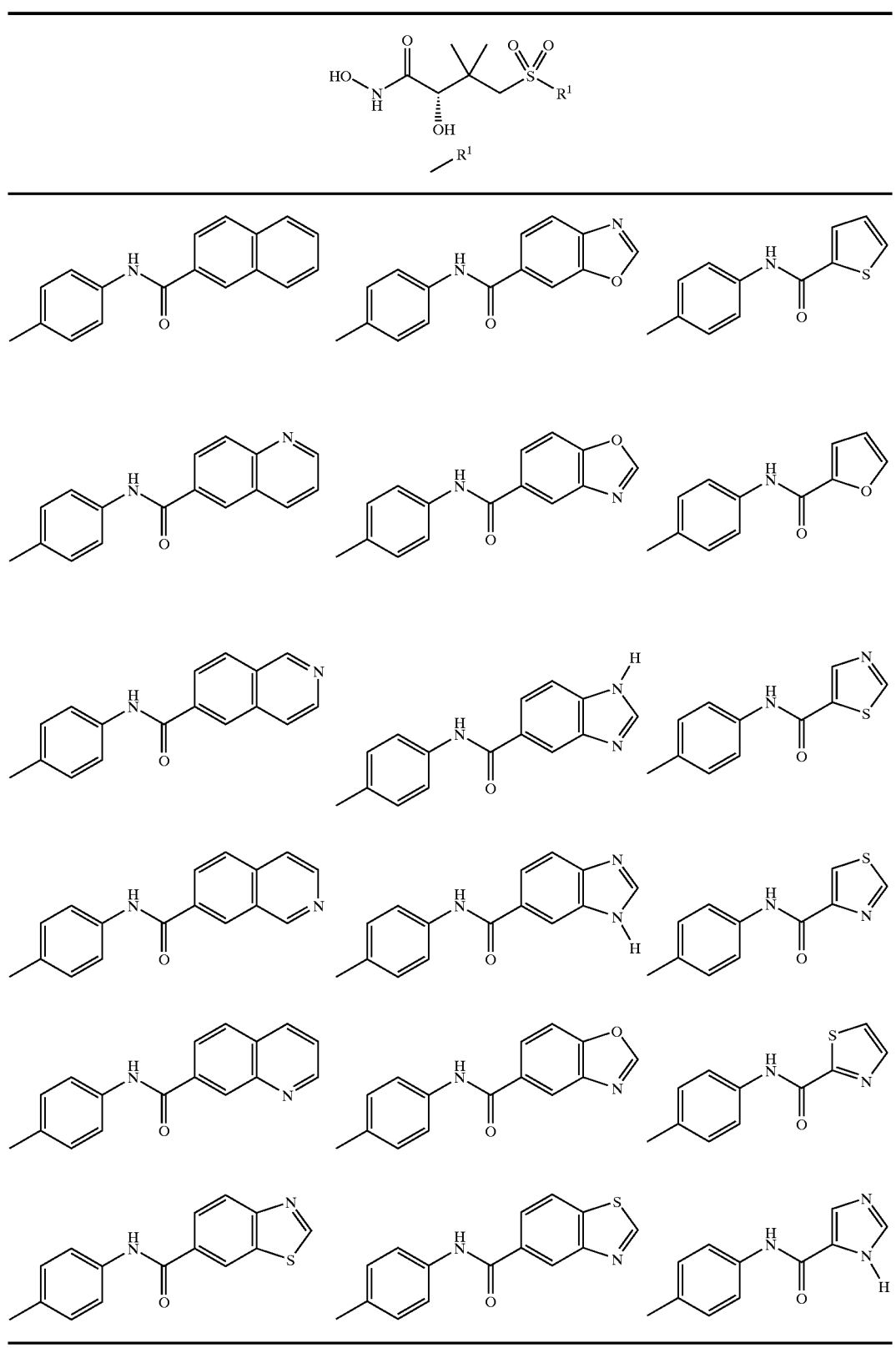

TABLE 17

[Structure: HO-NH-C(=O)-CH(OH)-C(CH3)2-CH2-S(=O)2-C6H4-X]

| Example | —X |
|---------|-----|
| 1 | 4-phenyl-1-methylpiperidin-4-yl |
| 2 | 3-methyl-1-methylpiperidinyl |
| 3 | 4-hydroxy-4-phenyl-1-methylpiperidinyl |
| 4 | 1-methylpiperidine-4-carboxylic acid ethyl ester |
| 5 | 1-methylpiperidine-4-carboxamide |
| 6 | 1-methylpiperidine-3-carboxamide |
| 7 | 1-methyl-4,4-(ethylenedioxy)piperidinyl (1,4-dioxa-8-azaspiro[4.5]decane) |
| 8 | 4-methylmorpholinyl |
| 9 | 1,3,5-trimethylpiperidinyl |
| 10 | 4-methylpiperazinyl (NH) |
| 11 | 4-methyl-1-phenylpiperazinyl |

TABLE 17-continued

[Structure: HO-NH-C(=O)-CH(OH)-C(CH3)2-CH2-S(=O)2-C6H4-X]

| Example | —X |
|---------|-----|
| 12 | 4-methyl-1-(4-acetylphenyl)piperazinyl |
| 13 | 4-methyl-1-(3-trifluoromethylphenyl)piperazinyl |
| 14 | 4-methyl-1-(4-fluorophenyl)piperazinyl |
| 15 | 4-methyl-1-(4-nitrophenyl)piperazinyl |
| 16 | 4-methyl-1-(3-fluorophenyl)piperazinyl |

TABLE 18

[Structure: HO-NH-C(=O)-CH(OH)-C(CH3)2-CH2-S(=O)2-C6H4-X]

| Example | —X |
|---------|-----|
| 1 | 4-phenyl-1-methylpiperidin-4-yl |
| 2 | 3-methyl-1-methylpiperidinyl |
| 3 | 4-hydroxy-4-phenyl-1-methylpiperidinyl |

TABLE 18-continued
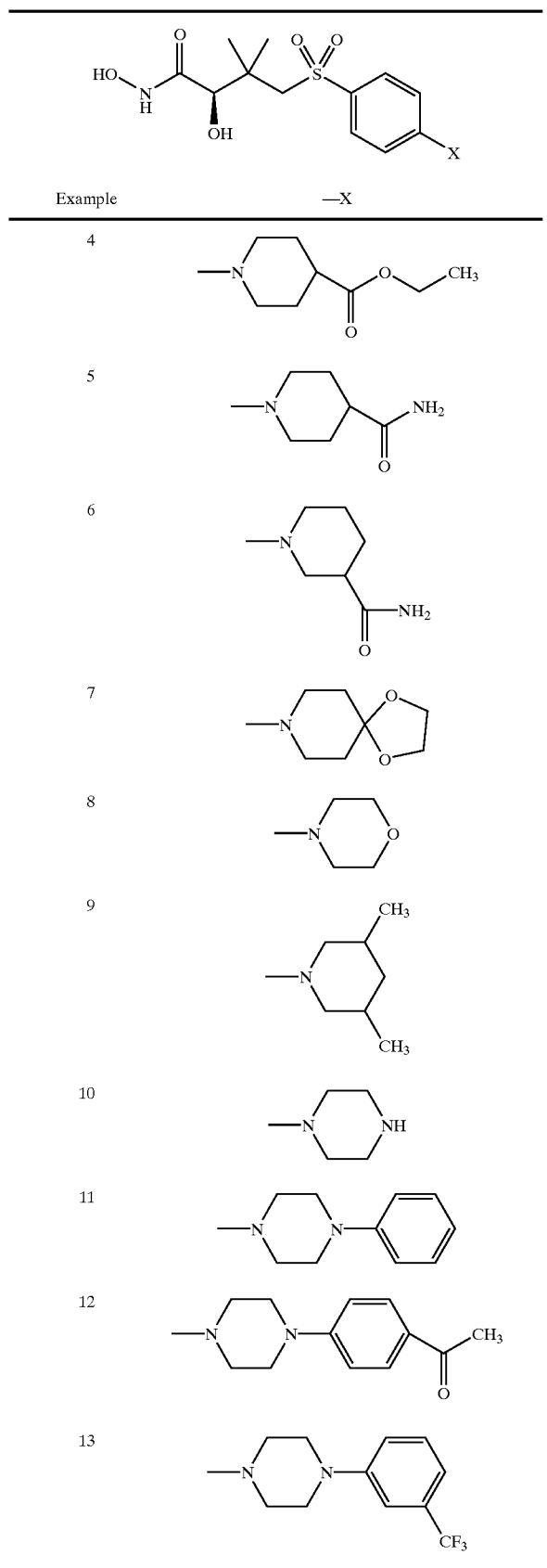
TABLE 18-continued
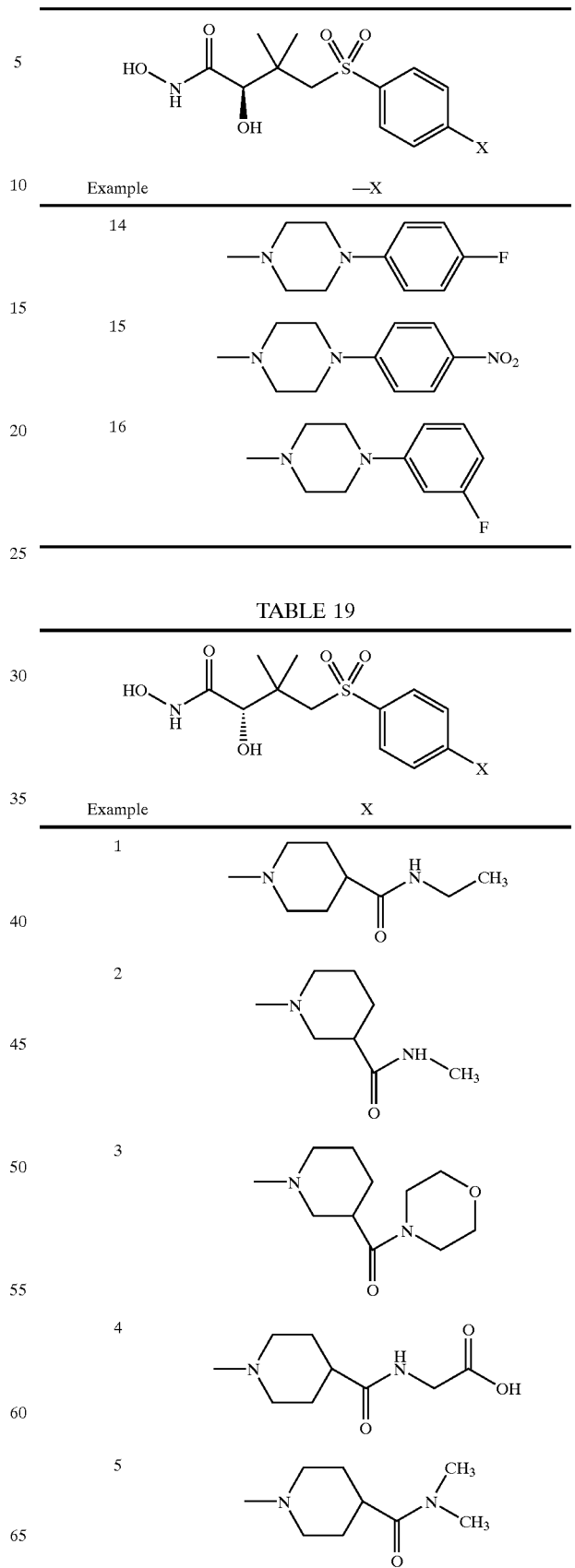

TABLE 19-continued
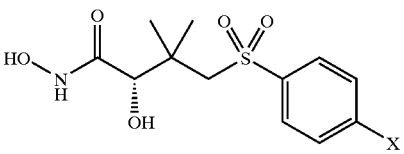
| Example | X |
|---|---|
| 6 | 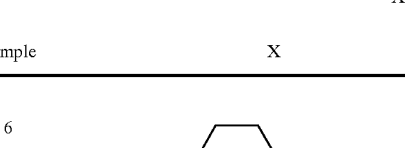 |
| 7 | 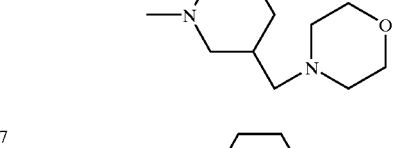 |
| 8 | 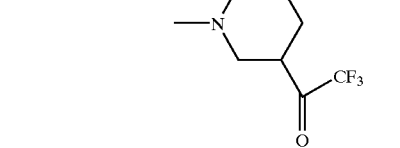 |
| 9 | 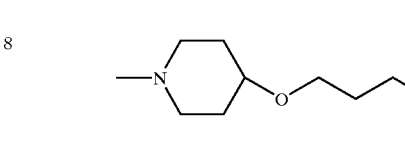 |
| 10 | 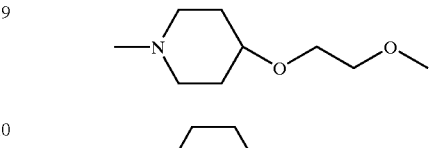 |
| 11 | 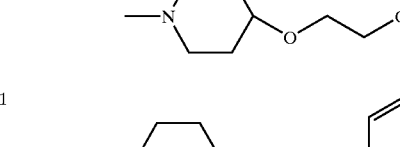 |
TABLE 20
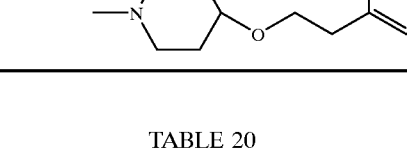
| Example | R¹ | R² |
|---|---|---|
| 1 | —H | —H |
| 2 | —H | —CH₃ |
| 3 | —CH₃ | —CH₃ |
| 4 | —H | —OH |
| 5 | —CH₃ | —OH |
| 6 | —CH₃ | —NH₂ |
TABLE 20-continued
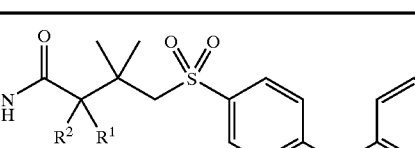
| Example | R¹ | R² |
|---|---|---|
| 7 | | 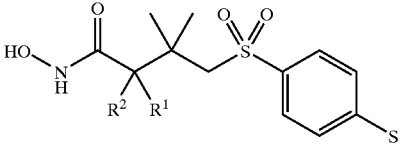 |
| 8 | | 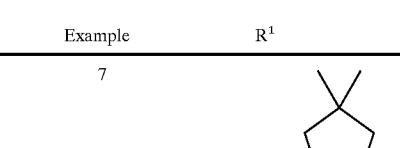 |
| 9 | |  |
| 10 | |  |
| 11 | |  |
| 12 | |  |
| 13 | |  |
| 14 | |  |

TABLE 20-continued
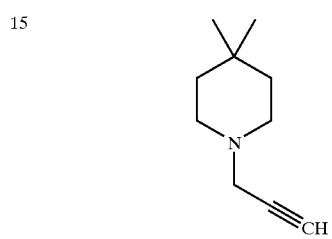
| Example | R¹ | R² |
|---|---|---|
| 15 | 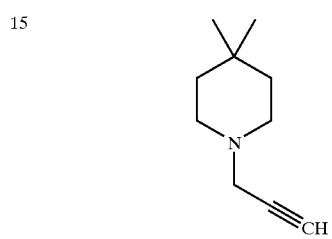 | |
| 16 | 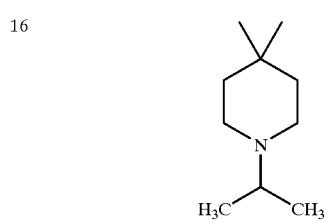 | |
| 17 | 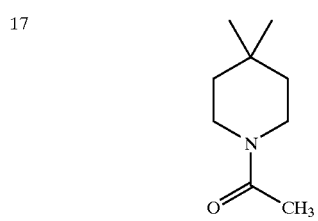 | |
| 18 | 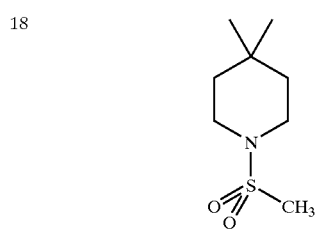 | |
| 19 | 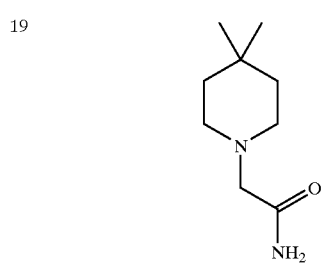 | |
TABLE 20-continued
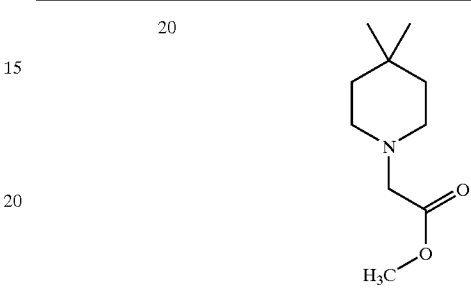
| Example | R¹ | R² |
|---|---|---|
| 20 | 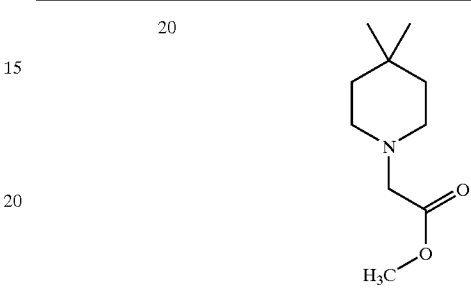 | |
| 21 | 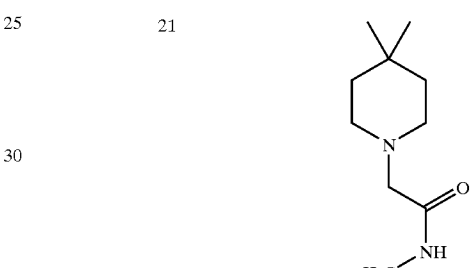 | |
| 22 | 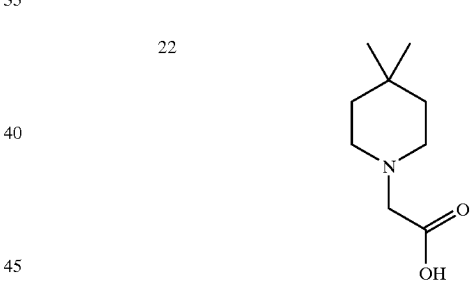 | |
TABLE 21
| Example | R¹ | R² | X | Ar |
|---|---|---|---|---|
| 1 | | | O | 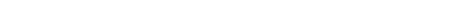 |
| 2 | | | O | |

TABLE 21-continued

Structure: HO-NH-C(=O)-C(R²)(R¹)-C(CH₃)₂-CH₂-S(=O)₂-C₆H₄-X-Ar

| Example | R¹ | R² | X | Ar |
|---------|----|----|----|-----|
| 3 | 1-methylcyclobutyl | | O | 4-pyridyl |
| 4 | 1-methylcyclobutyl | | O | 3-pyridyl |
| 5 | 1-methylcyclopentyl | | O | 4-pyridyl |
| 6 | 1-methylcyclopentyl | | O | 3-pyridyl |
| 7 | 1-methylcyclohexyl | | O | 4-pyridyl |
| 8 | 1-methylcyclohexyl | | O | 3-pyridyl |
| 9 | 1-methylcyclohexyl | | S | phenyl |
| 10 | 1-methylcyclohexyl | | S | 4-chlorophenyl |

TABLE 22

Structure: HO-NH-C(=O)-CH₂-CH(R¹)-CH₂-S(=O)₂-C₆H₄-O-C₆H₅

| Example | —R¹ |
|---------|-----|
| 1 | —NH-S(=O)₂-CH₃ |
| 2 | —NH-S(=O)₂-NH₂ |
| 3 | —NH-C(=O)-O-CH₂-C₆H₅ |
| 4 | —NH-C(=O)-NH₂ |
| 5 | —NH-CH₂-C(=O)-OH |
| 6 | piperidin-1-yl |
| 7 | piperazin-1-yl |
| 8 | 4-methylpiperazin-1-yl |
| 9 | pyrrolidin-1-yl |
| 10 | —NH-CH₂-P(=O)(OH)₂ |

TABLE 23
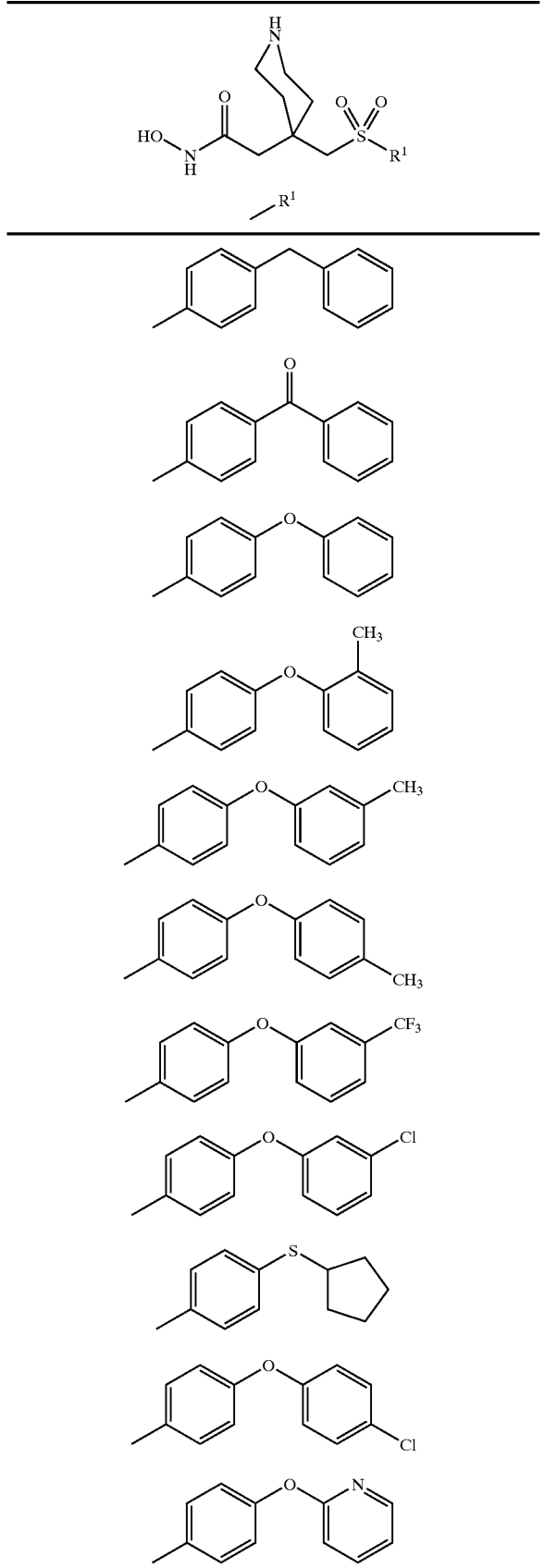
TABLE 23-continued
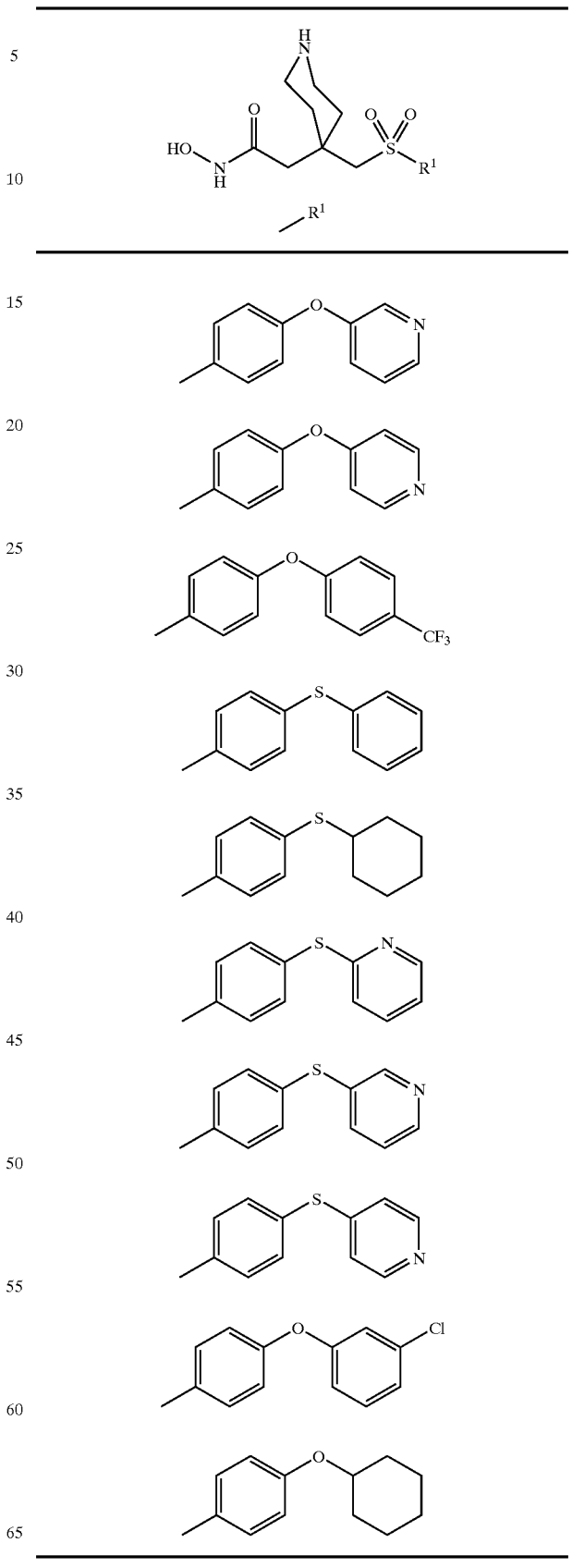

TABLE 24
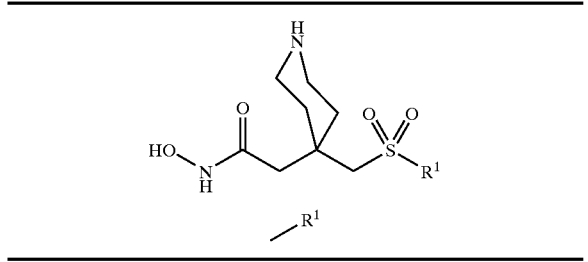
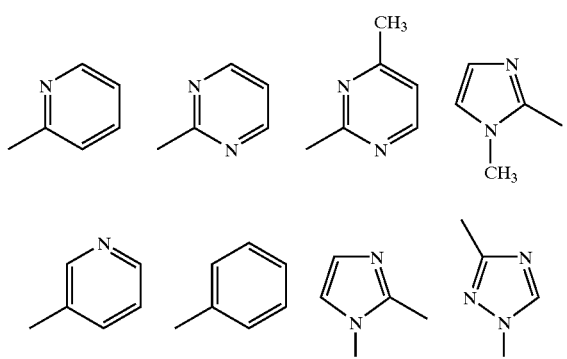
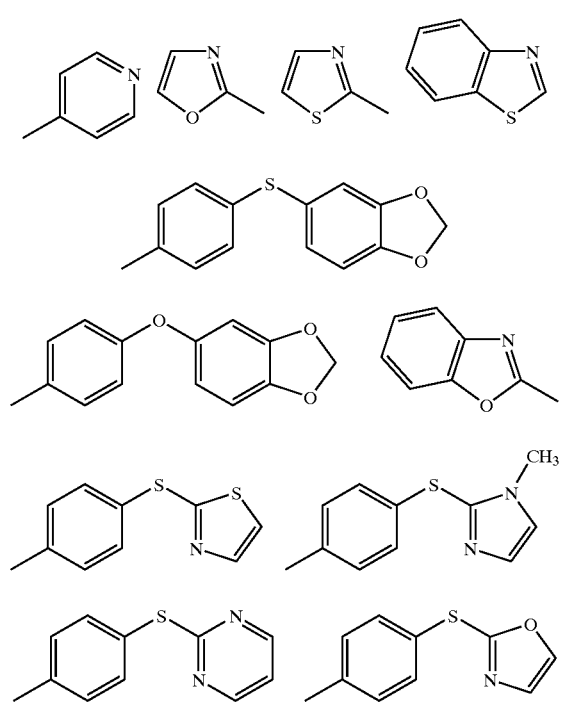
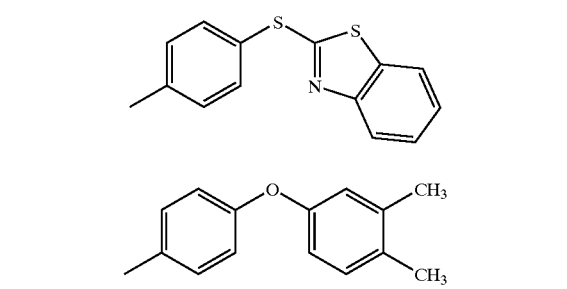
TABLE 24-continued
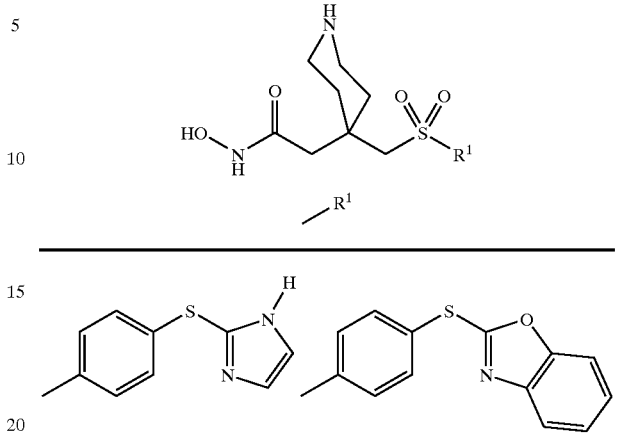
TABLE 25
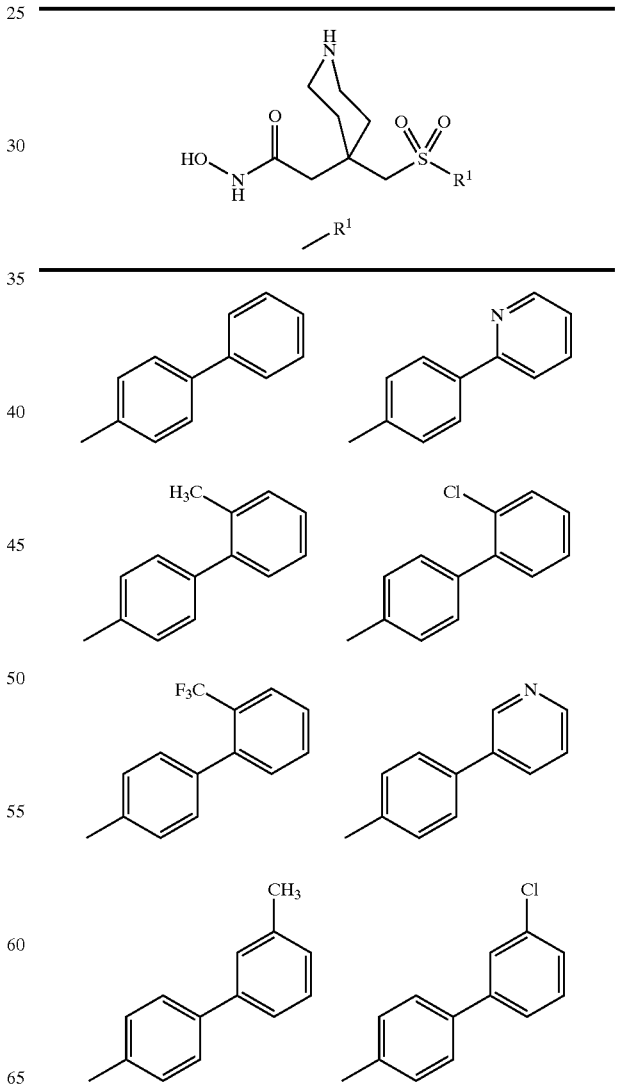

TABLE 25-continued
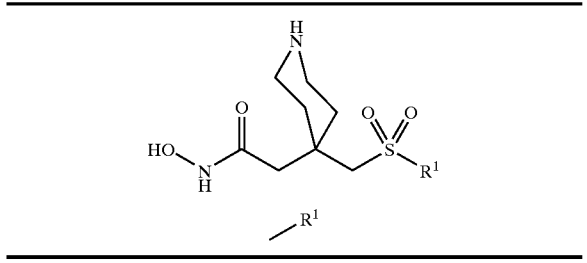
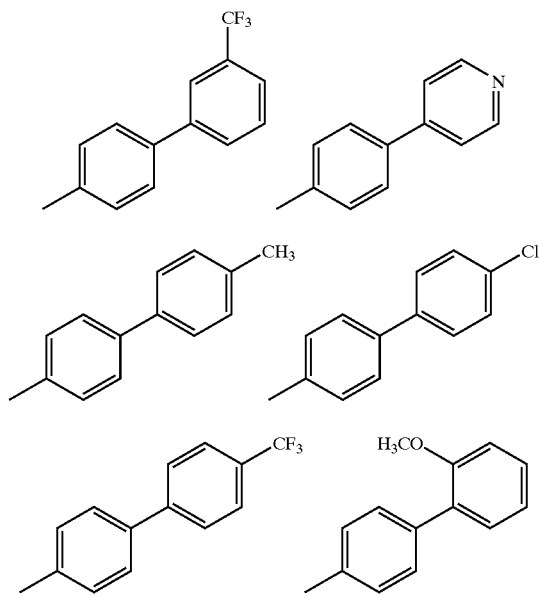
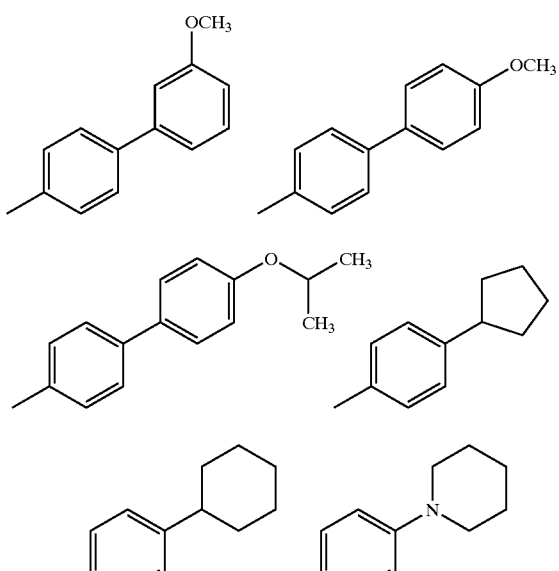
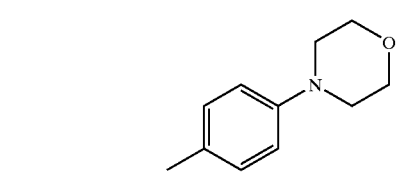
TABLE 26
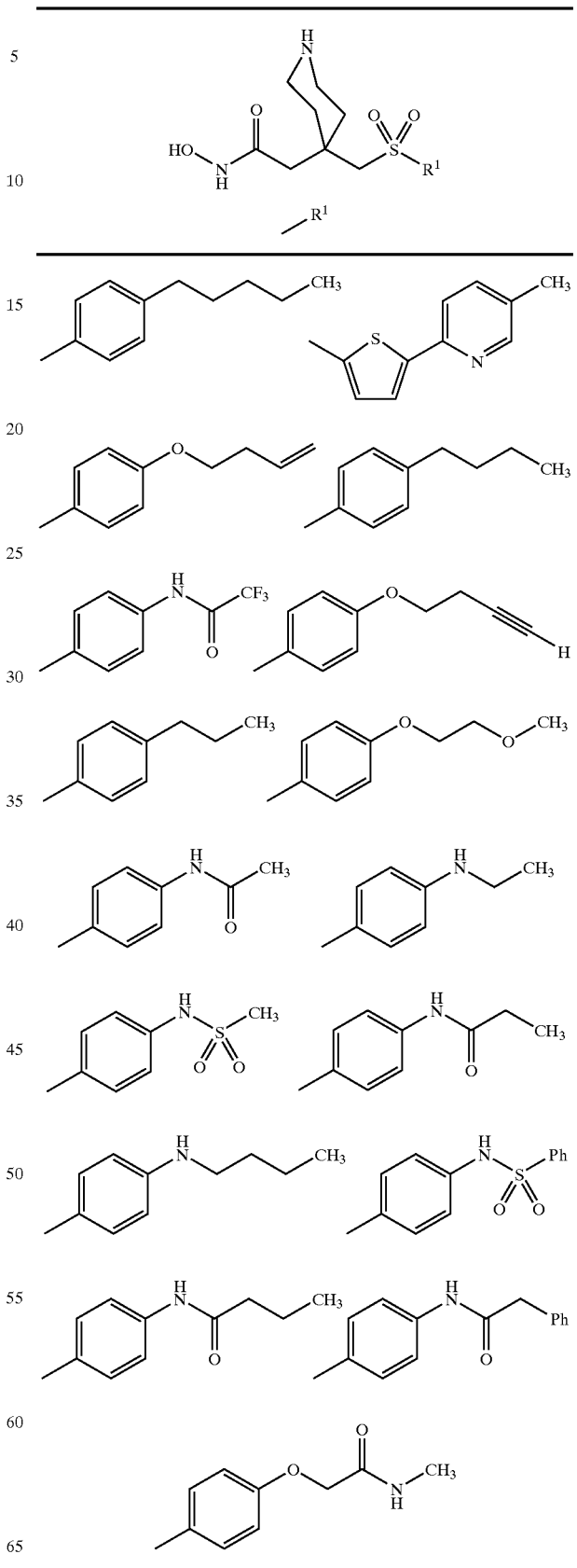

TABLE 26-continued
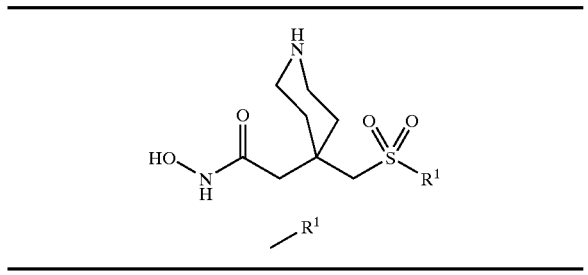
TABLE 27
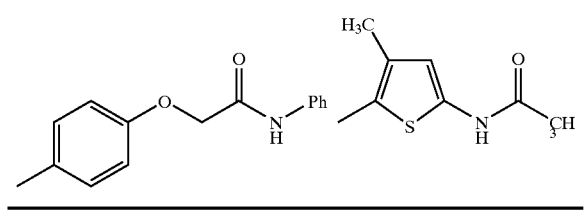
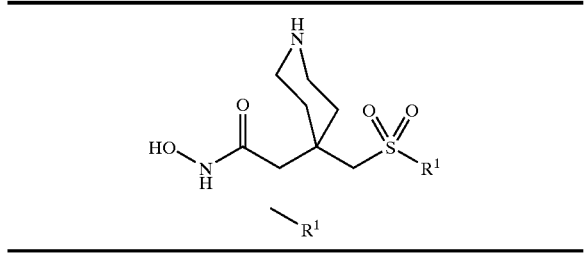
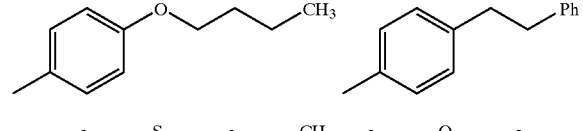
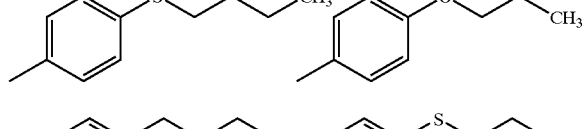
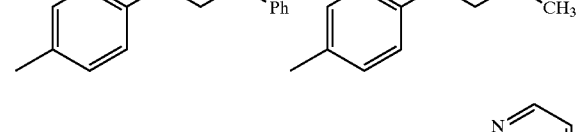
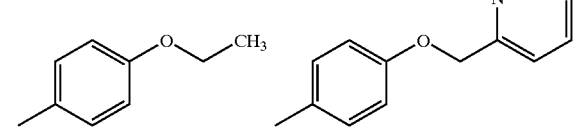
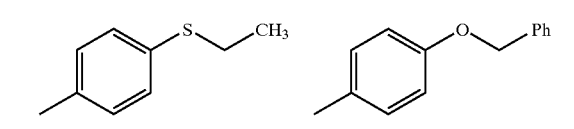
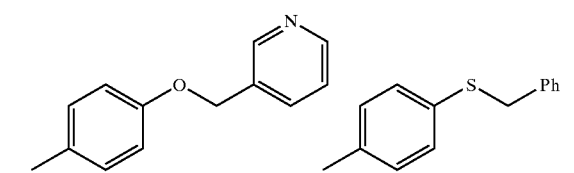
TABLE 27-continued
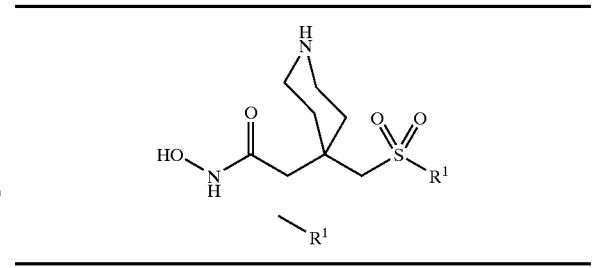
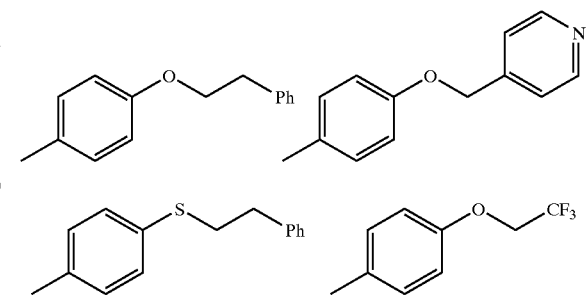
TABLE 28
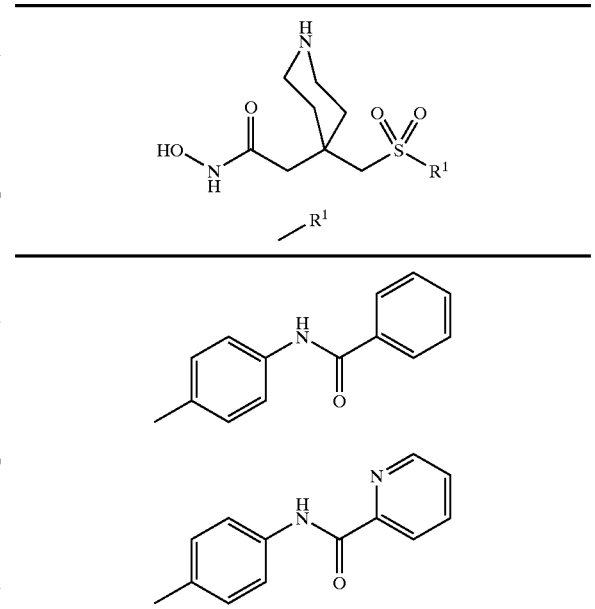

TABLE 28-continued
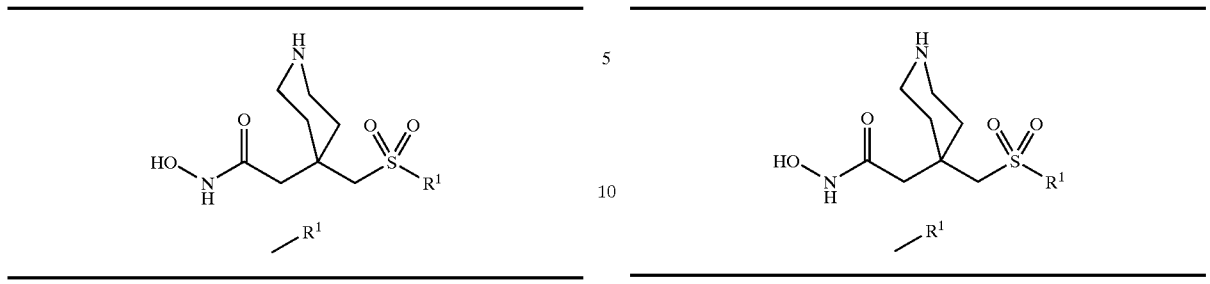
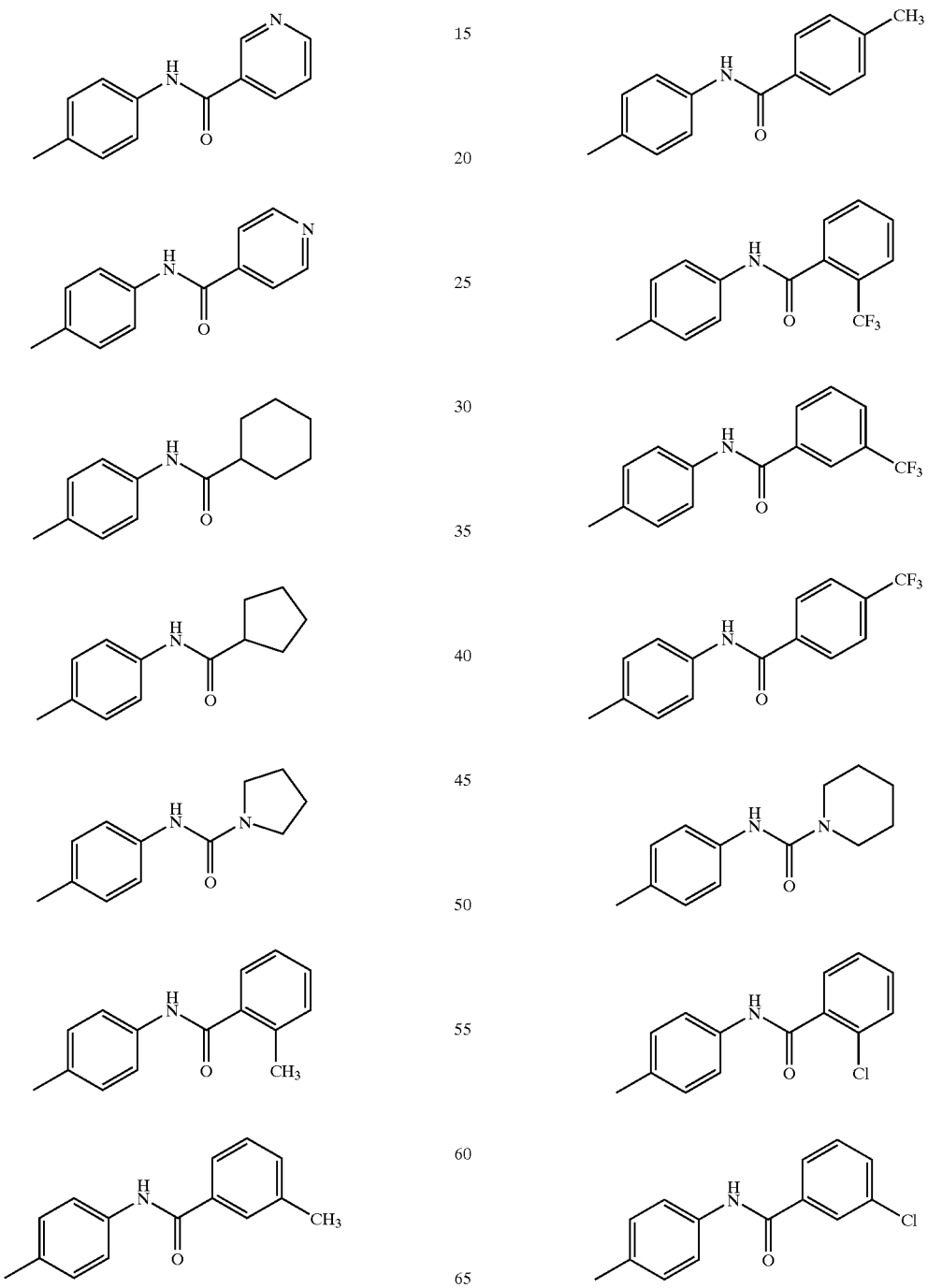

TABLE 28-continued
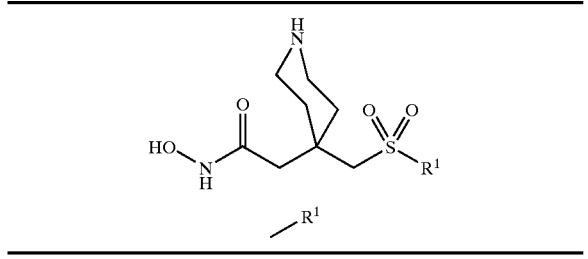
—R¹
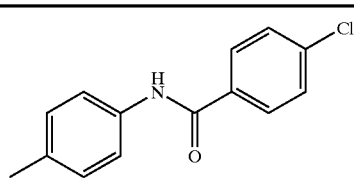
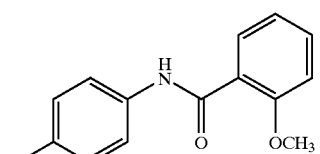
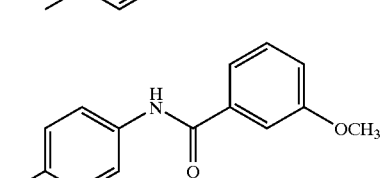
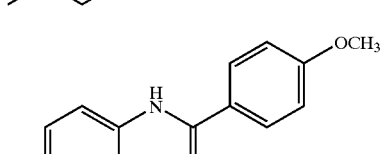
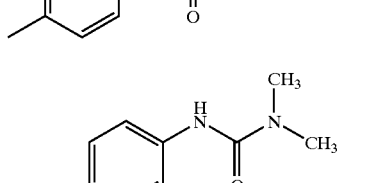
TABLE 29
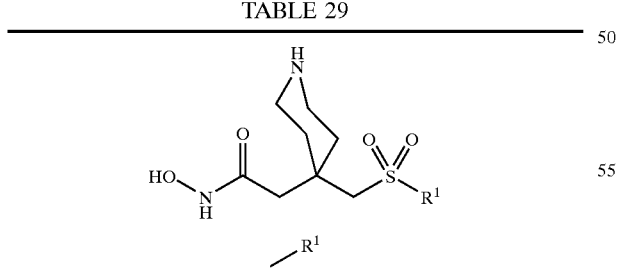
—R¹
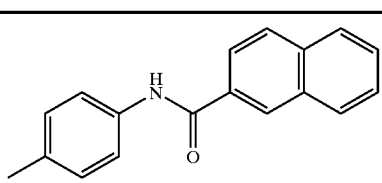
TABLE 29-continued
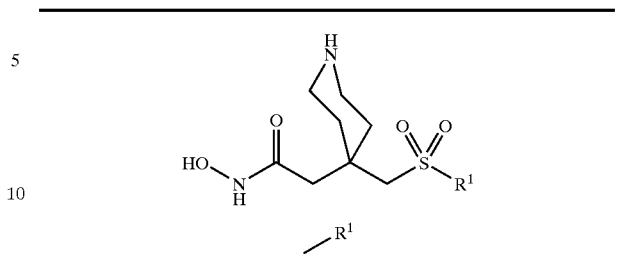
—R¹
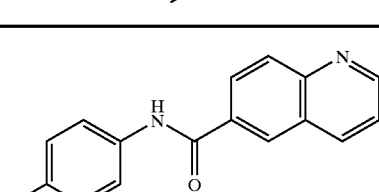
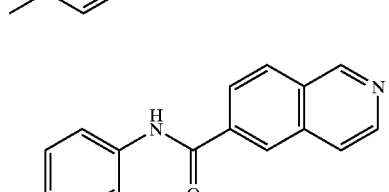
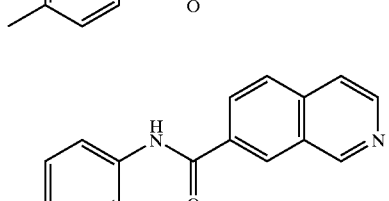
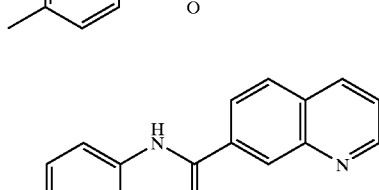
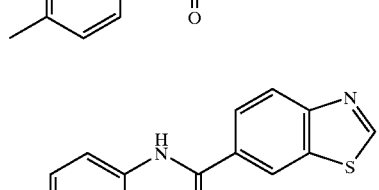
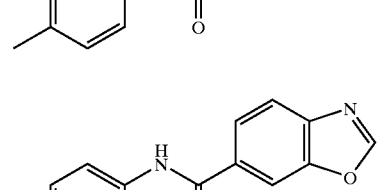
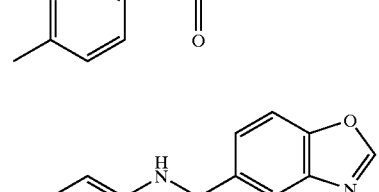

TABLE 29-continued
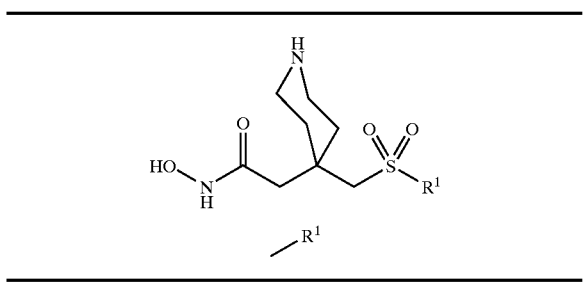
—R¹
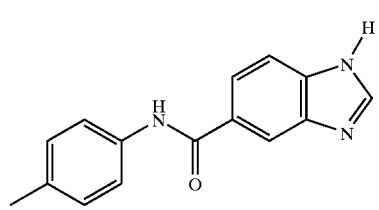
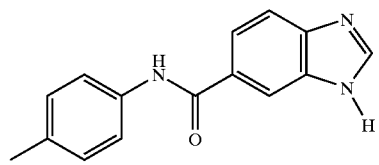
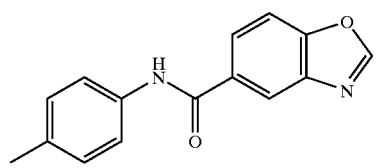
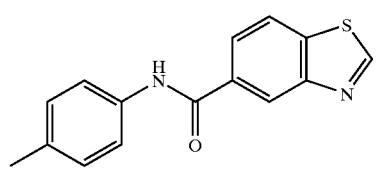
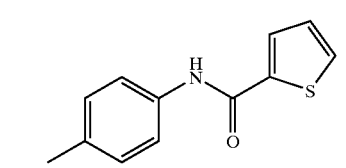
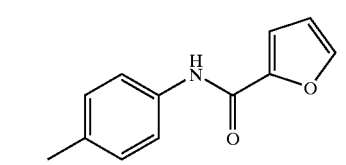
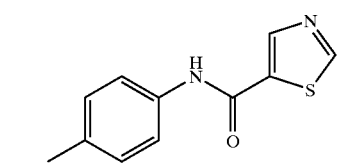
TABLE 29-continued
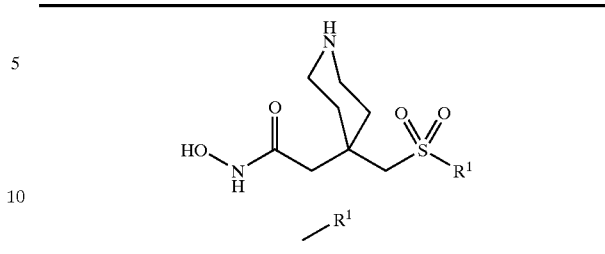
—R¹
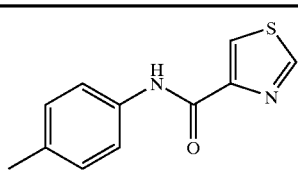
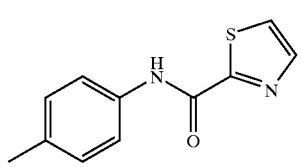
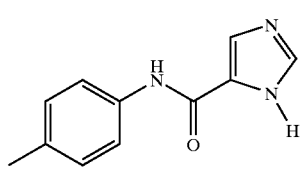
TABLE 30
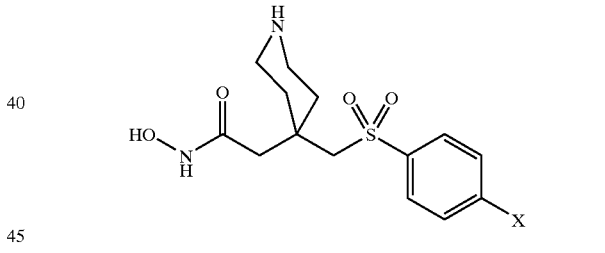
| Example | X |
|---|---|
| 1 | 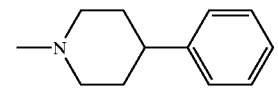 |
| 2 | 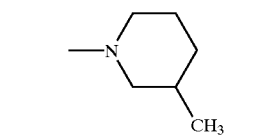 |
| 3 | 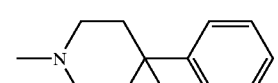 |
| 4 | 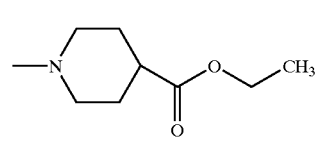 |

TABLE 30-continued

[Structure: piperidine-NH containing compound with hydroxamic acid (HO-NH-C(=O)-CH2-) and sulfonyl-phenyl-X group]

| Example | X |
|---------|---|
| 5 | 1-methylpiperidine-4-carboxamide (N-methyl piperidine with C(=O)NH2 at 4-position) |
| 6 | 1-methylpiperidine-3-carboxamide |
| 7 | 8-methyl-1,4-dioxa-8-azaspiro[4.5]decane |
| 8 | 4-methylmorpholine (N-methyl morpholine) |
| 9 | 1,3,5-trimethylpiperidine (1-methyl-3,5-dimethylpiperidine) |
| 10 | 1-methylpiperazine (with NH) |
| 11 | 1-methyl-4-phenylpiperazine |
| 12 | 1-methyl-4-(4-acetylphenyl)piperazine |
| 13 | 1-methyl-4-(3-trifluoromethylphenyl)piperazine |
| 14 | 1-methyl-4-(4-fluorophenyl)piperazine |

TABLE 30-continued

[Same core structure]

| Example | X |
|---------|---|
| 15 | 1-methyl-4-(4-nitrophenyl)piperazine |
| 16 | 1-methyl-4-(3-fluorophenyl)piperazine |

TABLE 31

[Same core structure]

| Example | X |
|---------|---|
| 1 | 1-methylpiperidine-4-carboxylic acid N-ethyl amide |
| 2 | 1-methylpiperidine-3-carboxylic acid N-methyl amide |
| 3 | 1-methylpiperidine-3-carbonyl morpholine |
| 4 | 1-methylpiperidine-4-carbonyl-glycine (amide to CH2COOH) |

TABLE 31-continued
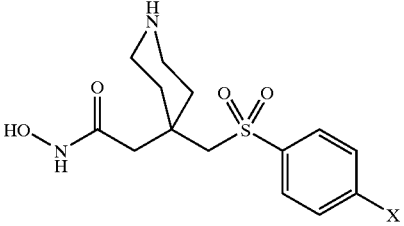
| Example | X |
|---|---|
| 5 | 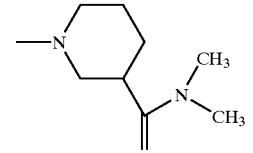 |
| 6 | 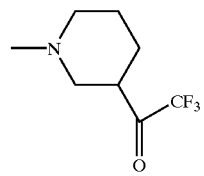 |
| 7 | 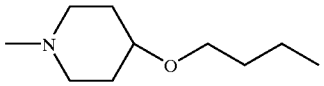 |
| 8 | 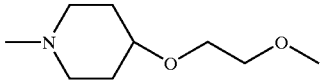 |
| 9 | 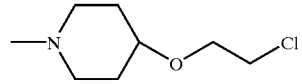 |
| 10 | 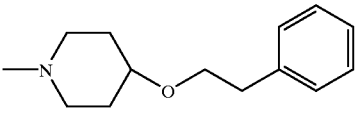 |
| 11 | 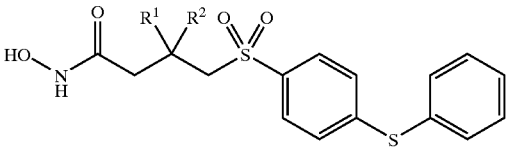 |
TABLE 32
| Example | R$^1$ | R$^2$ |
|---|---|---|
| 1 | —H | —H |
| 2 | —H | —CH$_3$ |
| 3 | —CH$_3$ | —CH$_3$ |
| 4 | —H | —OH |
TABLE 32-continued
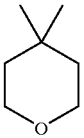
| Example | R$^1$ | R$^2$ |
|---|---|---|
| 5 | —CH$_3$ | —OH |
| 6 | —CH$_3$ | —NH$_2$ |
| 7 | 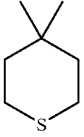 | |
| 8 | 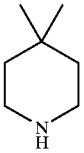 | |
| 9 | 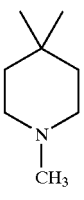 | |
| 10 | 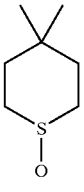 | |
| 11 | 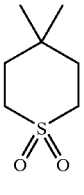 | |
| 12 | | |
| 13 | | |

TABLE 32-continued

Structure: hydroxamic acid–CH2–C(R1)(R2)–CH2–S(O)2–C6H4–S–C6H5

| Example | R1 | R2 |
|---------|----|----|
| 14 | CH3 | 4,4-dimethylpiperidin-1-yl with N-cyclopropyl |
| 15 | CH3 | 4,4-dimethylpiperidin-1-yl with N-CH2-C≡CH (propargyl) |
| 16 | CH3 | 4,4-dimethylpiperidin-1-yl with N-isopropyl (CH(CH3)2) |
| 17 | CH3 | 4,4-dimethylpiperidin-1-yl with N-C(O)CH3 (acetyl) |
| 18 | CH3 | 4,4-dimethylpiperidin-1-yl with N-S(O)2CH3 (methanesulfonyl) |
| 19 | CH3 | 4,4-dimethylpiperidin-1-yl with N-CH2C(O)NH2 |
| 20 | CH3 | 4,4-dimethylpiperidin-1-yl with N-CH2C(O)OCH3 |
| 21 | CH3 | 4,4-dimethylpiperidin-1-yl with N-CH2C(O)NHCH3 |
| 22 | CH3 | 4,4-dimethylpiperidin-1-yl with N-CH2C(O)OH |

TABLE 33

Structure: hydroxamic acid–CH2–CH(R1)–CH2–S(O)2–C6H4–O–C6H5

| Example | —R1 |
|---------|-----|
| 1 | —CH2—O—CH2—C6H5 (benzyloxymethyl) |
| 2 | —CH2—O—CH2-(pyridin-2-yl) |

TABLE 33-continued
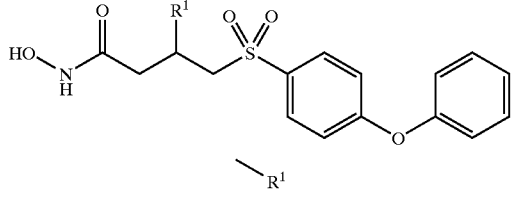
| Example | —R[1] |
|---|---|
| 3 | 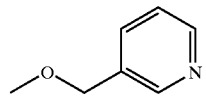 |
| 4 | 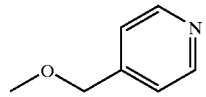 |
| 5 | 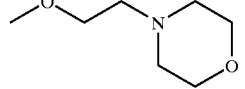 |
| 6 | 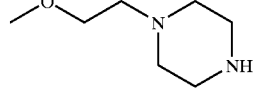 |
| 7 | 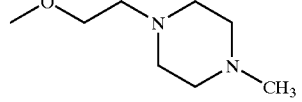 |
| 8 | 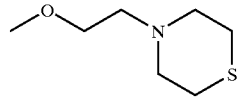 |
| 9 | 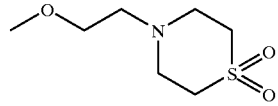 |
| 10 | 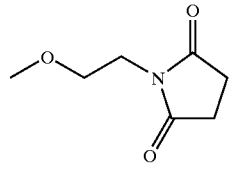 |
| 11 | 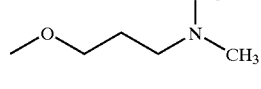 |
| 12 | 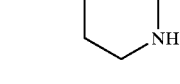 |
| 13 | 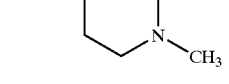 |
TABLE 33-continued
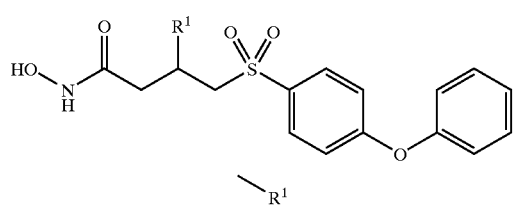
| Example | —R[1] |
|---|---|
| 14 | 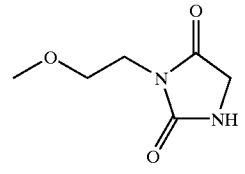 |
| 15 | 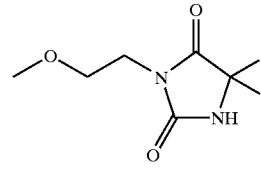 |
TABLE 34
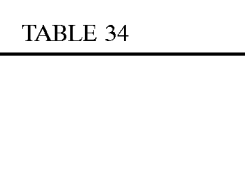
| —R[14] |
|---|
| 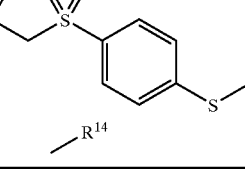 |
| 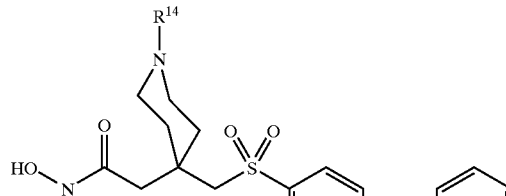 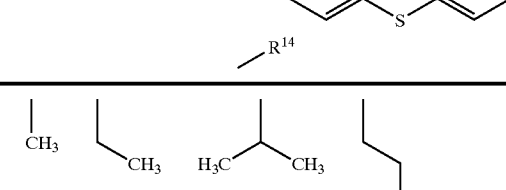 |
| 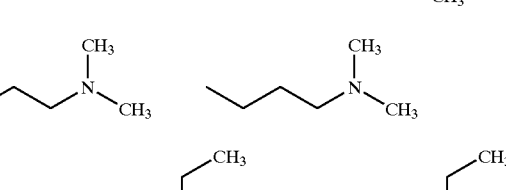 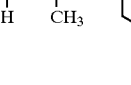 |
| 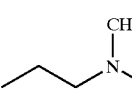 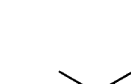 |

TABLE 34-continued
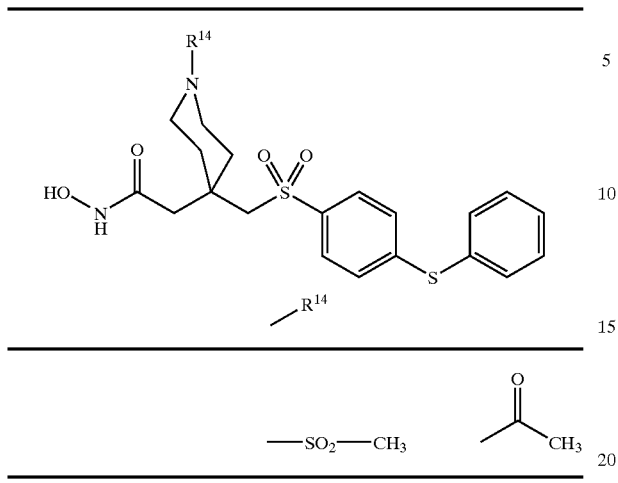
| | |
|---|---|
| —SO₂—CH₃ | (acetone) |
TABLE 35
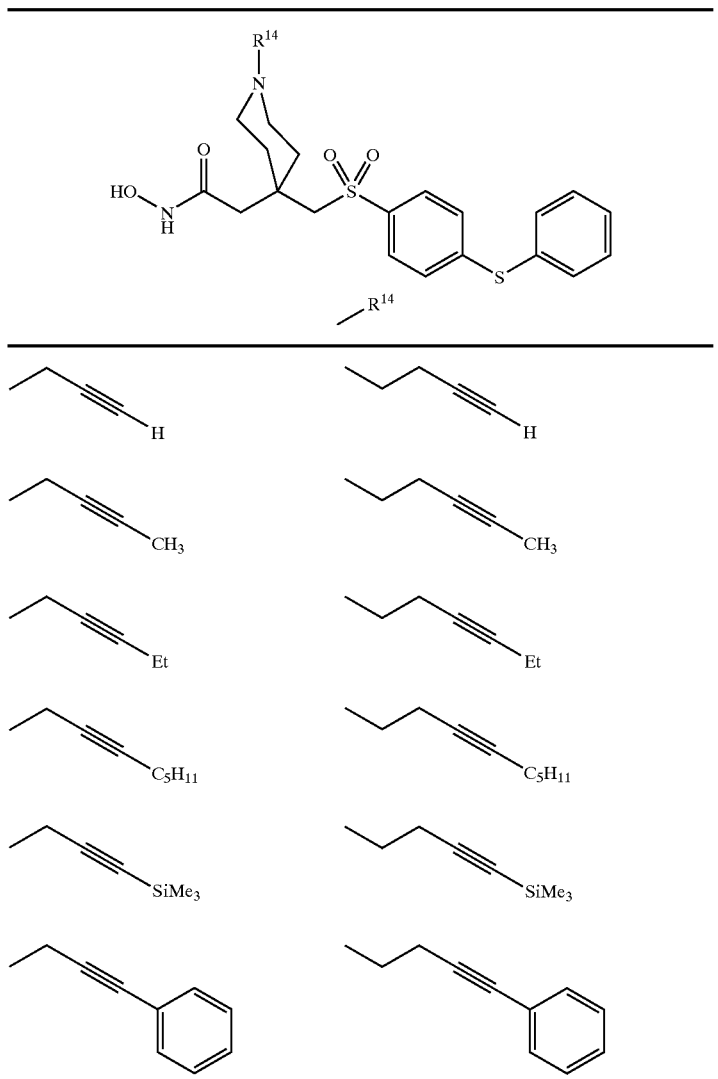

TABLE 35-continued
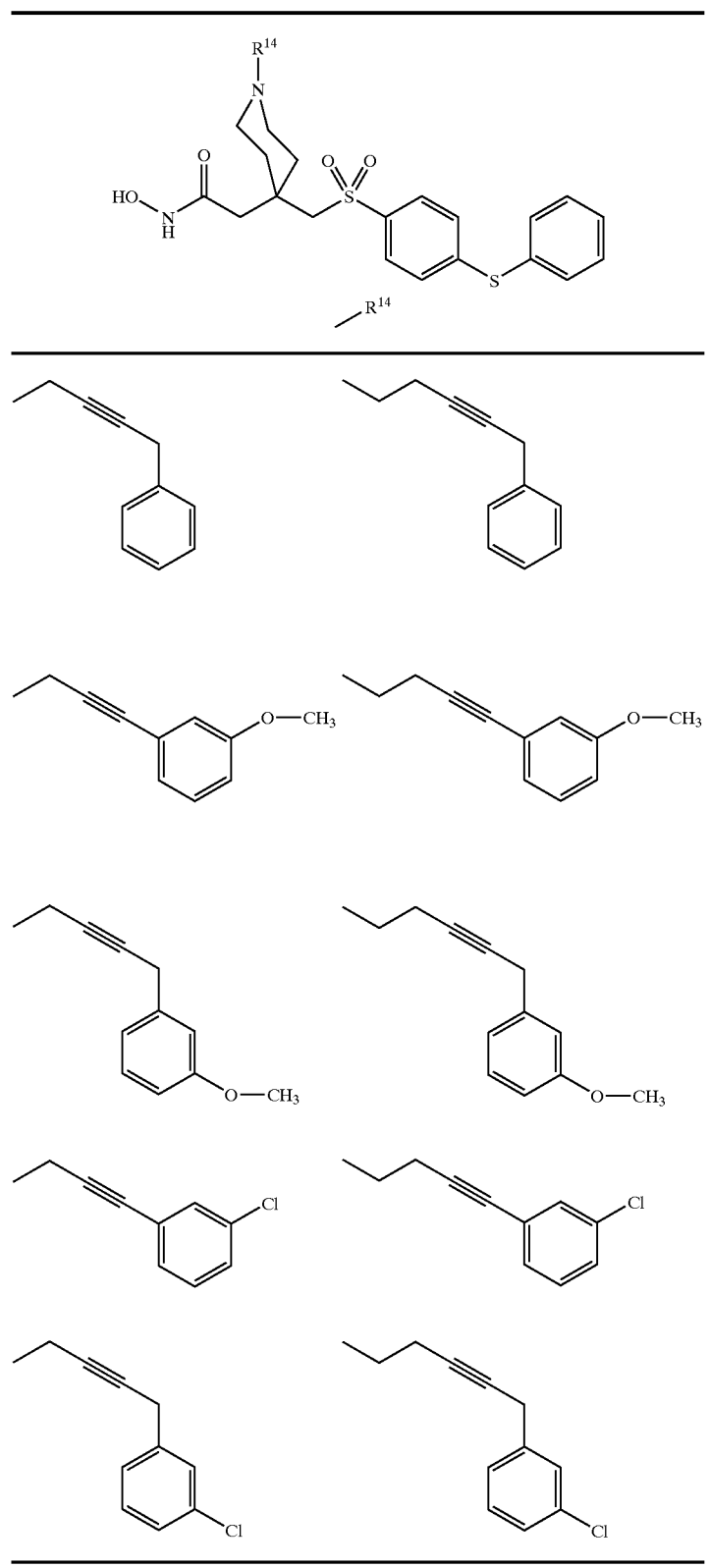

TABLE 36
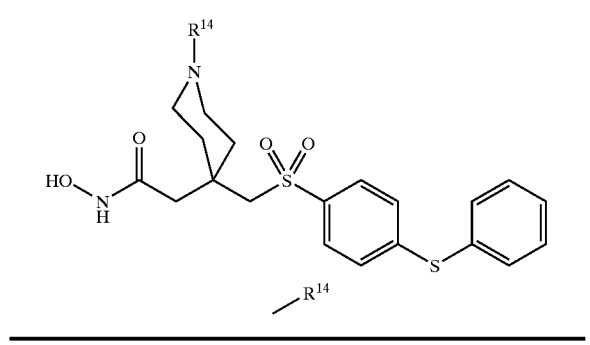
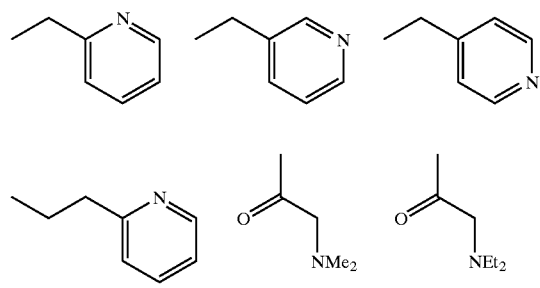
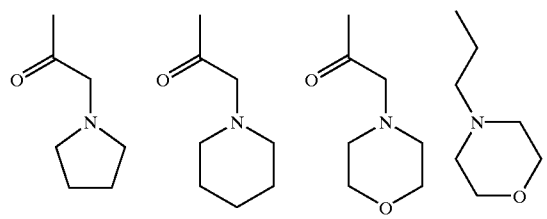
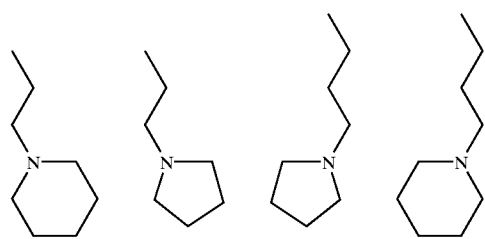
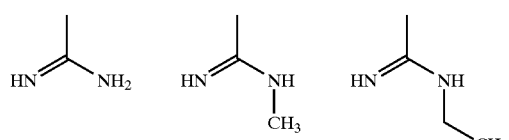
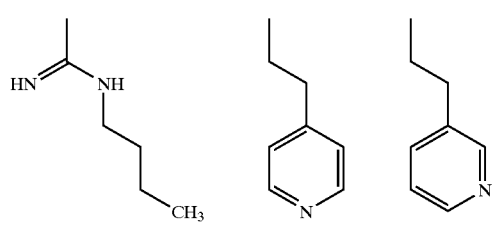
TABLE 36-continued
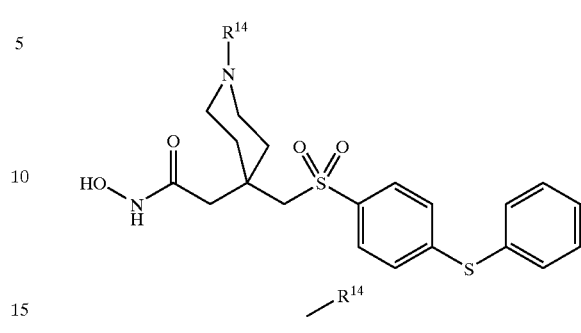
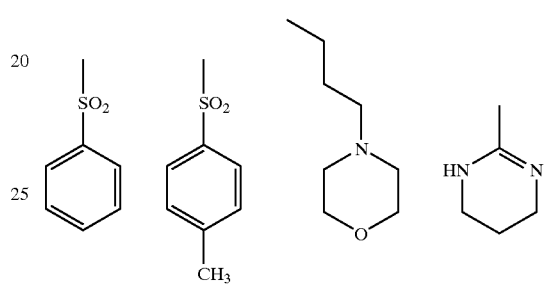
TABLE 37
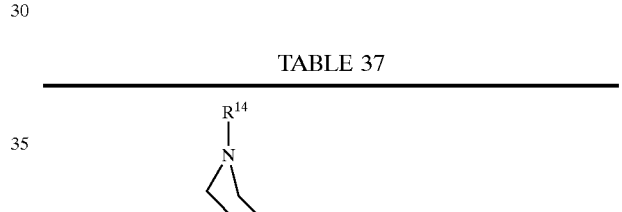
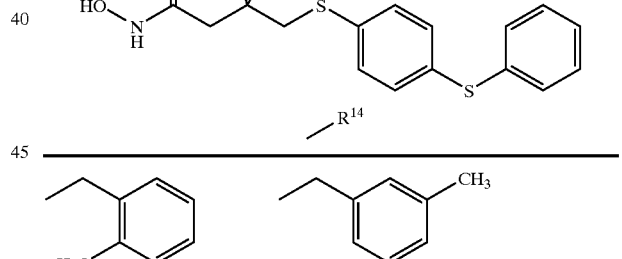
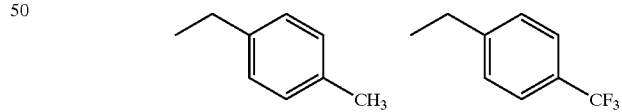
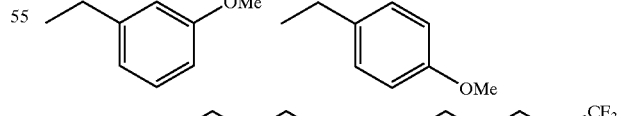
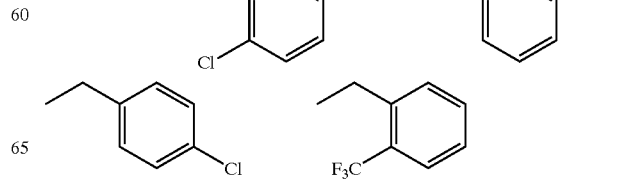

TABLE 37-continued

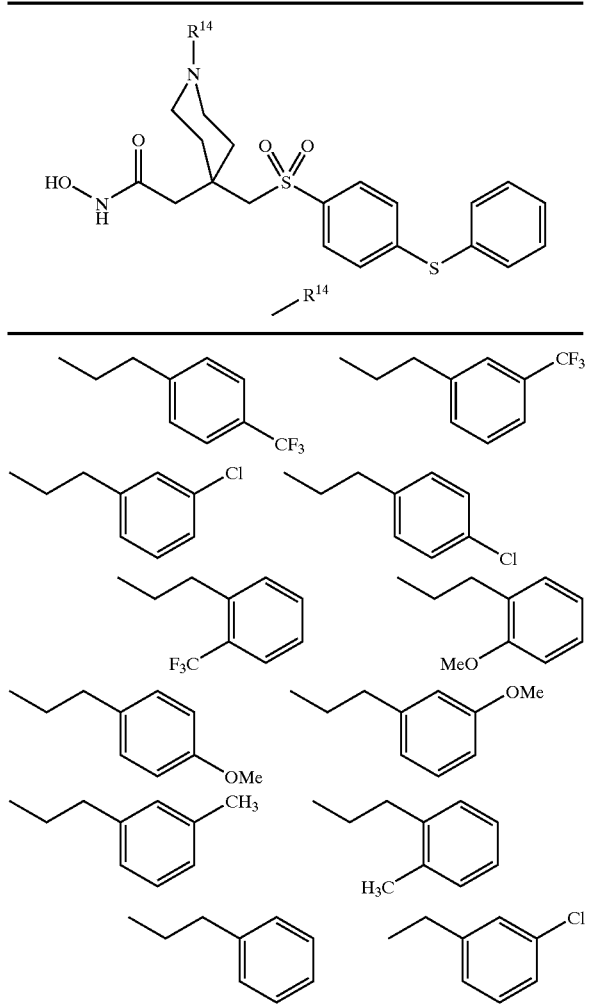

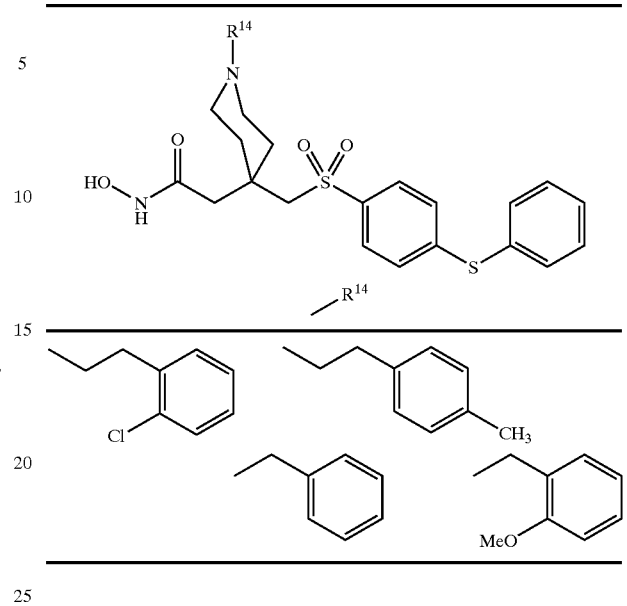

Preparation of Useful Compounds

Compounds of the invention can be produced in accordance with the following generic synthetic Schemes A-D. It is noted that the numbers shown on R groups these schemes, except in Scheme D, are different from those utilized in structural formulas having Roman numerals. That difference in numbering is to illustrate the generality of these synthesis schemes. Specific synthetic schemes that illustrate the preparation of specific compounds follow hereinafter.

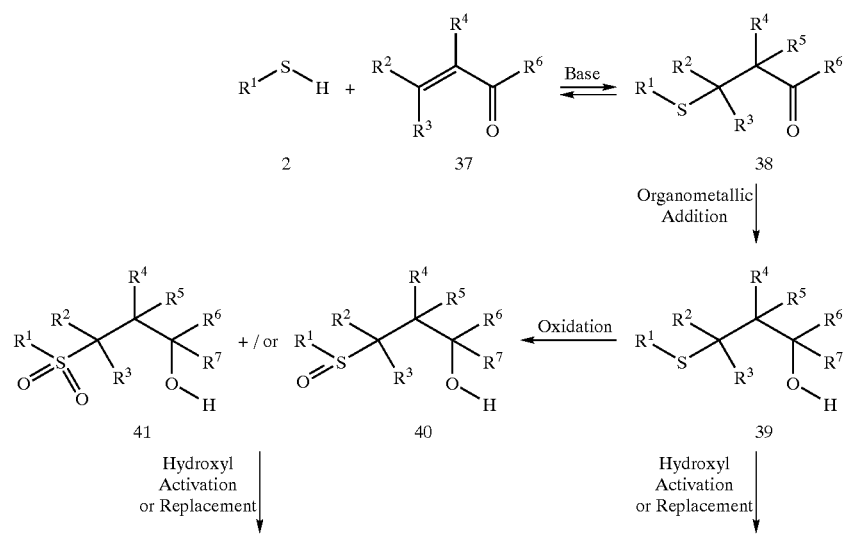

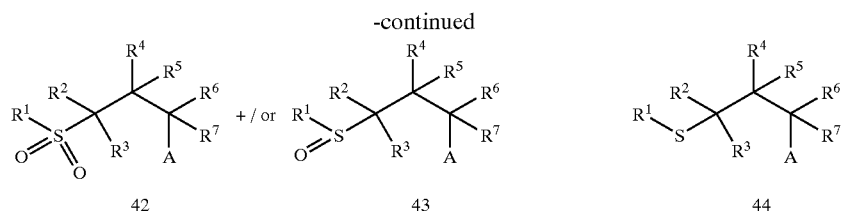
Where A is Cl, Br, I, Tosylate (Ts), Mesylate (Ms), Triflate and the like.
SCHEME B
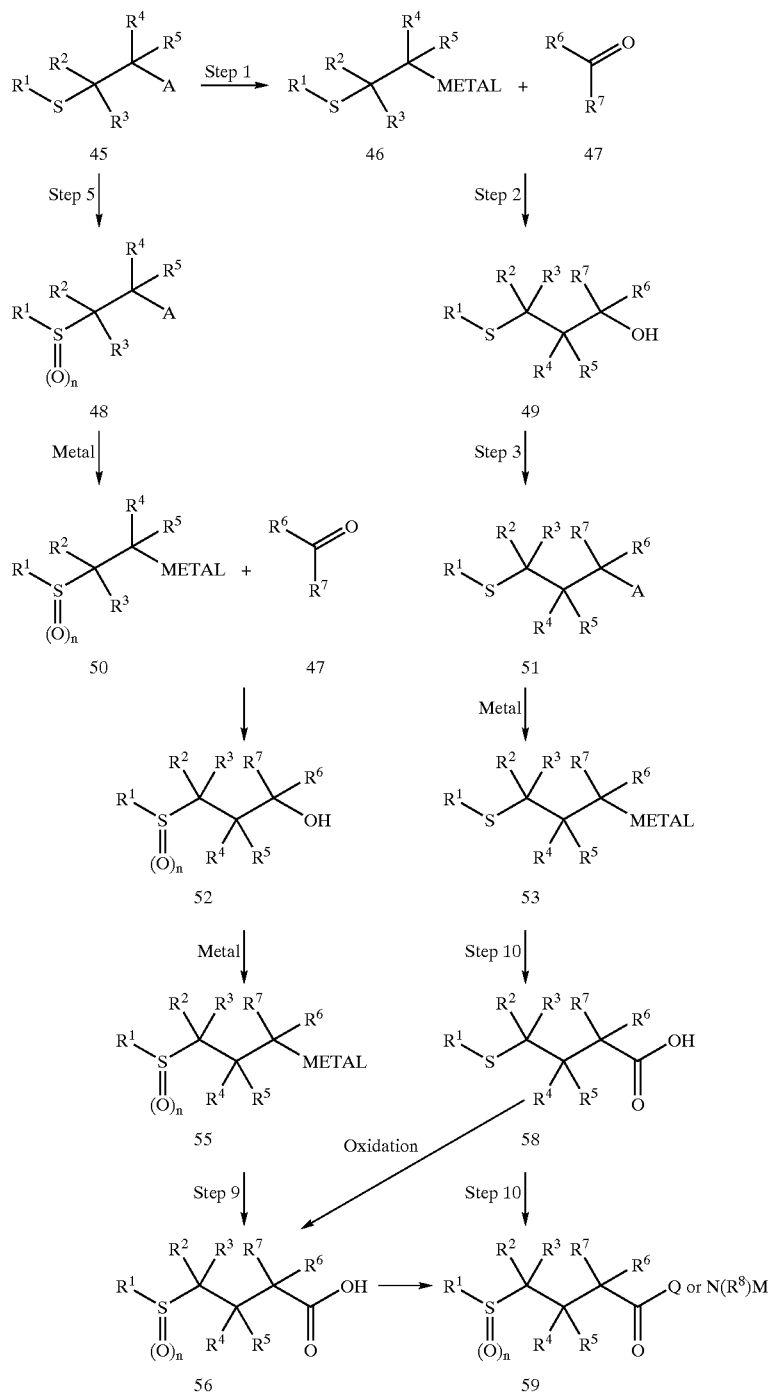

A = Cl, Br, I, Tosylate, Mesylate, Triflate and the like.
n = 0, 1, 2
Q = Alkoxy, Arylalkoxy, H, OH, Amino
M = H, Arylalkyl, Cycloalkoxyalkyl -continued

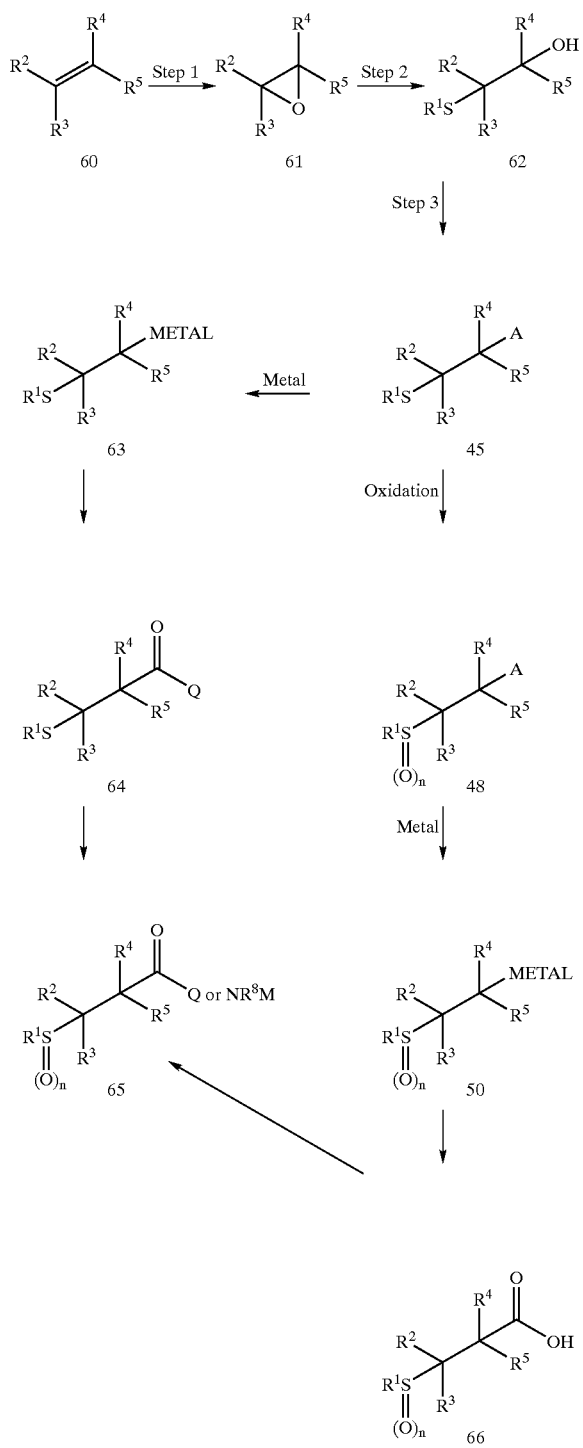

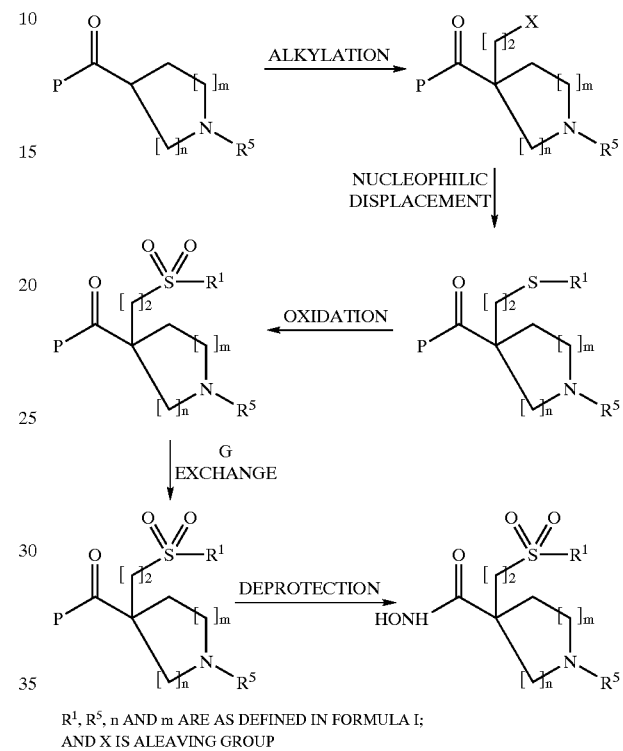

$R^1$, $R^5$, n AND m ARE AS DEFINED IN FORMULA I;
AND X IS A LEAVING GROUP

A = Cl, Br, I, Tosylate, Mesylate, Triflate and the like.
n = 0, 1, 2
Q = Alkoxy, Arylalkoxy, H, OH, Amino
M = H, Arylalkyl, Cycloalkoxyalkyl The above syntheses, as with all of the reactions discussed herein, can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolyses, can be carried out under laboratory air.

The compounds of this invention are described above. This description includes 4-sulfonehydroxamates and hydroxamate derivatives as defined wherein 4 refers to the position of the sulfonyl group removed from the carbonyl group of the hydroxamic acid group. The placement of that sulfur can also shown by using the terms alpha ( ), beta ( ), gamma ( ) or omega ( ) wherein alpha is the 2-position relative to the carboxyl or carboxyl derivative carbonyl, beta is the 3- position relative to the carboxyl or carboxyl derivative carbonyl, gamma is the 4- position relative to the carboxyl or carboxyl derivative carbonyl and omega is the last position relative to the carboxyl or carboxyl derivative. Omega is a general term that denotes the last position in a chain without regard to the length of the chain.-

As non-limiting examples, oxidations, reductions, organometallic additions, hydrolyses, $SN_2$ reactions, conjugate additions, carbonyl additions, aromatic displacements and the like can be included. A person skilled in the art can apply the reactions to these compounds or readily adapt or change synthetic procedures to a specific example as required.

In general, the choices of starting material and reaction conditions can vary as is well know to those skilled in the art. Usually, no single set of conditions is limiting because variations can be applied as required and selected by one skilled in the art. Conditions can also be selected as desired to suit a specific purpose such as small scale preparations or large scale preparations. In either case, the use of less safe or less environmentally sound materials or reagents is usually be minimized. Examples of such less desirable materials are diazomethane, diethyl ether, heavy metal salts, dimethyl sulfide, chloroform, benzene and the like.

Various reactions illustrated in the above Schemes can be base mediated by the use of catalytic amounts of some bases or carried out with an equivalent or more of a base by the addition of an additional reagent or the thiol reagent can be a preformed thiol salt such as the sodium salt of a thiophenol. Bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides.

As non-limiting examples, such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine and the like. Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzylmethyldiisopropyl ammonium hydroxide, methyldiazabicyclononyl ammonium hydroxide, methyltribenzyl ammonium hydroxide, N,N-dimethylmorpholinium hydroxide, N,N,N', N',-tetramethylpiperazenium hydroxide, and N-ethyl-N'-hexylpiperidinium hydroxide and the like.

Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like may also be suitable reagents. Organometallic deprotonating agents such as alkyl or aryl lithium reagents such as methyl, phenyl or butyl lithium, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents.

The reaction media can comprise a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like.

Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like. Room temperature or less or moderate warming (−10° C. to 60° C.) are the preferred temperatures of the reaction. If desired, the reaction temperature might be about −76° C. to the reflux point of the reaction solvent or solvents.

An intermediate thioether can be oxidized to the sulfone in one step using two equivalents to oxidizing agent. Reagents for this process can, in a non-limiting example, include peroxymonosulfate (OXONE®), hydrogen peroxide, meta-chloroperbenzoic acid, perbenzoic acid, peracetic acid, perlactic acid, tert-butyl peroxide, tert-butyl hydroperoxide, tert-butyl hypochlorite, sodium hypochlorite, hypochlorus acid, sodium meta-peroiodate, periodic acid and the like. Protic, non-protic, dipolar aprotic solvents, either pure or mixed, can be chosen, for example, methanol/water.

The oxidation can be carried out at temperature of about −78° to about 50° degrees centigrade and normally selected from a range −10° C. to about 40° C. Preparation of a desired sulfone can be carried out in a two-step process using about one equivalent of oxidizing agent to first form the sulfoxide at about 0° C. A second oxidation then pproduces the sulfone.

The solvents listed above can be used with these selective oxidations with, for example, methanol or methanol/water being preferred along with a temperature of from about −10° C. to 30° C. It can be desirable in the case of more active oxidizing agents, but not required, that the reactions be carried out under an inert gas atmosphere with or without degassed solvents.

A hydroxamate can be prepared from the corresponding ester by reaction of the ester with one or more equivalents of hydroxylamine hydrochloride at room temperature or above in a solvent or solvents such as those listed above. This exchange process can be further catalyzed by the addition of additional acid.

Alternatively, a base such as a salt of an alcohol used as a solvent, for example, sodium methoxide in methanol, can be used to form hydroxylamine in situ which can exchange with an ester or amide. The exchange can be carried out with a protected hydroxyl amine such as tetrahydropyranylhydroxyamine (THPONH$_2$), benzylhydroxylamine (BnONH$_2$), and the like in which case compounds in which the ester is a tetrahydropyranyl (THP) or benzyl (Bn) ester.

Removal of the protecting groups when desired, for example, following further transformations in another part of the molecule or following storage, is accomplished by standard methods well known in the art such as acid hydrolysis of the THP group or reductive removal of the benzyl group with hydrogen and a metal catalyst such as palladium, platinum, palladium on carbon or nickel.

Oxidizable functional groups are readily recognized by those skilled in the art and alternative synthesis can be used such as the protection/deprotection sequence.

Acids can be converted into activated carbonyl compounds using reagents well know in the art including the peptide and protein synthesis and amino acid coupling or conjugation art. Examples of such reagents are thionyl chloride, oxalyl chloride, phosphorus oxychloride, HOBT, isobutylchloroformate an the like. These valuable activated carbonyl intermediates can then be transformed into hydroxamic acids or hydroxamic acid derivatives such as H, benzyl or THP. Preparation of or interconversion between the hydroxylamine or hydroxylamine derivative compounds or acids or amides or esters can be carried out by one skilled in the art using the methods discussed above or by other techniques.

The amine function in the intermediate compounds use a protecting group to facilitate the transformations. Decisions involving the selection of protecting groups and their use can be made by a person skilled in the art. Especially useful are the techniques and reagents used in protein, peptide and amino acid coupling and transformation chemistry. The use of the tert-butoxycarbonyl (BOC), benzyloxycarbonyl (Z) and N,N-dibenzyl groups as will as their synthesis and removal are examples of such protection schemes.

Coupling of the amino acids, amino esters, amino acid hydroxamates or hydroxamate derivatives and amino acid amides of the precursor (intermediate) compounds with, for example, other amino acids, amines, alcohols, amides or acids is also carried out by methods well known in the art such as, for example, active ester or mixed anhydride couplings with preferred bases if required being moderate tertiary amines such as N-methylmorpholine. Removal of a preexisting group that can also serve as a protecting group or blocking group such as the acetyl group and the like is also accomplished using standard hydrolysis conditions such as base hydrolysis or exchange or acid exchange or hydrolysis.

In the case of compounds with an amine group, it is sometimes desirable to use acidic conditions with a reagent such as hydrogen peroxide and/or in combination with an acidic reagent such as periodic acid, peracetic acid and the like. It should also be noted by one skilled in the art that hydrolysis or exchange of the acetyl group may or may not effect hydrolysis or exchange of a ester, amide or hydroxamate function.

Preparation of yet another class of compounds of this invention, those containing the alpha-hydroxy carbonyl function, typically uses the SN$_2$ class of reactions. A bimolecular nucleophilic displacement (SN$_2$) reaction is illustrated in a step wherein a halogen is displaced by a thiol compound or the salt of a thiol compound. The thiol anion can be derived from a preformed salt or the salt can be formed in situ via addition of a base.

Preferred bases are those that are hindered such that competition with thiolate anion in a two stage reaction is minimized. The solvents, solvent mixtures or solvent/reagent mixtures discussed are satisfactory but non-protic or dipolar aprotic solvents such as acetone, acetonitrile, DMF and the like are examples of a preferred class.

A protecting group P on the alpha-hydroxy group canalso be utilized. Such protecting groups can include acyl groups, carbamoyl groups, ethers, alkoxyalkyl ethers, cycloalkyloxy ethers, arylalkyl groups trisubstituted silyl groups and the like. Examples of such protecting groups include acetyl, THP, Benzyl, Z, tert-butyldimethylsilyl (TBDMS) groups. The preparation of such protected alcohols as well as the removal of the protecting groups is well known in the art and its practitioners.

The selection of an atmosphere for the reactions of these Schemes as well as the other Schemes depends, as usual, a number of variables known to those skilled in the art. The choices can be an inert atmosphere such as nitrogen, argon, helium and the like or normal or dry air. Preferred is the use of an inert atmosphere if there is an uncertantity as to the requirements of the process.

One of these variables particularly requiring the attention of the skilled person is control of oxidation by air or another means of a thiol or the salt of a thiol to its corresponding disulfide or mixed disulfide. The used of a damp atmosphere while carrying out an organometallic compound requiring synthesis not desirable for either economic or safety reasons whereas the use of air is normal for aqueous hydrolysis or exchange reactions where oxidation, for example, is not probable.

Addition of an organometallic reagent such as a Grignard Reagent, lithium organometallic reagent, zinc organometallic reagent, cadium organometallic reagent, sodium organometallic reagent or potassium organometallic regent to a carbonyl group such as an aldehyde, ketone, ester, amide (primaryl, secondary, tertiary), acid chloride, anhydride, mixed anhydride, hydroxamate derivative (mono- or bis-), carbonate, carbamate or carbon dioxide is illustrated in the Schemes such as Schemes A, B and C. The products of such reactions of organometallic compounds with carbonyl compounds are well known to those skilled in the art. Well know examples include the preparation of alcohols by reaction with aldehydes, acids by reaction with carbon dioxide and esters by reaction with carbonate esters.

For example, in Scheme A, the product of such a reaction can be an alcohol such as compound 39 or an ester, amide, ketone or aldehyde. It is also recognized by those skilled in the art that the carbonyl compound and the organometallic compound can be exchanged or interchanged or otherwise manipulated to synthesize the same or a similar compound. For example, although not contemplated herein, carbonyl compound 38 in Scheme A wherein R$^6$ is methyl (or ethyl) can be reacted with ethyl magnesium bromide (or methyl magnesium bromide) to form compound 39 where R$^7$ is ethyl (or methyl) and organometallic compound 53 in Scheme B where one of R$^7$ and R$^6$ is methyl one is ethyl can be treated with water to also form compound 39.

An alcohol can also be converted into a halogen or sulfonate ester. Either product, as shown with the sulfides, can be oxidized or, once oxidized, reduced back to a sulfide or sulfoxide. In addition, the alcohol with the sulfur oxidized can also be converted into, for example, its corresponding halogen or sulfonated ester.

The halogen compounds such as those in Schemes A, B and C, for example, with or without the sulfur oxidized can be reacted with a metal to form an organometallic reagent such as those listed above. The organometallic compound can then be reacted with a carbon-oxygen double bond-containing molecule to produce precursors to compounds of this invention including homologous acids, esters, amides (primary, secondary, tertiary), ketones, aldehydes and the like.

If the product of the reaction of an organometallic compound with a carbonyl compound is itself another carbonyl containing compound such as shown, for example, by the synthesis of compounds 64 or 65 in Scheme C, the product can be either a metalloprotease inhibiting product of this invention or an intermediate for the synthesis of a homologous metalloprotease inhibiting compound of this invention. As was discussed above with respect to alcohols and illustrated in these Schemes, these carbonyl products can be oxidized at sulfur before or after further modification.

A lactone ring where $R^2$ through $R^7$ inclusive are as defined above can be opened with a thiolate anion to provide a 4-thia acid (omega-thia acid, gamma-thia acid) or salt. An example of a preferred thiol is 4-phenoxybenzenethiol. The sulfide formed can them be oxidized to the corresponding sulfone, converted to the hydroxamate or protected hydroxamate, deprotected if required all by methods discussed and illustrated above and known in the art.

Alternatively, a Lewis acid in the presence of a thiol can be used to form the thia acid. Opening of the lactone with a Lewis such as zinc bromide or zinc chloride in the presence of thionyl bromide or thionyl chloride can provide an omega-halo acid halide (activated carbonyl). This intermediate derivatives as desired at the carbonyl carbon can be prepared to provide a protected carbonyl compounds such as an ester or an amide or used to form a hydroxamic acid or protected hydroxamic acid directly; i.e., a omega-halo ester, amide, hydroxamic acid or protected hydroxamate.

The 4-chloro or 4-bromo group can be displaced via a nucleophilic substitution reaction ($SN_2$) using a —$SR^1$ reagent to provide a thia-compound that can then be oxidized as outlined above to provide a desired compound. Preferred lactones can include 2-methylbutyrolactone, 2-hydroxy-3,3-dimethylbutyrolactone and 2-piperidylbutyrolactone. Preferred omega-haloesters include, methyl 2,2-dimehyl-4 chlorobutyrate and ethyl 4-bromobutyrate.

Alpha-halolactones can be utilized in the preparation of compounds of this invention wherein the alpha-carbon of the product hydroxamic acids are substituted with a nucleophile such as a hydroxyl, ether, azide or an amine. These intermediates, when stable to the reaction conditions, properly protected or converted in a later step to the desired function can provide substrates for the lactone dependant reactions discussed above. Bromobutyrolactone is a preferred halolactone.

Compounds of this invention can be prepared by alkylation of a carbanion (nucleophile) generated from a protected carboxylic acid using processes known in the art. Protecting groups for the carboxyl function include, for example, esters such as tert-butyl esters. Bases for forming the anion are can be organometallic reagents such as tert-butyl lithium, metal amides such as lithium diisopopyl amide (LDA) or alkoxides such as potassium tert-butoxide. Other candidate bases are discussed above.

Following or during formation of the anion, the alkylating agent (electrophile) is added which undergoes a nucleophilic substitution reaction. Electrophilic substrates for displacement can include, for example, dihalo alkanes such as 1,2-dihaloalkanes or mono-halo-mono sulfated alkanes or bissulfonate alkane esters. 1,2-di-Bromoethanes, 1-chloro-2, bromoethanes, 1-chloro-2-tosylethanes and 1,2-ditoluenesulfonylethanes are examples of such bis-electrophiles. 1-Bromo-2-chloro-ethane is a preferred electrophile.

Activated ester groups are well known in the art and can include, for example, di-easters such as malonates, ester-ketones such as acetoacetic esters or ester-aldehydes that are subject to carbonyl addition reactions. Alkylation with one equivalent of alkyating agent followed by derivatization of the new omega carbonyl group with, for example, an organometallic reagent or reduction to form an alcohol which can then be derivatized to form a carbon halogen bonds or an activated ester such as a sulfate ester. These omega-substituted compounds can serve as substrates for the thioate displacement and oxidation reactions discussed above to form the carboxylic acid compounds or intermediates of this invention.

Omega-haloalcohols can be useful starting materials for the preparation of compounds of this invention using alternative synthetic sequences from those discussed above. They can serve as substrates for $R^1$ thiolate displacement ($SN_2$) to provide 4-sulfides (thio ethers) which can then be oxidized to the desired sulfones. The HS-$R^1$ compounds can be prepared as discussed below and oxidized as discussed above. Preparation of the $R^1$ group can be via an intermediate such as a fluorothiophenol followed by displacement of the fluoride with a second nucleophile to produce compounds or intermediates of this invention. Flourothiophenol and phenol and 2,3-dimethyl phenol are examples of preferred thiols and phenols, respectively. The sulfone alcohols can be oxidized to the corresponding carboxylic acids as well as to the corresponding aldehydes.

The carboxylic acids or protected carboxylic acids can be utilized as presented herein. The aldehydes can serve as useful intermediates for homologation to an alpha-hydroxysulfone acid compound that can serve as a substrate for preparation of a hydroxamic acid or hydroxamate of this invention. Homologation of an aldehyde can be carried out by adding a cyanide to the aldehyde to form a alpha-cyano-omegasulfone (cyanohydrin) which can then be hydrolysed with an acid such as those discussed above to form a alpha-hydroxy carboxylic acid useful in the synthesis of compounds of this invention. Cyanohydrins can be prepared by methods well known in the art such as treatment of an aldehyde with a metal cyanide, hydrogen cyanide or trimethylsilylcyanide. Trimethylsilylcyanide is a preferred reagent.

The preparation of compounds of this invention based on alpha-oxygen-substituted compounds such as the hydroxyl group is discussed and illustrated and the methods are well known in the art. Protection of the alcohols of this invention or of the intermediate alcohols used in this invention is also well known.

The preparation of ethers can be carried out by forming a salt of the alcohol and treating this nucleophile with an electrophile such as a halide or an activated ester such as a sulfate ester. The salt is formed by treating the alcohol with a base such as is discussed above. Examples of such bases are lithium alkyls, metal hydrides or the metal salts of an amine such as LDA.

Halides can be chlorides, bromides or iodides and sulfates can be, for example, benzene sulfonates, tosylates, mesylates or triflates. An example of a preferred electrophile is 2-chloromethylpyridine and a preferred base is sodium hydride. Alternatively, the alcohol can be converted into a leaving group (electrophilic reagent) and then treated with a nucleophile. Examples of such leaving groups include sulfate esters such tosylates, mesylates and triflates whose preparation is discussed above. The triflate is a preferred leaving group.

Displacement of these groups with nucleophiles is well known in the art and discussed and/or illustrated above. The nucleophiles can be hydroxide to allow inversion of stereochemistry, alkoxides to form ethers, amines or ammonia to form substituted amines or an azide anion to form an azide. A preferred nucleophile the is tetra-(n-butyl) ammonium azide. The azido compound, for example, can be reduced to form the amino acid. Reductions are discussed above and are well known in the art. A preferred method is hydrogenation with palladium on carbon catalyst.

The amines, including the amino acids, of this invention can be acylated or alkylated by methods well known in the art. The amides formed can be considered as protected amines or as end products of this invention. Acylation to form such derivatives as tert-butoxycarbonyl and carbobenzyloxy carbonyl group is discussed above. Other acyl (Ac) groups can be, for example, acetyl, haloacetyl, aroyl, substituted aroyl, heteroaroyl, substituted heteroaroyl or other groups as required. The amines can be acylated using anhydrides, mixed anhydrides, acid chlorides or activated esters. Usually such acylations are carried out in presence of a base such as the bases discussed above and well known in the art. Examples are N-methyl-morpholine, triethylamine and the like.

The carboxyl compounds useful herein having amide substituents can be treated, converted or interconverted as shown and/or dicussed above to form the products of this invention. In addition, the haloacetyl compounds such as the preferred 2-chloroacetamide derivative can be treated with an amine as a nucleophile to yield an aminoacid. Again, these reactions are well known in the art. A preferred amine is morpholine.

The cyclic amino acids used to prepare desired compounds can be prepared in ways know to those skilled in the art. Reduction of heteroaryl or unsaturated or partially unsaturated heterocycles can be carried out. For example, the six membered ring compounds can be synthesized by reduction of the corresponding 2-, 3- or 4-pyridine carboxylic acids, 2-, or 3-pyrazole carboxylic acids or derivatives thereof. The reduction can by hydrogenation in the presence of a catalyst or hydride reduction using a hydride transfer agent such as lithium aluminum hydride. The starting amino acids or their derivatives, such as ethyl isonipecotate, ethyl nipecotate, pipecolinic acid, proline or its isomers, pyroglutamate or its isomers are starting materials that can be used to prepared a compound of this invention.

The R, S and RS isomers of the amino acids can be used. Some starting material can be obtained from commercial sources. A preferred starting material is ethyl isonipecotate.

Alkylation of the aminoacid at the carbon alpha to the carbonyl group to form a useful compound can be carried out by first forming an anion using a base. Exemplary bases are discussed elsewhere. The preferred bases are strong bases that are either hindered and/or non-nucleophilic such as lithium amides, metal hydrides or lithium alkyls. A preferred base is lithium diisopropylamide (LDA) in a dipolar aprotic solvent or THF.

Following or during formation of the anion, an alkylating agent (an electrophile) is added which undergoes a nucleophilic substitution reaction. Non-limiting examples of such alkylating agents are 1,2-dihaloalkanes or haloalkanes also substituted by an activated ester group. Activated ester groups are well known in the art and can include, for example, an ester of a 2-halo-alcohol such as a bromo-, iodo- or chloro-ethane para-toluene sulfonate, triflate or mesylate. A preferred alkylating agents is 1-bromo-2-chloroethane.

The nitrogen substituent on the cyclic aminoacid portion of the compounds of this invention can be varied. In addition, this can be accomplished at different stages in the synthetic sequence based on the needs and objectives of the skilled person preparing the compounds of this invention.

The N-side chain variations can include replacing the hydrogen substituent with a alkyl, arylalkyl, alkene or alkyne. This can be accomplished by methods well known in the art such as alkylation of the amine with an electrophile such as halo- or sulfate ester (activated ester) derivative of the desired sidechain. This can be done in the presence of a base such as those discussed above and in a pure or mixed solvent as discussed above. A preferred base is postassium carbonate and a preferred solvent is DMF.

The alkenes and alkynes can be reduced. if desired, by, for example, hydrogenation with a metal catalyst and hydrogen, to an alkyl or arylalkyl compound of this invention and the alkyne or arylalkyne can be reduced to a alkene of alkane with under catalytic hydrogenation conditions as discussed above dor with an deactivated metal catalyst. Catalysts can include, for example, Pd, Pd on Carbon, Pt, $PtO_2$ and the like. Less robust catalysts include such thing as Pd on $BaCO_3$ or Pd with quinoline or/and sulfur.

An alternative method for alkylation of the amine nitrogen is reductive alkylation. This process, well known in the art, allows treatment of the secondary amine with an aldehyde or ketone in the presence of a reducing agent such as borane, borane:THF, borane:pyridine, lithium aluminum hydride. Alternatively, reductive alkylation can be carried out hydrogenation conditions in the presence of a metal catalyst. Catalysts, hydrogen pressures and temperatures are discussed above and are well known in the art. A preferred reductive alkylation catalyst is borane:pyridine complex.

The compounds of this invention include compounds wherein the substituent on nitrogen of the cyclic amino acids as listed above provide amino acid carbamates. Non-limiting examples of these carbamates are the carbobenzoxycarbonyl (Z, CBZ, benzyloxycarbonyl), isobytoxycarbonyl and tert-butoxycarbonyl (BOC, t-BOC) compounds. These materials can be made, as discussed above, at various stages in the synthesis based on the needs and decisions made by a person skilled in the art using methods well know in the art.

Useful synthetic techniques and reagents include those used in protein, peptide and amino acid synthesis, coupling and transformation chemistry. The use of the tert-butoxycarbonyl (BOC) and benzyloxycarbonyl (Z) as will as their synthesis and removal are examples of such protection or synthesis schemes discussed above. Transformations of amino acids, amino esters, amino acid hydroxamates, amino acid hydroxamate derivatives and amino acid amides of this invention or compounds used in this invention can be carried out as discussed and/or illustrated above. This includes, for example, active ester or mixed anhydride couplings wherein preferred bases, if required, are tertiary amines such as N-methylmorpholine.

Reagents for protection of the amine group of the protected amino acids include carbobenzoxy chloride, iso-butylchloroformate, tert-butoxycarbonyl chloride, di-tert-butyl dicarbonate and the like which are reacted with the amine in non-protic or dipolar aprotic solvents such as DMF or THF or mixtures of solvents. A preferred reagent is di-tert-butyl dicarbonate and a preferred solvent is THF.

Further conversion of the cyclic amino acids of this invention including alkylation, displacement with a thiol or thiolate, oxidation to a sulfone, and conversion into a hydroxamic acid or hydroxamate derivative can be carried out discussed herein.

Sulfone compounds such as those where $R^1$ is nitroaryl can be prepared as compounds of this invention by synthesis of a thiol or thiolate nucleophile, displacement of an electrophile (X) by the nucleophilic thiol or thiolate and oxidation of the product thia ether (sulfide) to the sulfone. For example, displacement of the electrophilic group X with a nitro-benzenethiol can yield a compound where $R^1$ is nitrobenzene that can be reduced to provide a useful amino compound wherein $R^1$ is an aniline. It should be noted that nitrobenzenethiol is an example and not to be considered as limiting or required. Oxidation of the thioether product can be carried out as discussed below when desired.

The reduction of nitro groups to amines is will know in the art with a preferred method being hydrogenation. There is usually a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred. The amino group can be alkylated if desired, or acylated with, for example, an aroyl chloride, heteroaryl chloride or other amine carbonyl forming agent to form an $R^1$ amide.

The amino sulfone or thioether can also be reacted with a carbonic acid ester chloride, a sulfonyl chloride, a carbamoyl chloride or an isocyanate to produce the corresponding carbamate, sulfonamides, or urea. Acylation of amines of this type are well known in the art and the reagents are also well known.

Usually, these reactions are carried out in aprotic solvents under an inert or/and dry atmosphere at about 45° C. to about −10° C. An equivalent of a non-competitive base is usually used with sulfonyl chloride, acid chloride or carbonyl chloride reagents. Following or before this acylation step, synthesis of the hydroxamic acid products of this invention can proceed as discussed.

Other thiol reagents can also be used in the preparation of compounds of this invention. Examples are fluoroaryl, fluoroheteroaryl, azidoaryl or azidoheteroaryl or heteroaryl thiol reagents. These thiols can be used a nucleophiles to as discused above. Oxidation to the corresponding sulfone can then be carried out. The fluoro substituted sulfone can be treated with a nucleophile such as ammonia, a primary amine, a quaternary ammonium or metal azide salt, under pressure if desired, to provide an azido, amino or substituted amino group that can then be reacted an activated benzoic or substituted benzoic acid derivative to form a benzamide. Azides can be reduced to an amino group using, for example, hydrogen with a metal catalyst or metal chelate catalyst or by an activated hydride transfer reagent. Hydrazo compounds can be oxidized to azo compounds and axo compounds can be reduced to hydrazo compounds. The amines can be acylated as discussed above.

Preferred methods of preparing aminethiol intermediates of this invention include protection of an aromatic or heteroaromatic thiol with trityl chloride to form the trityl thiol derivative, treatment of the amine with as reagent such as an aromatic or heteraromatic acid chloride to form the amide, removal ot the trityl group, with acid to form the thiol. Preferred acylating agents include benzoyl chloride and preferred trityl remoing reagents include triflouroacetic acid and trisiopropylsilane.

The fluorine on fluorosulfone intermediates can also be displaced with other aryl or heteroaryl nucleophiles for form compounds of this invention. Examples of such nucleophiles include salts of phenols, thiophenols, —OH group containing aromatic heterocyclic compounds or —SH containing heteroaryl compounds.

Tautomers of such groups azo, hydrazo, —OH or —SH are specifically included as useful isomers. A preferred method of preparing intermediates in the synthesis of the substituted sulfones is by oxidation of an appropriate acetophenone, prepared from a flouroacetophenone, with for example, peroxymonosulfate, to form the corresponding phenol-ether. That phenol-ether is converted into its dimethylthiocarbamoyl derivative using dimethylthiocarbamoyl chloride, followed by rearranging the dimethylthiocarbamoyl derivative with heat to provide the thiol required for preparation of the thioether intermediate.

Salts of the compounds or intermediates of this invention are prepared in the normal fashion wherein acidic compounds are reacted with bases such as those discussed above to produce metal or nitrogen containing cation salts. Basic compounds such as amines can be treated with an acid to for form the amine salt. A preferred amine salt is the hydrochloride salt formed by reaction of the free base with HCl or hydrochloric acid.

Compounds of the present can possess one or more asymmetric carbon atoms and are thus capable of existing in the form of optical isomers as well as in the form of racemic or nonracemic mixtures thereof. The optical isomers can be obtained by resolution of the racemic mixtures according to conventional processes well known in the art, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers.

Still another available method involves synthesis of covalent diastereoisomeric molecules, e.g., esters, amides, acetals, ketals, and the like, by reacting compounds of Formula I with an optically active acid in an activated form, a optically active diol or an optically active isocyanate. The synthesized diastereoisomers can be separated by conventional means such as chromatography, distillation, crystallization or sublimation, and then hydrolyzed to deliver the enantiomericaly pure compound. In some cases hydrolysis to the parent optically active drug is not necessary prior to dosing the patient because the compound can behave as a prodrug. The optically active compounds of Formula I can likewise be obtained by utilizing optically active starting materials.

In addition to the optical isomers or potentially optical isomers discussed above, other types of isomers are specifically intended to be included in this discussion and in this invention. Examples include cis isomers, trans isomers, E isomers, Z isomers, syn- isomers, anti- isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for delivery.

Scheme 1
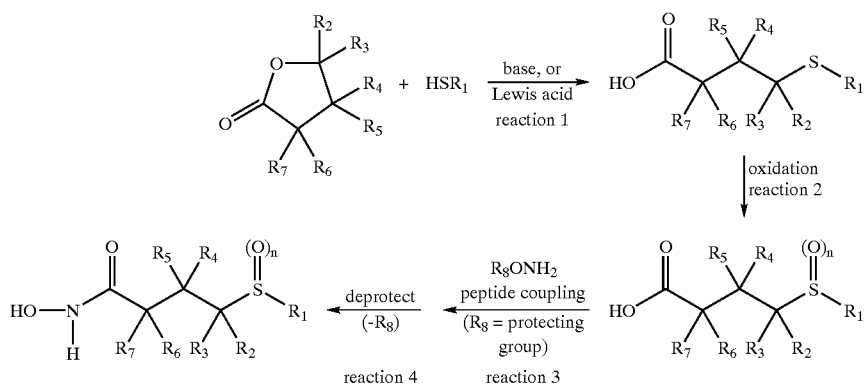
n = 1 or 2
Scheme 2
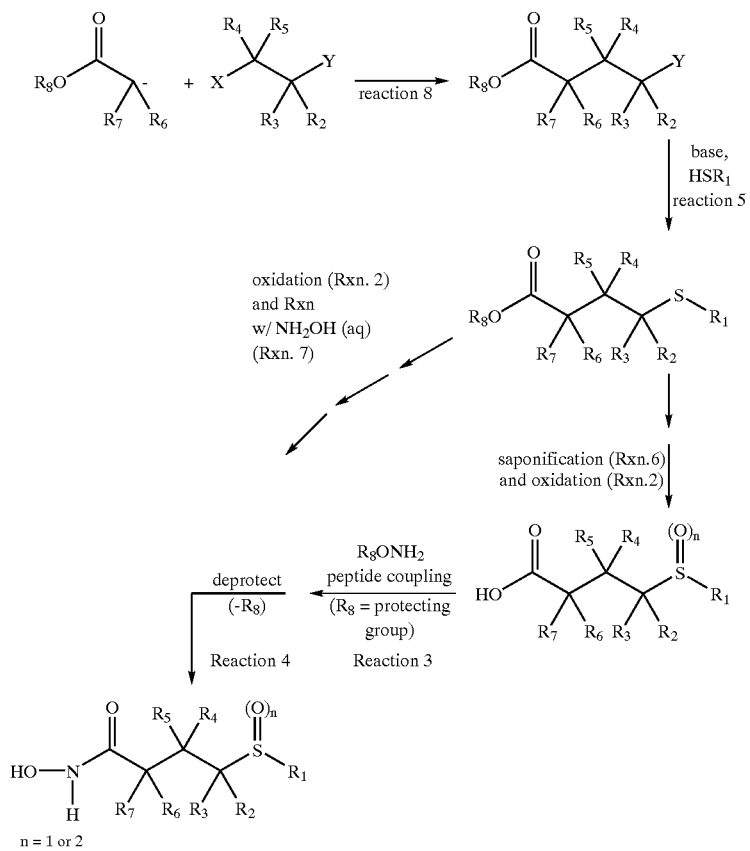
n = 1 or 2
Scheme 3
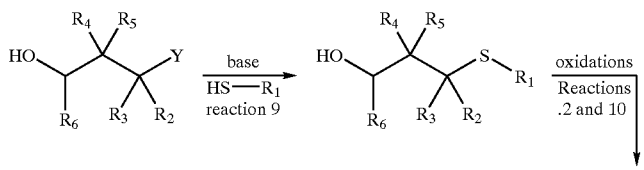

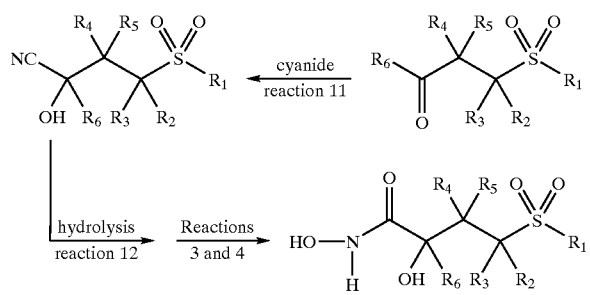
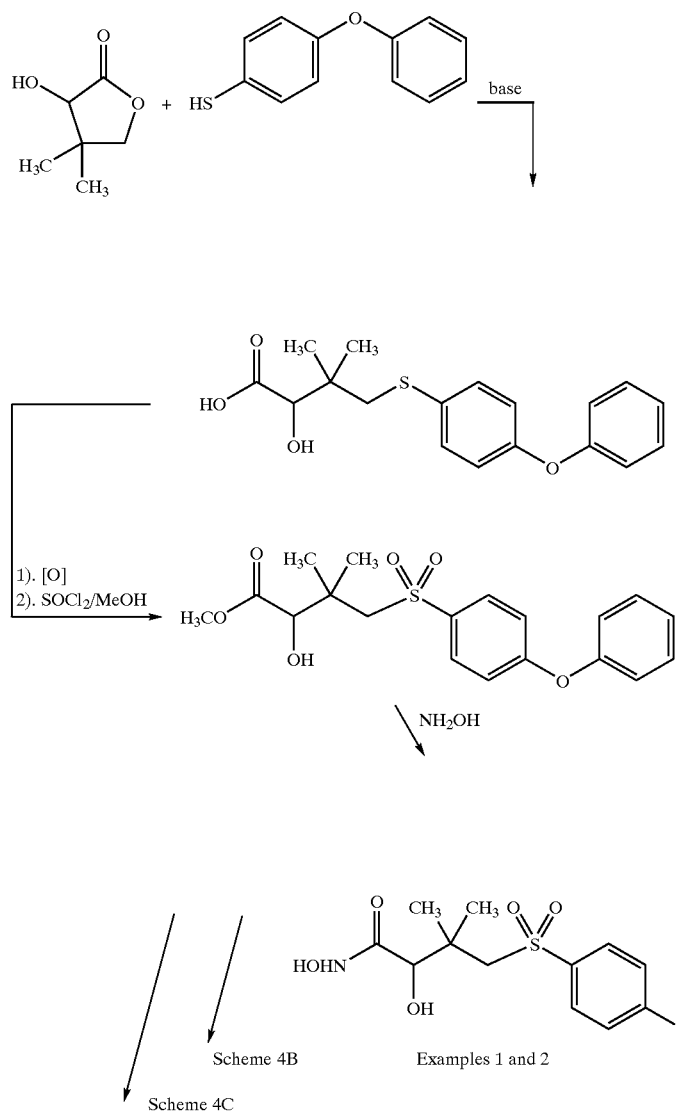

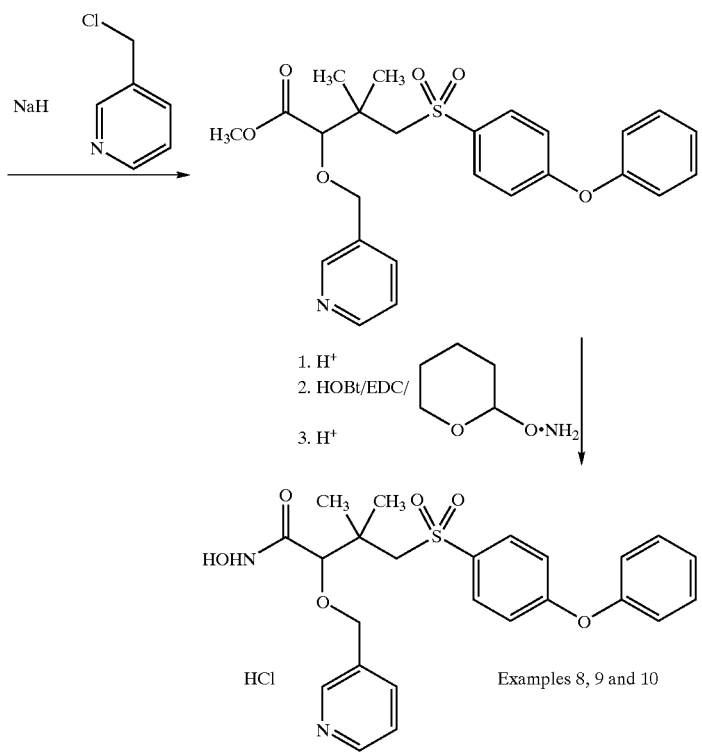
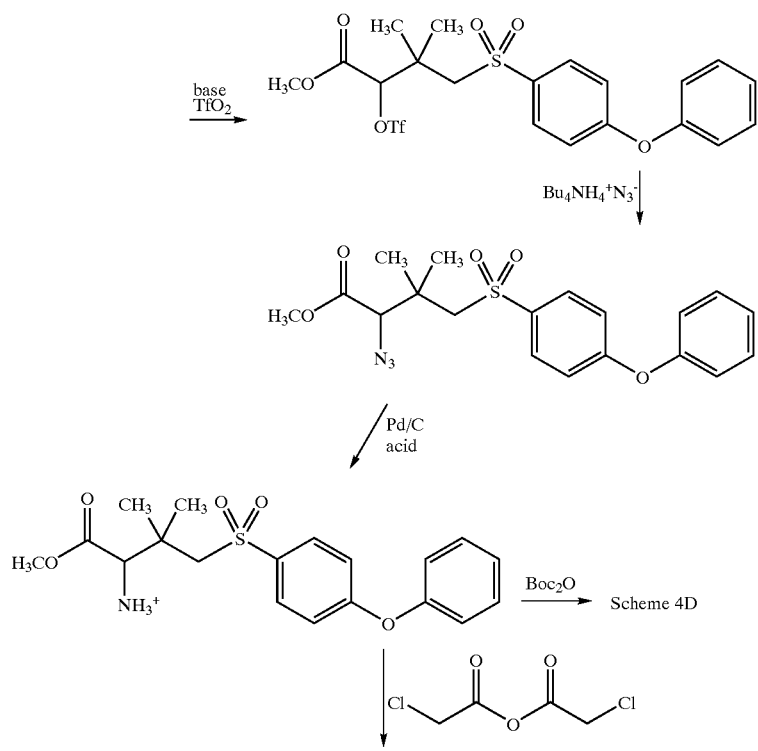

-continued
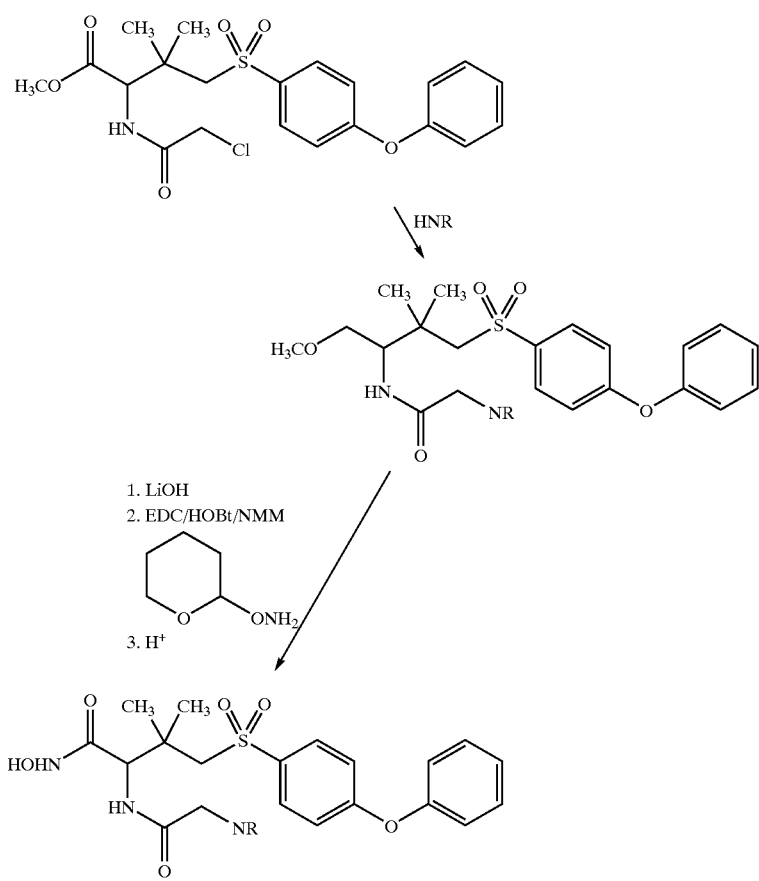
Example 13, R = —CH$_2$CH$_2$OCH$_2$CH$_2$—
Example 14, R = —CH$_2$CH$_2$CH$_2$CH$_2$—
Scheme 4D
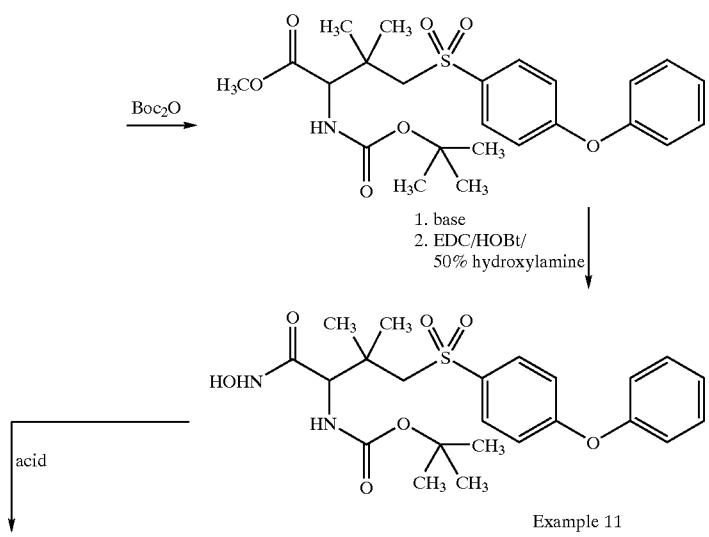
Example 11

-continued
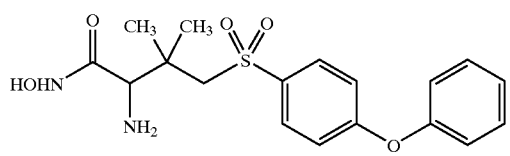
Example 12
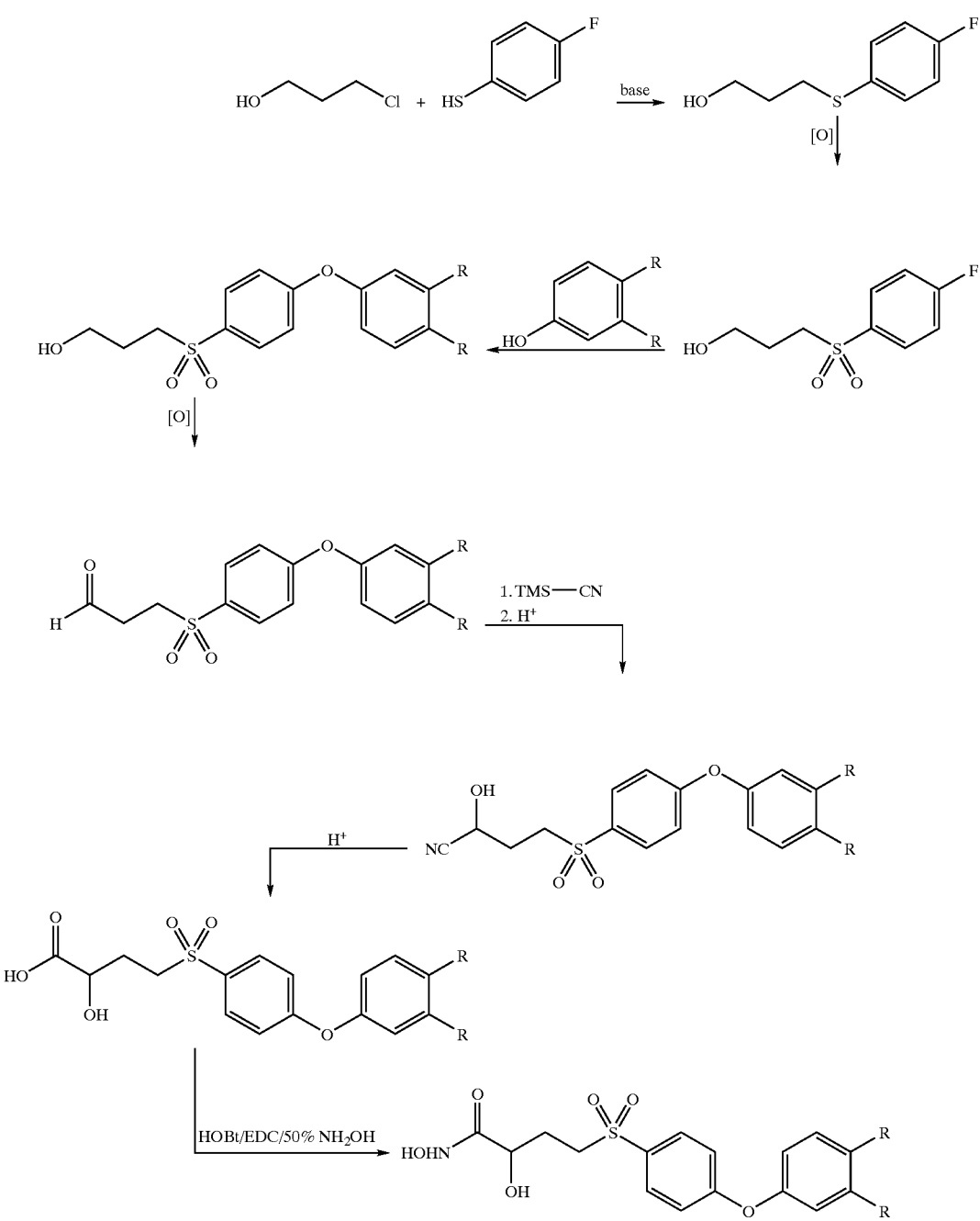
Example 4, R = H
Example 7, R = CH3

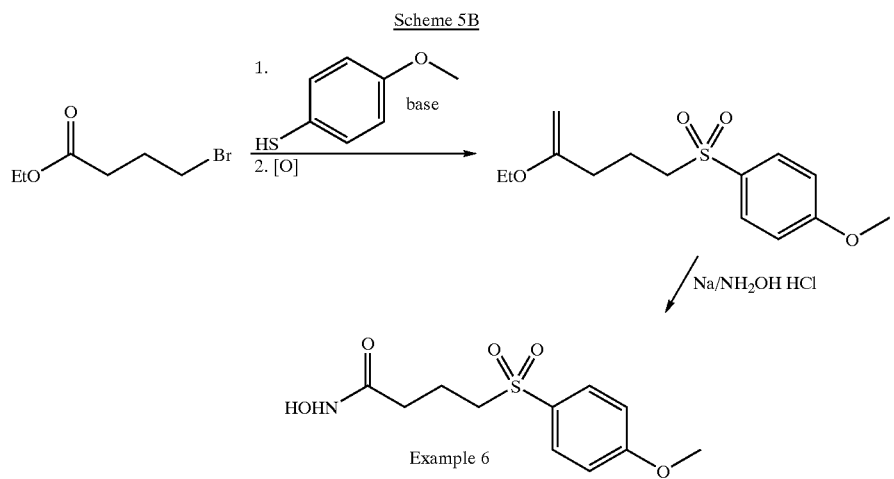
Scheme 5B
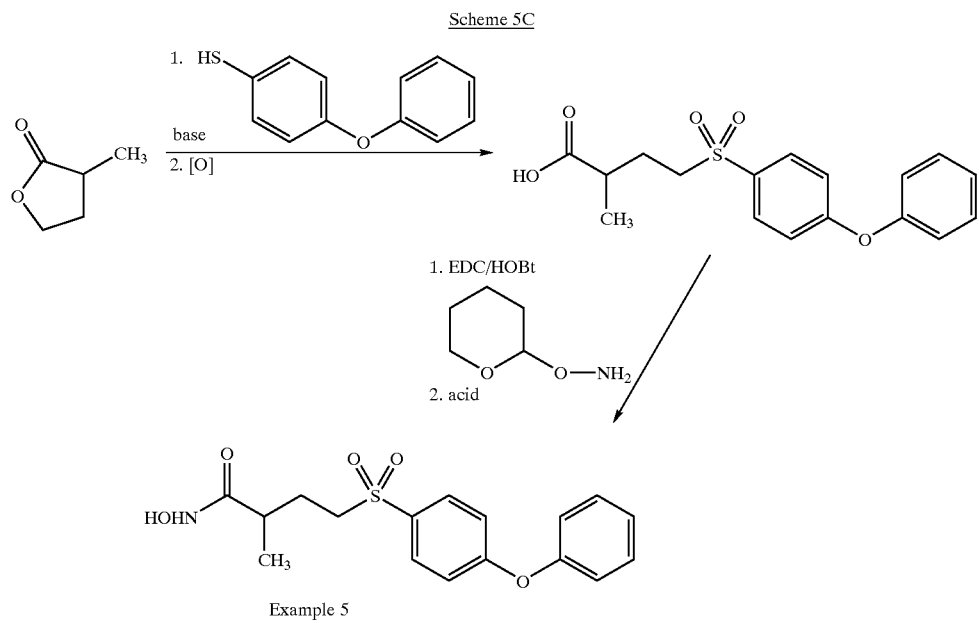
Scheme 5C
Scheme 6A

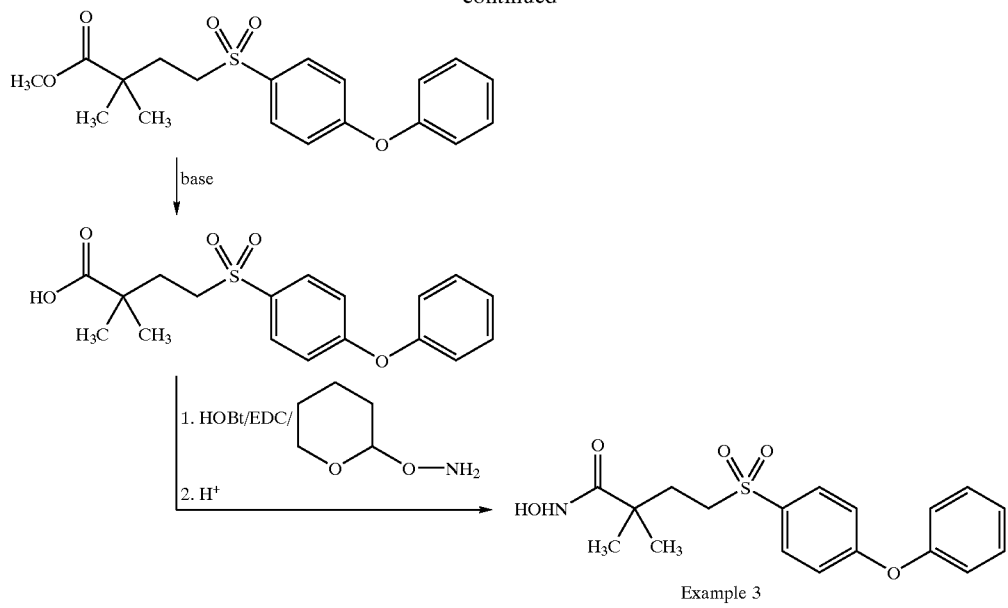
Example 3
Scheme 6B
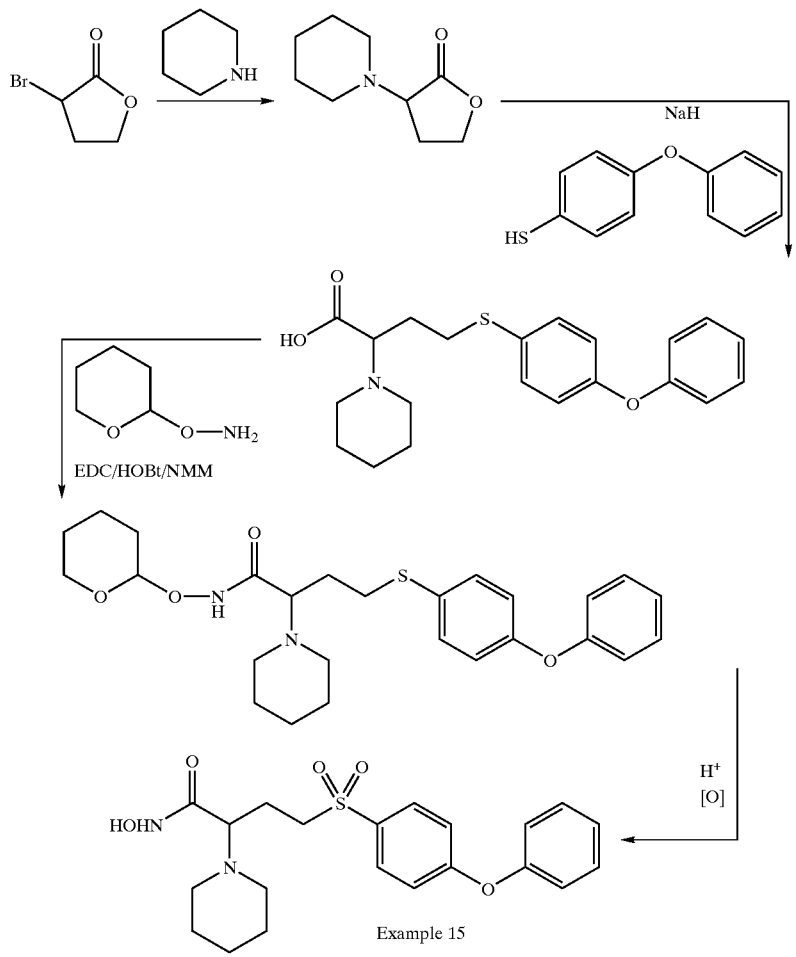
Example 15

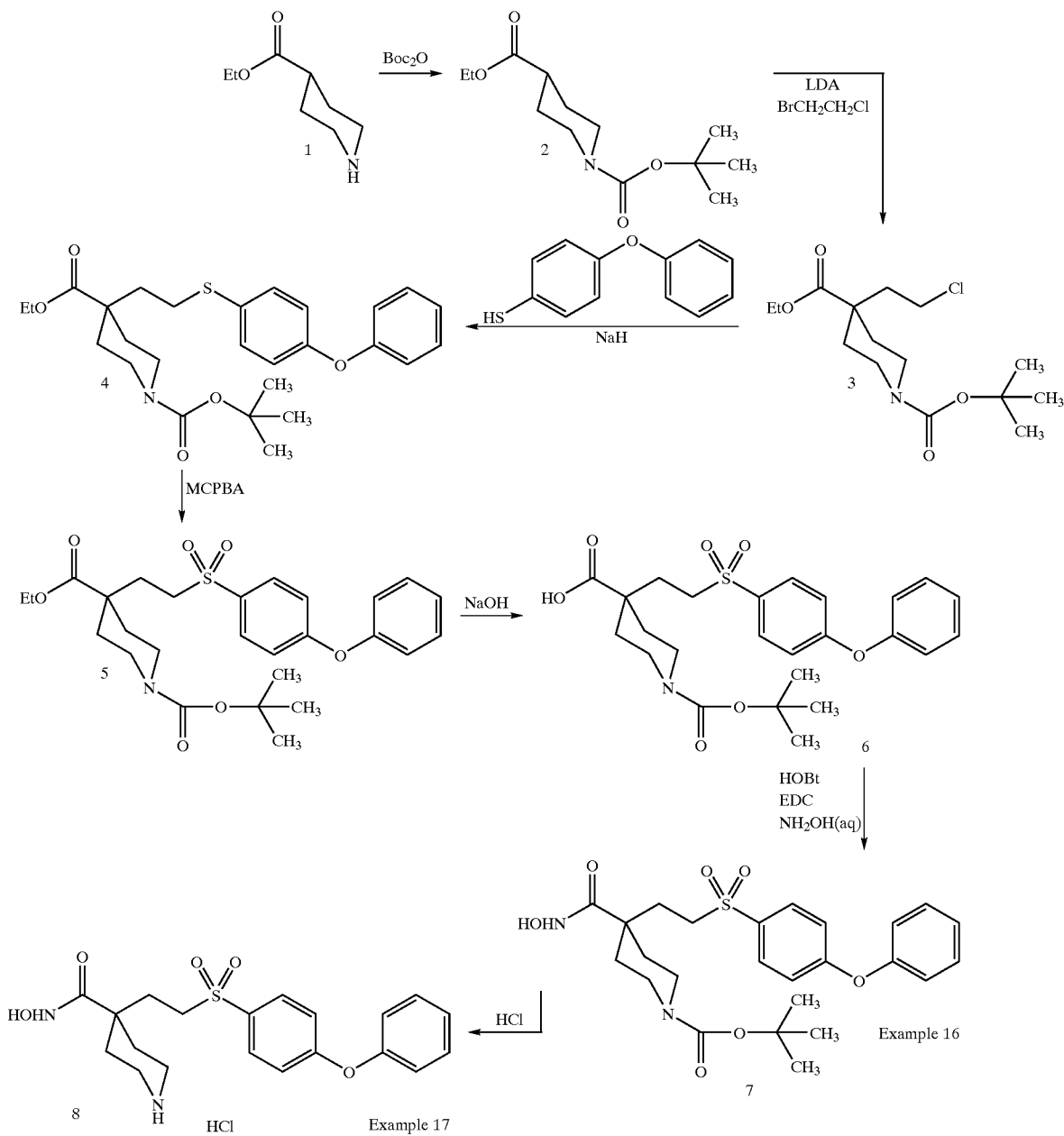

Scheme 7

Treatment Process

A process for treating a host mammal having a condition associated with pathological matrix metalloprotease activity is also contemplated. That process comprises administering a compound described hereinbefore in an MMP enzyme-inhibiting effective amount to a mammalian host having such a condition. The use of administration repeated a plurality of times is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-α convprtase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight daily, preferably about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Reminaton's Pharmaceutical Sciences*, Mack Publishing Co. (Easton, Pennsylvania: 1975) and Liberman, H.A. and Lachman, L., Eds., *Pharmaceutical Dosage Forms*, Marcel Decker, (New York, N.Y.: 1980).

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

(S)-N,2-Dihydroxy-3,3-dimethyl-4-
[(phenoxyphenyl)sulfonyl]butanamide

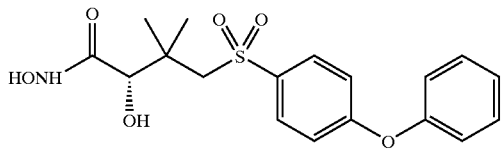

Part A: To a solution of 4-(phenoxy)benzenethiol (13.3 g, 65.8 mmol) in DMF (100 mL) was added $K_2CO_3$ (9.1 g, 65.8 mmol). To this solution was added S-pantolactone (8.5 g, 65.3 mmol) and the solution was heated to one hundred degrees Celsius for 4 hours. The solution was concentrated in vacuo and the residue was partitioned between ethyl acetate and 1N HCl. The organic layer was washed with saturated NaCl and dried over $MgSO_4$. To a solution of the crude sulfide in methanol (200 mL) and $H_2O$ (50 mL) was added Oxone® (121 g) and the mixture stirred for 18 hours. The mixture was filtered and the filtrate was partitioned between ethyl acetate and $H_2O$. The organic layer was dried over $MgSO_4$. A solution of the crude sulfone in methanol was treated with thionyl chloride (4.8 mL, 65.8 mmol) and the solution was heated to reflux for 1 hour. Concentration in vacuo provided the methyl ester sulfone as a white solid (13.0 g, 53%).

Part B: To a solution of the methyl ester sulfone of part A (780 mg, 2.06 mmol) in THF (10 mL) and methanol (10 mL) was added 50% aqueous $NH_2OH$ (2.4 mL, 41.2 mmol). The solution stirred for 3 days and then concentrated in vacuo. Reverse phase chromatography (on silica, acetonitrile/$H_2O$) provided the title compound as a white solid (300 mg, 38%) HPLC purity: 98.8%. MS(CI) $MH^+$ calculated for $C_{18}H_{21}NO_6S$: 380, found 380.

EXAMPLE 2

(R)-N,2-Dihydroxy-3,3-dimethyl-4-[(4-phenoxyphenyl)sulfonyl]butanamide

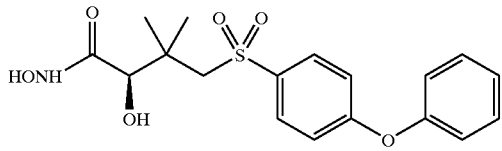

Part A: To a solution of 4-(phenoxy)benzenethiol (9.8 g, 48.5 mmol) in DMF was added $K_2CO_3$ (6.7 g, 48.5 mmol) followed by R-pantolactone (6.3 g, 48.4 mmol). The solution was heated to one hundred degrees Celsius for 3 hours followed by concentration in vacuo. The residue was partitioned between ethyl acetate and 1N HCl. The organic layer was dried over $MgSO_4$ and concentrated in vacuo. To a solution of the crude sulfide in methanol (200 mL) and $H_2O$ (50 mL) was added Oxone® (90 g, 145 mmol) and the solution was stirred for 18 hours. The mixture was filtered and the filtrate was concentrated and partitioned between ethyl acetate and $H_2O$. The organic layer was concentrated and dried over $MgSO_4$. After concentration in vacuo the residue was dissolved in methanol and treated with thionyl chloride (3.54 mL, 48.5 mmol). The solution was heated to reflux for 1 hour. Concentration in vacuo provided the methyl ester sulfone as a white solid (8.45 g, 54%).

Part B: To a solution of the methyl ester sulfone of part A (460 mg, 1.2 mmol) in THF (5 mL) and methanol (5 mL) was added 50% aqueous $NH_2OH$ (1 mL). The solution stirred for 4 days at ambient temperature and 3 days at fifty degrees Celsius. Concentration in vacuo followed by reverse phase chromatography (on silica, acetonitrile/$H_2O$) provided the title compound as a white solid (95 mg, 21%). MS(CI) $MH^+$ calculated for $C_{18}H_{21}NO_6S$: 380, found 380.

EXAMPLE 3

2,2-Dimethyl-N-hydroxy-4-[(4-phenoxyphenyl)sulfonyl]butanamide

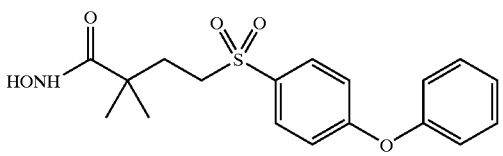

Part A: To a solution of diisopropylamine (2.24 mL, 16 mmol) in tetrahydrofuran (15 mL) cooled to zero degrees Celsius was added n-butyllithium (1.6 M in hexanes, 10 mL) over 2 minutes. The solution was cooled to minus seventy-eight degrees Celsius and methyl isobutyrate (1.60 mL, 14 mmol) was added. After 30 minutes 1-bromo-2-chloroethane (1.3 mL, 16 mmol) was added. The cooling bath was removed and the mixture was allowed to stir at ambient temperature for 2.5 hours. The solution was concentrated, diluted with 1N HCl and extracted with chloroform. The organic layer was dried over $MgSO_4$ and filtered through silica. Concentration in vacuo provided the crude chloride compound as a volatile oil (431 mg, 19%) and was used without further purification.

Part B: To a solution of sodium hydride (60% dispersion in mineral oil, 104 mg, 2.6 mmol) in acetonitrile (10 mL) cooled to zero degrees Celsius was added 4-(phenoxy)benzenethiol (0.53 g, 2.6 mmol). After the solution was stirred for 10 minutes, the chloride compound of part A (431 mg, 2.6 mmol) was added. The bath was removed and the reaction mixture was stirred overnight at ambient temperature. Concentration in vacuo followed by chromatography provided the sulfide as an oil (474 mg, 54%).

Part C: To a solution of the sulfide of part B (474 mg, 1.4 mmol)in glacial acetic acid (5 mL) was added 30% hydrogen peroxide (0.6 mL, 6 mmol) and the mixture was heated over a steam bath for 40 minutes. Lyophilization followed by chromatography (hexane/ethyl acetate) provided the sulfone as an oil (469 mg, 90%).

Part D: To a solution of the sulfone of part A (460 mg, 1.3 mmol) in 95% ethanol (5 mL) was added KOH (150 mg) and the solution was warmed to reflux. After 1.5 hours, the reaction was cooled to ambient temperature and adjusted to pH 4–5 using conc. HCl. The mixture was diluted with acetonitrile, then concentrated to dryness. The resulting acid was diluted with acetonitrile (4 mL) and O-tetrahydropyranyl hydroxylamine (176 mg, 1.5 mmol) was added, followed by 1-(3-dimethylaminopropyl)-3-ethylcarbodiimide hydrochloride (0.288 g, 1.5 mmol). The mixture was stirred overnight, then diluted with water and extracted with chloroform. The organic layer was dried over MgSO$_4$ and concentrated in vacuo. Chromatography provided the ester as an oil (421 mg, 73%).

Part E: To a solution of the ester of part D (421 mg, 0.95 mmol) in methanol (10 mL) was added toluenesulfonic acid (56 mg) and the solution was stirred 90 minutes at ambient temperature. Concentration in vacuo followed by chromatography (on silica, chloroform/methanol/ammonium hydroxide) provided the title compound as a white glass (237 mg, 69%). Analytical calculation for C$_{18}$H$_{21}$NO$_5$S·H$_2$O: C, 56.68; H, 6.08; N, 3.67. Found: C, 56.34; H, 5.52; N, 3.61.

EXAMPLE 4

N,2-Dihydroxy-4-[(4-phenoxyphenyl)-sulfonyl]butanamide

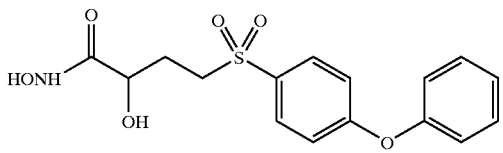

Part A: To a solution of 4-fluorothiophenol (10.0 g, 78.02 mmol) and 3-chloro-1-propanol (7.2 mL, 85.82 mmol) in DMF (80 mL) was added K$_2$CO$_3$ (32.4 g, 234.06 mmol). The solution stirred for 2 hours at ambient temperature. After concentration in vacuo the residue was partitioned between ethyl acetate and H$_2$O and the organic layer was washed with saturated NaCl and dried over MgSO$_4$. Concentration in vacuo provided a colorless oil. To a solution of the oil in methanol (300 mL) and H$_2$O (60 mL) was added Oxone®. The solution stirred for 2 hours. After filtration to remove excess Oxone® the filtrate was concentrated in vacuo and the residue was dissolved into H$_2$O and extracted with ethyl acetate. The combined organic layers were washed with saturated NaHCO$_3$ and saturated NaCl and dried over MgSO$_4$.

Concentration in vacuo provided the sulfone as a colorless oil (15.7 g, 92%).

Part B: To a solution of the sulfone of part A (12.7 g, 58.2 mmol) and phenol (16.4 g, 174.6 mmol) in DMF (100 mL) was added K$_2$CO$_3$ (24.1 g, 174.6 mmol) and the slurry stirred at one hundred degrees Celsius for 18 hours. The slurry was concentrated in vacuo and the residue was partitioned between ethyl acetate and H$_2$O. The organic layer was washed with 1N HCl, saturated NaHCO$_3$ and saturated NaCl, and dried over MgSO$_4$. Chromatography (on silica, ethyl acetate/hexane) provided the phenoxy compound as a pinkish solid (12.3 g, 72%).

Part C: To a solution of the phenoxy of part B (13.0 g, 44.5 mmol) in dichloromethane (60 mL) cooled to zero degrees Celsius, was added triethylamine (25 mL, 18.0 mmol). To this solution was added a solution of SO$_3$·pyridine (28.3 g, 177.9 mmol) in DMSO (60 mL) dropwise. The solution stirred for 2 hours at zero degrees Celsius. The solution was quenched in ice and extracted with ethyl acetate. The organic layer was washed with 5% KHSO$_4$ and saturated NaCl and dried over MgSO$_4$. Concentration in vacuo provided the aldehyde as a tan solid (12.7 g, 98%).

Part D: To a solution of the aldehyde of part C (12.9 g, 44.43 mmol) in dichloromethane (150 mL) cooled to zero degrees Celsius was added trimethylsilyl cyanide (6.6 g, 66.65 mmol) and zinc bromide (15.0 g, 66.65 mmol). The solution was stirred for 3 hours. The mixture was concentrated in vacuo and partitioned between ethyl acetate and 2N HCl. The organic layer was washed with saturated NaHCO$_3$ and saturated NaCl and dried over MgSO$_4$. Chromatography (on silica, ethyl acetate/CH$_2$Cl$_2$) provided the cyano compound as a white solid (10.3 g, 73%).

Part E: To a solution of the cyano compound of part D (10.3 g, 32.3 mmol) in glacial acetic acid (30 mL) was added 6N HC$_1$ (100 mL). The solution heated at ninety degrees Celsius for 2 hours. The solution was concentrated in vacuo to dryness to provide the acid as a tan solid (9.1 g, 71%).

Part F: To a solution of the acid of part E (2.0 g, 5.9 mmol) and N-hydroxybenzotriazole (1.0 g, 7.14 mmol) in DMF was added 1-(3-dimethylaminopropyl)-3-ethylcarbodiimide hydrochloride (1.3 g, 6.54 mmol). After 1 hour of stirring at ambient temperature 50% aqueous NH$_2$OH (1.1 mL, 17.8 mmol) and 4-methylmorpholine (2.0 mL, 17.8 mmol) were added. The solution was stirred for 1 hour. The solution was concentrated in vacuo and partitioned between ethyl acetate and 1N HCl and the organic layer was washed with saturated NaHCO$_3$ and saturated NaCl and dried over Na$_2$SO$_4$. Reverse phase chromatography (on silica, acetonitrile/H$_2$O) provided the title compound as a white solid (100 mg, 5%). MS(CI) MH$^+$ calculated for C$_{16}$H$_{17}$NO$_6$S: 352, found 352.

EXAMPLE 5

N-Hydroxy-2-methyl-4-[(4-phenoxyphenyl)sulfonyl]butanamide

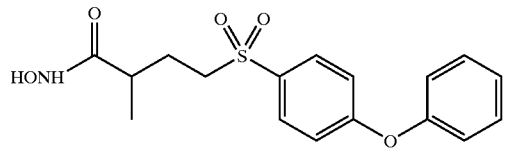

Part A: To a solution of NaH (60% suspension in mineral oil, 0.88 g, 22 mmol) in THF (20 mL) cooled to zero degrees Celsius was added 4-(phenoxy)benzenethiol (4.04 g, 20 mmol). After 10 minutes, ethanol (5 mL) was added, followed by α-methyl-γ-butyrolactone (2.38 g, 25 mmol), and the reaction mixture was warmed to reflux. After 20 hours, the mixture was cooled and concentrated. The residue was diluted with water and acidified with concentrated HCl. The aqueous mixture was extracted with chloroform and the organic layer was dried over MgSO$_4$ and concentrated in vacuo. Chromatography (on silica, hexane/ethyl acetate) provided the sulfide as an oil (3.74 g, 62%). MS(CI) MH$^+$ calculated for C$_{17}$H$_{18}$O$_3$S: 303, found: 303.

Part B: To a solution of the sulfide of part A (3.74 g, 12.4 mmol) in glacial acetic acid (25 mL) was added 30% hydrogen peroxide (4.8 mL, 48 mmol). The solution was heated over a steam bath for 40 minutes. Lyophilization followed by chromatography provided the sulfone as a wax (3.62 g, 89%).

Part C: To a solution of the sulfone of part B (2.40 g, 7.2 mmol) in acetonitrile (10 mL) was added O-tetrahydropyranyl hydroxylamine (0.90 g, 7.7 mmol) followed by 1-(3-dimethylaminopropyl)-3-ethylcarbodiimide hydrochloride (1.48 g, 7.7 mmol). The mixture was stirred overnight, then diluted with water and extracted with chloroform. The organic layer was dried over MgSO$_4$ and concentrated in vacuo. Chromatography provided the ester as an oil (2.23 g, 71% yield).

Part D: To the ester of part C (2.23 g, 5.11 mmol) in methanol (60 mL) was added p-toluenesulfonic acid (1.2 g) and the solution was stirred 40 minutes. Following neutralization with concentrated ammonium hydroxide, chromatography (on silica, chloroform/methanol/ammonium hydroxide) provided the title compound as a white wax (981 mg, 54%). Analytical calculation for $C_{17}H_{19}NO_5S \cdot 0.5H_2O$: C, 56.97; H, 5.62; N, 3.91. Found: C, 56.90; H, 5.22; N, 4.02.

EXAMPLE 6

N-Hydroxy-4-[(4-methoxyphenyl)-sulfonyl]butanamide

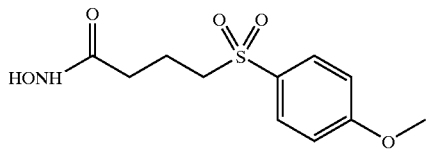

Part A: To a solution of 4-methoxybenzenethiol (2.5 g, 17.83 mmol) and ethyl 4-bromobutyrate (3.5 g, 17.83 mmol) in ethanol (50 mL) was cooled on an ice bath and triethylamine (2.73 mL, 19.61 mmol) was added. The solution stirred for 6 hours at ambient temperature. To this solution was added $H_2O$ (10 mL) and Oxone® (22 g, 35.7 mmol) and the solution stirred for 20 hours. The solution was filtered to remove excess Oxone® and the filtrate was concentrated in vacuo. The residue was dissolved into $H_2O$ and extracted with ethyl acetate. The combined organic layers were washed with saturated $NaHCO_3$ and saturated NaCl and dried over $MgSO_4$. Chromatography (on silica, ethyl acetate/hexane) provided the sulfone as a white solid (2.41 g, 47%). HPLC purity: 97%.

Part B: To a solution of the sulfone of part A (2.41 g, 8.42 mmol) and hydroxylamine hydrochloride (700 mg, 10.10 mmol) in methanol (50 mL), cooled to zero degrees Celsius, was added Na metal (470 mg, 20.20 mmol). After stirring at ambient temperature for 2 hours, the reaction was quenched by the addition of dry ice to pH=7. Following concentration in vacuo the residue was dissolved into $H_2O$ and acidified to pH=3 with 2N HCl. The solution was extracted with ethyl acetate and the combined organic layers were washed with saturated NaCl and dried over $Na_2SO_4$. Chromatography (on silica, ethyl acetate/hexane) provided the title compound as a white solid (300 mg, 13%). HPLC purity: 98.7%. HRMS calculated for $C_{11}H_{15}NO_5S$: 274.0749, found 274.0779.

EXAMPLE 7

(+/−)-4-[[4-(3,4-Dimethylphenoxy)phenyl ]-sulfonyl]-N,2-dihydroxybutanamide

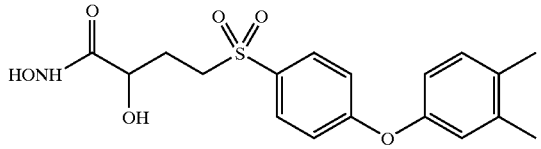

Part A: To a solution of 4-fluorothiophenol (20 g, 156 mmol) in DMF (100 mL) was added 3-chloro-1-propanol (11.5 g, 121 mmol) and $K_2CO_3$ (64.7 g, 468 mmol) and the mixture was stirred for 18 hours. The solution was removed by concentration in vacuo and the residue was partitioned between ethyl acetate and $H_2O$. The organic layer was extracted 3 times with ethyl acetate and the combined organics were washed with saturated NaCl and dried over $Na_2SO_4$. Concentration in vacuo provided the sulfide as an amber oil (30.53 g).

Part B: To a solution of the sulfide of part A (30.5 g) in methanol (450 mL) and $H_2O$ (50 mL) was added Oxone® (262 g, 426 mmol) and the mixture was stirred for 18 hours. The mixture is filtered to collect the excess solids and the filtrate was concentrated in vacuo. The residue was partitioned between ethyl acetate and $H_2O$ and the organic layer was washed with 5% $NaHCO_3$ and saturated NaCl and dried over $Na_2SO_4$. Concentration in vacuo provided the sulfone as an amber oil (22.04 g, 83%, 2 steps).

Part C: To a solution of the sulfone of part B (22.04 g, 101 mmol) in DMF (50 mL). To this solution is added 3,4-dimethylphenol (18.62 g, 152 mmol) in DMF (50 mL) followed by $K_2CO_3$ (43.13 g, 312 mmol) and the solution was heated at one hundred ten degrees Celsius for 17 hours. The solution was partitioned between ethyl acetate and $H_2O$ and the organic layer was washed with 1N HCl, 5% $NaHCO_3$, and NaCl and dried over $Na_2SO_4$. Chromatography (on silica, ethyl acetate/hexane) provided the dimethylphenoxyphenol as a white solid (15.17 g, 47%).

Part D: To a solution of dimethylphenoxyphenol of part C (15.17 g, 47.4 mmol) in dichloromethane (80 mL) was added triethylamine (20 mL) followed by pyridine·$SO_3$ (22.46 g, 141 mmol) in DMSO (80 mL) added dropwise. The solution was stirred for 1 hour. The reaction was quenched by the addition of crushed ice and concentrated in vacuo to remove the solvent. The solution was extracted with ethyl acetate and the organic layer was washed with saturated NaCl and dried over $MgSO_4$. Concentration in vacuo provided the aldehyde as an orange oil (15.03 g).

Part E: To a solution of the aldehyde of part D (15.6 g) in dichloromethane (100 mL) was added trimethylsilyl cyanide (7.3 mL, 71.1 mmol) followed by zinc iodide (2.27 g, 7.1 mmol) and the solution was stirred on an ice bath for 17 hours. The solution is partitioned between ethyl acetate and 2M HCl. The organic layer was washed with $H_2O$ and saturated NaCl and dried over $MgSO_4$. Filtration through a silica pad provided the nitrile as an amber oil (14.13 g).

Part F: A solution of the nitrile of part E (14.13 g) in glacial acetic acid (50 mL) and concentrated HCl (50 mL) was heated to one hundred ten degrees Celsius for 2 hours and was stirred for 18 hours. The solution was concentrated in vacuo to provide the acid as a brown oil (13.53 g, 75%, three steps).

Part G: To a solution of the acid of part F (13.5 g, 35.7 mmol) in methanol (100 mL) cooled to zero degrees Celsiius was added thionyl chloride (4.1 mL, 56.2 mmol) dropwise and the solution is stirred at ambient temperature for 72 hours. The solution was concentration in vacuo and the residue was dissolved into ethyl acetate and washed with 5% $NaHCO_3$ and saturated NaCl and dried over $Na_2SO_4$. Chromatography (on silica, ethyl acetate/hexane) provided the methyl ester as a white solid (14.51 g, quantitative yield).

Part H: To a solution of the methyl ester of part G (630 mg, 1.6 mmol) in THF (30 mL) was added 50% aqueous hydroxylamine (1 mL) and the solution was stirred for 140 hours. The solution is concentrated and the residue was dissolved into ethyl acetate and washed with 5% $NaHCO_3$ and dried over $Na_2SO_4$. Concentration in vacuo provided the title compound as a white solid (450 mg, 69%). MS(CI) $MH^+$ calculated for $C_{18}H_{21}NO_6S$: 380, found 380.

EXAMPLE 8

(S)-N-Hydroxy-3,3-dimethyl-4-[(4-phenoxyphenyl)sulfonyl]-2-(3-pyridinylmethoxy)butanamide Monohydrochloride

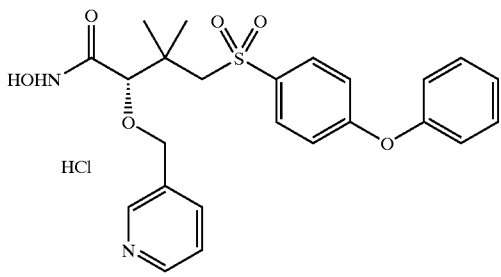

Part A: To a solution of 4-(phenoxy)benzenethiol (13.3 g, 65.8 mmol) in DMF (100 mL) was added $K_2CO_3$ (9.1 g, 65.8 mmol). To this solution was added S-pantolactone (8.5 g, 65.3 mmol) and the solution was heated to one hundred degrees Celsius for 4 hours. The solution was concentrated in vacuo and the residue was partitioned between ethyl acetate and 1N HCl. The organic layer was washed with saturated NaCl and dried over $MgSO_4$. To a solution of the crude sulfide in methanol (200 mL) and $H_2O$ (50 mL) was added Oxone® (121 g) and the mixture stirred for 18 hours. The mixture was filtered and the filtrate was partitioned between ethyl acetate and $H_2O$. The organic layer was dried over $MgSO_4$. A solution of the crude sulfone in methanol was treated with thionyl chloride (4.8 mL, 65.8 mmol) and the solution was heated to reflux for 1 hour. Concentration in vacuo provided the methyl ester sulfone as a white solid (13.0 g, 53%).

Part B: To DMF (12 mL) was added NaH (60% suspension in mineral oil, 255 mg, 10.6 mmol) followed by the methy ester sulfone of part A (2.00 g, 5.28 mmol). To a solution of 3-picolyl chloride hydrochloride (868 mg, 5.28 mmol) in DMF (12 mL) was added NaH (60% suspension in mineral oil, 257 mg, 10.7 mmol). After 5 minutes the solution of the sulfone was added to this solution of the chloride and the mixture stirred for 18 hours at ambient temperature. The reaction was quenched by the addition of $H_2O$ and the solution was concentrated in vacuo. The residue was dissolved into ethyl acetate and $H_2O$ and the aqueous is extracted twice with ethyl acetate. The combined organic layers are washed with saturated $NaHCO_3$ and saturated NaCl and dried over $Na_2SO_4$. Chromatography (on silica, ethyl acetate/hexane) provided the ether as a solid (950 mg, 38%).

Part C: To a solution of the ether of part B (950 mg, 2.0 mmol) in glacial acetic acid (15 mL) was added concentrated HCl (15 mL) and the solution was heated to reflux for 3 hours. The solution was concentrated in vacuo provided the acid as a white foam (1.05 g, quantitative yield).

Part D: To a solution of the acid of part C (1.03 g, 2.0 mmol) in DMF (10 mL) was added N-hydroxybenzotriazole (301 mg, 2.2 mmol), 4-methylmorpholine (1.02 mL, 10 mmol), O-tetrahydropyranyl hydroxylamine (725 g, 6.2 mmol) and 1-(3-dimethylaminopropyl)-3-ethylcarbodiimide hydrochloride(500 mg, 2.6 mmol). The solution was stirred for 20 hours at ambient temperature. The solution was partitioned between ethyl acetate and $H_2O$ and the organic layer was washed with saturated NaCl and dried over $Na_2SO_4$. Chromatography (on silica, ethyl acetate/hexane) provided the ester as a white solid (890 mg, 82%).

Part E: To a solution of the ester of part D (890 mg, 1.6 mmol) in 4M HCl in dioxane (5 mL) was added methanol (12 drops) and the solution was stirred for 30 minutes. The solution was concentrated in vacuo and reverse phase chromatography (on silica, acetonitrile/$H_2O$) provided the title compound as a white solid (540 mg, 66%). MS(CI) $MH^+$ calculated for $C_{24}H_{26}N_2O_6S$: 471, found 471.

EXAMPLE 8a

Preparation of (S)-N-Hydroxy-3,3-dimethyl-4-[(4-phenoxyphenyl)sulfonyl]-2-(3-pyridinylmethoxy)butanamide

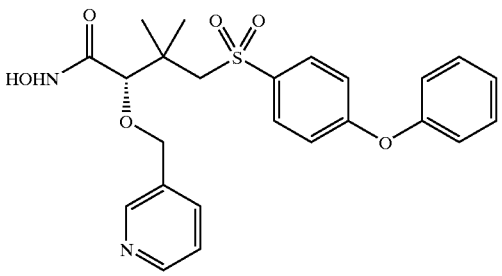

A solution of the HCl salt of example 8 in saturated $NaHCO_3$ was extracted with ethyl acetate. The organic layer was washed with saturated NaCl and dried over $Na_2SO_4$. Concentration in vacua provided the title compound.

EXAMPLE 9

(S) -N-Hydroxy-3,3-dimethyl-4-[(4-phenoxyphenyl)sulfonyl]-2- (4-pyridinyl-methozy)butanamide Monohydrochloride

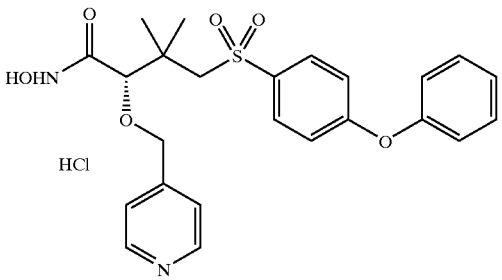

Part A: To a solution of 4-(phenoxy)benzenethiol (13.3 g, 65.8 mmol) in DMF (100 mL) was added $K_2CO_3$ (9.1 g, 65.8 mmol). To this solution was added S-pantolactone (8.5 g, 65.3 mmol) and the solution was heated to 100° C. for 4 hours. The solution was concentrated in vacuo and the residue was partitioned between ethyl acetate and 1N HCl. The organic layer was washed with saturated NaCl and dried over $MgSO_4$. To a solution of the crude sulfide in methanol (200 mL) and $H_2O$ (50 mL) was added Oxone® (121 g) and the mixture stirred for 18 hours. The mixture was filtered and the filtrate was partitioned between ethyl acetate and $H_2O$. The organic layer was dried over $MgSO_4$. A solution of the crude sulfone in methanol was treated with thionyl chloride (4.8 mL, 65.8 mmol) and the solution was heated to reflux for 1 hour. Concentration in vacuo provided the methyl ester sulfone as a white solid (13.0 g, 53%).

Part B: To DMF (12 mL) was added NaH (60% suspension in mineral oil, 253 mg, 10.6 mmol) followed by the methyl ester sulfone of part A (2.00 g, 5.28 mmol). To a solution of 4-picolyl chloride hydrochloride (868 mg, 5.28 mmol) in DMF (12 mL) was added NaH (60% suspension in mineral oil, 255 mg, 10.7 mmol). After 5 minutes the solution of the sulfone was added to this solution of the chloride and the mixture stirred for 18 hours at ambient temperature. The reaction was quenched by the addition of H$_2$O and the solution was concentrated in vacuo. The residue was dissolved into ethyl acetate and H$_2$O and the aqueous was extracted twice with ethyl acetate. The combined organic layers were washed with saturated NaHCO$_3$ and saturated NaCl and dried over Na$_2$SO$_4$. Chromatography (on silica, ethyl acetate/hexane) provided the ether as a solid (1.07 mg, 43%).

Part C: To a solution of the ether of part B (1.07 mg, 2.15 mmol) in glacial acetic acid (15 mL) was added concentrated HCl (15 mL) and the solution was heated to reflux for 3 hours. The solution was concentrated in vacuo provided the acid as a white foam (1.09 mg, quantitative yield).

Part D: To a solution of the acid of part C (1.09 g, 2.0 mmol) in DMF (10 mL) was added N-hydroxybenzotriazole (301 mg, 2.2 mmol), 4-methylmorpholine (1.02 mL, 10 mmol), O-tetrahydropyranyl hydroxylamine (725 g, 6.2 mmol) and 1-(3-dimethylaminopropyl)-3-ethylcarbodiimide hydrochloride (500 mg, 2.6 mmol). The solution stirred for 20 hours at ambient temperature. The solution was partitioned between ethyl acetate and H$_2$O and the organic layer was washed with saturated NaCl and dried over Na$_2$SO$_4$. Chromatography (on silica, ethyl acetate/hexane) provided the ester as a white solid (840 mg, 77%).

Part E: To a solution of the ester of part D (840 mg, 1.5 mmol) in 4M HCl in dioxane (5 mL) was added methanol (12 drops) and the solution was stirred for 30 minutes. The solution was concentrated in vacuo and reverse phase chromatography (on silica, acetonitrile/H$_2$O) provided the title compound as a white solid (350 mg, 45%). MS(CI) MH$^+$ calculated for C$_{24}$H$_{26}$N$_2$O$_6$S: 471, found 471.

EXAMPLE 9a (S)-N-Hydroxy-3,3-dimethyl-4-[(4-phenoxyphenyl)sulfonyl]-2-(4-pyridinylmethoxy)butanamide

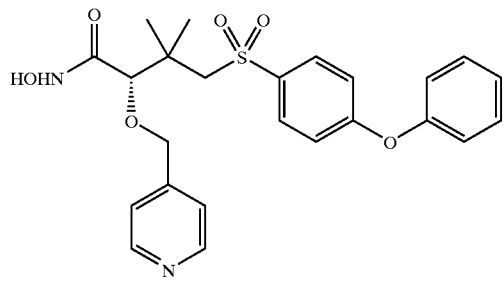

A solution of the HCl salt of example 9 in saturated NaHCO$_3$ was extracted with ethyl acetate. The organic layer was washed with saturated NaCl and dried over Na$_2$SO$_4$. Concentration in vacuc provided the title compound.

EXAMPLE 10

(S)-N-Hydroxy-3,3-dimethyl-4-[(4-phenoxyphenyl)sulfonyl]-2 (2-pyridinyl methoxy)butanamide Monohydrochloride

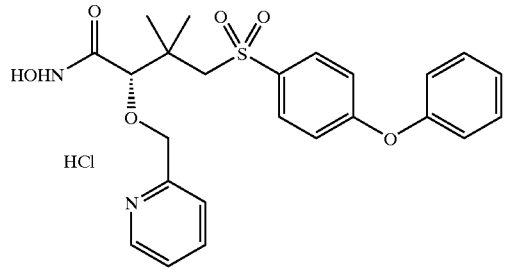

Part A: To a solution of 4-(phenoxy)benzenethiol (13.3 g, 65.8 mmol) in DMF (100 mL) was added K$_2$CO$_3$ (9.1 g, 65.8 mmol). To this solution was added S-pantolactone (8.5 g, 65.3 mmol) and the solution was heated to one hundred degrees Celsius for 4 hours. The solution was concentrated in vacuo and the residue was partitioned between ethyl acetate and 1N HCl. The organic layer was washed with saturated NaCl and dried over MgSO$_4$. To a solution of the crude sulfide in methanol (200 mL) and H$_2$O (50 mL) was added Oxone® (121 g) and the mixture stirred for 18 hours. The mixture was filtered and the filtrate was partitioned between ethyl acetate and H$_2$O. The organic layer was dried over MgSO$_4$. A solution of the crude sulfone in methanol was treated with thionyl chloride (4.8 mL, 65.8 mmol) and the solution was heated to reflux for 1 hour. Concentration in vacuo provided the methyl ester sulfone as a white solid (13.0 g, 53%).

Part B: To a solution of the methyl ester sulfone (21.1 g, 57.8 mmol) in methanol (120 mL) was added thionyl chloride (5.1 mL, 69.5 mmol) and the solution was heated to reflux for 1 hour. The solution was concentrated and the residue was dissolved into ethyl acetate and washed with saturated NaHCO$_3$, H$_2$O, and saturated NaCl and dried over Na$_2$SO$_4$. Chromatography (on silica, ethyl acetate/hexane) provided the methyl ester as a solid (13.3 g, 61%).

Part C: To a slurry of NaH (60% suspension in mineral oil, 253 mg, 6.32 mmol) in DMF (12 mL) was slowly added the alcohol of part B (2.0 g, 5.28 mmol) and the mixture was stirred for 30 minutes. To a slurry of NaH (60% suspension in mineral oil, 253 mg, 6.32 mmol) in DMF (12 mL) was added 2-picoyl chloride hydrochloride (868 mg, 5.28 mmol). This solution was added to the first mixture dropwise and the solution was stirred for 18 hours. The reaction was quenched with H$_2$O and the solvent was removed by concentration in vacuo. The residue was partitioned between ethyl acetate and H$_2$O. The organic layer was washed with saturated NaHCO$_3$ and saturated NaCl and dried over Na$_2$SO$_4$. Chromatography (on silica, methyl acetate/hexane) provided the ether as an oil (1.32 g, 53%).

Part D: A solution of the ether of part C (1.0 g, 2.0 mmol) in acetic acid (15 mL) and concentrated HCl (15 mL) was heated to reflux for 3.5 hours. The solution was concentrated in vacuo to provide the acid as an off-white foam (910 mg, 92%).

Part E: To a solution of the acid of part D (910 mg, 1.86 mmol) in DMF (10 mL) was added N-hydroxybenzotriazole (301 mg, 2.23 mmol), 4-methylmorpholine (1.02 mL, 9.3 mmol), O-tetrahydropyranyl hydroxylamine (675 mg, 5.7 mmol) and 1-(3-dimethylaminopropyl)-3-ethylcarbodiimide hydrochloride (499 mg, 2.60 mmol) and the solution was stirred at ambient temperature for 18 hours. The solution was concentrated in vacuo and the residue was partitioned between ethyl acetate and H$_2$O. The organic layer was washed with H$_2$O and saturated NaCl and dried over Na$_2$SO$_4$. Chromatography (on silica, ethyl acetate/hexane) provided the ester as a foam (910 mg, 88%).

Part F: A solution of the ester of part E (910 mg, 1.64 mmol) in 4M HCl (5 mL) and methanol (12 drops) was stirred for 30 minutes. The solution was concentrated in vacuo. Reverse phase chromatography (on silica, acetonitrile/H$_2$O) provided the title compound as a white solid (260 mg, 33%). MS(CI) MH$^+$ calculated for C$_{24}$H$_{26}$N$_2$O$_6$S: 471, found 471.

EXAMPLE 11

(S)-1,1-Dimethylethyl [1-](hydroxyamino)-carbonyl-2,2-dimethyl-3-[(4-phenoxyphenyl)-sulfonyl]propyl]carbamate

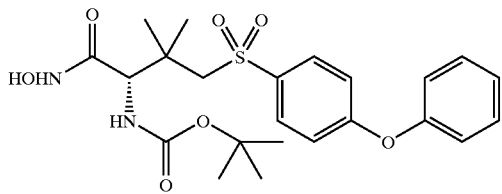

Part A: To a solution of 4-(phenoxy)benzenethiol (9.8 g, 48.5 mmol) in DMF was added K$_2$CO$_3$ (6.7 g, 48.5 mmol) followed by R-pantolactone (6.3 g, 48.4 mmol). The solution was heated to one hundred degrees Celsius for 3 hours followed by concentration in vacuo. The residue was partitioned between ethyl acetate and 1N HCl. The organic layer was dried over MgSO$_4$ and concentrated in vacuo. To a solution of the crude sulfide in methanol (200 mL) and H$_2$O (50 mL) was added Oxone® (90 g, 145 mmol) and the solution was stirred for 18 hours. The mixture was filtered and the filtrate was concentrated and partitioned between ethyl acetate and H$_2$O. The organic layer was concentrated and dried over MgSO$_4$. After concentration in vacuo the residue was dissolved in methanol and treated with thionyl chloride (3.54 mL, 48.5 mmol). The solution was heated to reflux for 1 hour. Concentration in vacuo provided the methyl ester sulfone as a white solid (8.45 g, 54%).

Part B: To a solution of the methyl ester sulfone of part A (4.0 g, 10.57 mmol) in dichloromethane (50 mL) was added pyridine (1.1 mL, 13.33 mmol) and the solution was cooled to minus seventy-five degrees Celsius. To this solution was added triflic anhydride (2.0 mL, 11.63 mmol) dropwise. The solution was stirred at ambient temperature for 2 hours. The solution was concentrated in vacuo and the residue was partitioned between ethyl acetate and H$_2$O. The organic layer was washed with saturated NaHCO$_3$ and saturated NaCl and dried over Na$_2$SO$_4$. Concentration in vacuo provided the triflate as a colored oil (5.4 g, quantitative yield).

Part C: To a solution of the triflate of part B (5.4 g, 10.58 mmol) in toluene (100 mL) was added n-butyl ammonium azide (3.3 g, 11.64 mmol) and the solution was stirred at ambient temperature for 20 hours. The solution was concentrated in vacuo and the residue was partitioned between ethyl acetate and H$_2$O. The organic layer was washed with saturated NaHCO$_3$, 5% citric acid and saturated NaCl and dried over Na$_2$SO$_4$. Concentration in vacuo provided the azide as an orange oil (7.4 g).

Part D: To a solution of the azide of part C (4.3 g, 10.58 mmol) and p-toluenesulfonic acid monohydrate (2.0 g, 10.58 mmol) in methanol (80 mL) was added 4% Pd/C and the solution was stirred for 1 hour under H$_2$ at 50 psi. The solution continued to stir for 18 hours. The mixture was filtered through Celite and the filtrate was concentrated in vacuo to provide the crude amine p-toluenesulfonic acid salt as a colored oil (9.3 g).

Part E: To a solution of the crude amine salt of part D (5.8 g, 10.55 mmol) in THF (100 mL) was added di-t-butyl dicarbonate (2.5 g, 11.61 mmol) and triethylamine (3.2 mL, 23.21 mmol). The solution was stirred at ambient temperature for 18 hours. The solution was concentrated in vacuo and the residue was partitioned between ethyl acetate and H$_2$O. The organic layer was washed with 5% KHSO$_4$ and saturated NaCl and dried over MgSO$_4$. Chromatography (on silica, ethyl acetate/hexane) provide the protected amine as a white foam (4.0 g, 87%).

Part F: To a solution of the protected amine of part E (1.0 g, 2.09 mmol) in THF (10 mL) was added LiOH (400 mg, 8.38 mmol) in H$_2$O (10 mL) and the solution was stirred at ambient temperature for 6 hours. The solution was concentrated in vacuo and the residue was partitioned between ethyl acetate and 5% KHSO$_4$. The organic layer was washed with saturated and dried over Na$_2$SO$_4$. Concentration in vacuo provided the acid as a white foam (1.0 g, quantitative yield).

Part G: To a solution of the acid of part F (1.0 g, 2.16 mmol) in DMF (10 mL) was added N-hydroxybenzotriazole (450 mg, 3.24 mmol), 1-(3-dimethylaminopropyl)-3-ethylcarbodiimide hydrochloride (500 mg, 2.59 mmol) and 50 aqueous hydroxylamine (2.5 mL) and was stirred at ambient temperature for 1 hour. The solution was concentrated in vacuo and the residue partitioned between ethyl acetate and saturated NaHCO$_3$. The organic layer was washed with saturated NaCl and dried over Na$_2$SO$_4$. Reverse phase chromatography (on silica, acetonitrile/H$_2$O) provided the title compound as a white foam (700 mg, 70%). HPLC purity: 95%. MS(CI) MH$^+$ calculated for C$_{23}$H$_{30}$N$_2$O$_7$S: 479, found 479.

EXAMPLE 12

(S)-2-Amino-N-hydroxy-3,3-dimethyl-4-[(4-phenoxyphenyl)sulfonyl]butanamide Monohydrochloride

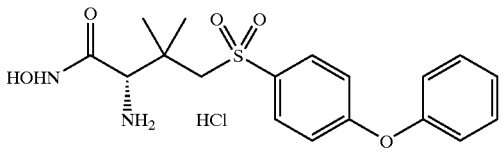

Part A: A solution of the hydroxamate of Example 11, part G (700 mg, 1.46 mmol) in 4M HCl (10 mL) was stirred at ambient temperature for 1 hour. The solution was concentrated in vacuo and tritration with ethyl ether provided the title compound as a white foam (600 mg, quantitative yield). HPLC purity: 93%. MS(CI) MH$^+$ calculated for C$_{18}$H$_{22}$N$_2$O$_5$S: 379, found 379.

EXAMPLE 13

(S)-N-[1-[(Hydroxyamino)-carbonyl]-2,2-dimethyl-3-[(4-phenoxyphenyl)sulfonyl]-propyl]-4-morpholineacetamide

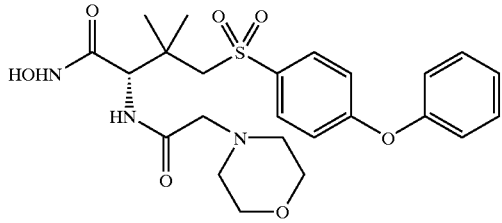

Part A: A solution of the methyl ester of Example 11, part E (1.84 g, 3.85 mmol) in 4M HCl (20 mL) was stirred at ambient temperature for 1.5 hour. The solution was concentrated in vacuo to provide the amine hydrochloride salt as a white foam (1.7 g, quantitative yield).

Part B: To a solution of the amine hydrochloride salt of part A (1.74 g, 4.20 mmol) and diisopropylethylamine (1.7 mL, 9.46 mmol) in dichloromethane (30 mL) cooled to zero degrees Celsius was added chloroacetic anhydride (800 mg, 4.62 mmol) in dichloromethane (10 mL) and the solution was stirred at ambient temperature for 18 hours. The solution was concentrated in vacuo and the residue was partitioned between ethyl acetate and saturated NaHCO₃. The organic layer was washed with 5% citric acid, H2O, and saturated NaCl and dried over Na₂SO₄. Chromatography (on silica, ethyl acetate/hexane) provided the chloro compound as an off-white foam (1.5 g, 79%).

Part C: To a solution of the chloro compound of part B (1.5 g, 3.30 mmol) in THF (10 mL) and H₂O (5 mL) was added morpholine (1.7 mL, 19.83 mmol) and the solution was stirred at ambient temperature for 18 hours. The solution was concentrated in vacuo and the residue was partitioned between ethyl acetate and saturated NaHCO₃. The organic layer was washed with saturated NaCl and dried over Na₂SO₄. Concentration in vacuo provided the morpholine compound as a white foam (1.6 g, 94%).

Part D: To a solution of the morpholine compound of part C (1.6 g, 3.17 mmol) in THF (10 mL) was added LiOH (530 mg, 12.68 mmol) in H₂O (10 mL) and the solution was stirred at ambient temperature for 2 hours. The solution was concentrated in vacuo. The residue was acidified to pH=6 with dry ice and 5% KHSO₄ and extracted with ethyl acetate. The organic layer was washed with saturated NaCl and dried over Na₂SO₄. Concentration in vacuo provided the acid as a white solid (1.4 g, 88%).

Part E: To a solution of the acid of part D (700 mg, 1.43 mmol) in DMF (10 mL) was added N-hydroxybenzotriazole (300 mg, 2.14 mmol), 4-methylmorpholine (0.5 mL, 4.28 mmol), O-tetrahydropyranyl hydroxylamine (500 mg, 4.42 mmol) and 1-(3-dimethylaminopropyl)-3-ethylcarbodiimide hydrochloride (400 mg, 2.14 mmol) and the solution was stirred for 6 hours at ambient temperature. The solution was concentrated in vacuo and the residue was partitioned between ethyl acetate and H₂O and the organic layer was washed with saturated NaCl and dried over Na₂SO₄. Chromatography (on silica, ethyl acetate/hexane/methanol) provided the ester as a white foam (600 mg, 75%).

Part F: To a solution of the ester of part E (600 mg, 1.02 mmol) in 1,4-dioxane (2 mL) was added 4M HCl in dioxane (5 mL) and the solution was stirred for 30 minutes. The solution was concentrated in vacuo. Reverse phase chromatography (on silica, acetonitrile/H₂O) provided the title compound as an off-white solid (400 mg, 72%). HPLC purity: 100%. MS(CI) MH⁺ calculated for C₂₄H₃₁N₃O₇S: 506, found 506. HRMS calculated for C₂₄H₃₁N₃O₇S: 506.1961, found 506.1955.

EXAMPLE 13a (S)-N-[1-[(Hydroxyamino) carbonyl]-2,2-dimethyl-3-[(4-phenoxyphenyl)sulfonyl]-propyl]-4-morpholineacetamide Monohydrochloride

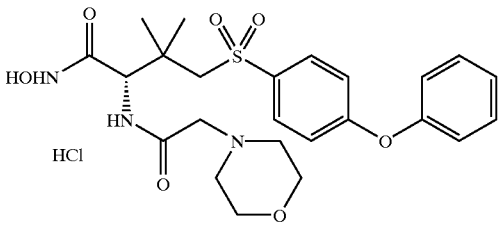

To a solution of the hydroxamate of Example 13, part F (360 mg, 0.72 mmol) in acetonitrile (10 mL) was added concentrated HCl (0.15 mL) and the solution was stirred for 10 minutes. Concentration in vacuo followed by tritration with ether provided the hydrochloride salt a pink solid (260 mg, 67%). HPLC purity: 99.6%.

EXAMPLE 14

(S)-N-[1-[(Hydroxyamino)carbonyl]-2,2-dimethyl-3-[4-phenoxy)sulfonyl]propyl]-1-pyrrolidine Acetamide Monohydrochloride

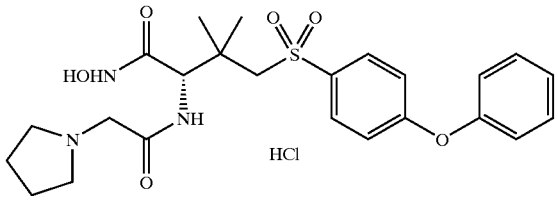

Part A: To a solution of the chloro compound of Example 13, part B (870 mg, 1.9 mmol) in THF (10 mL) and H₂O (0.5 mL) was added pyrrolidine (0.95 mL, 11.4 mmol) and the solution was stirred for 2 hours. The solution was concentrated in vacuo and the residue was dissolved into ethyl acetate. Concentration in vacuo provided the pyrrolidine compound as a white foam (930 mg, 93%)

Part B: To a solution of the pyrrolidine compound of part A (930 mg, 1.9 mmol) in THF (10 mL) was added potassium trimethylsilanolate (300 mg, 2.3 mmol) and the solution was stirred at ambient temperature for 18 hours. The solution was concentrated in vacuo to provide the potassium salt of the acid as a white foam (1.03 g, quantitative yield).

Part C: To a solution of the acid salt of part B (1.02 g, 2.0 mmol) in dichloromethane (10 mL) cooled to zero degrees Celsius was added 4-methylmorpholine (0.61 mL, 6.0 mmol), O-tetrahydropyranyl hydroxylamine (240 mg, 2.04 mmol) and PyBroP® (1.03 g, 2.2 mmol) and the solution was stirred at ambient temperature for 18 hours. The solution was concentrated in vacuo. Chromatography (on silica, ethyl acetate/THF) followed by tritration with ethyl ether provided the ester as a white foam (250 mg, 22%).

Part D: A solution of the ester of part C (250 mg, 0.44 mmol) in 4M HCl in dioxane (1 mL) and methanol (0.5 mL) was stirred for 30 minutes. The solution was concentrated in vacuo to provide the title compound as a white solid (250 mg, quantitative yield). [Data to follow on 2/26]

EXAMPLE 15

N-Hydroxy-a-[2-[(4-phenoxyphenyl) sulfonyl]-ethyl]-1-piperidineacetamide Monohydrochloride

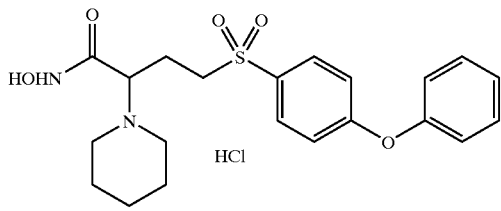

Part A: A solution of α-bromo-γ-lactone (10.13 g, 61.4 mmol) in pyridine (15.2 mL, 153 mmol) was stirred at ambient temperature for 2 days. To this solution was added dichloromethane (50 mL) followed by NaOH (2.46 g, 61.4 mmol) in $H_2O$ (20 mL). The solution was extracted with dichloromethane and washed with saturated NaCl and dried over $MgSO_4$. Vacuum distillation provided the pyridyl lactone as a yellow oil (7.093 g, 68%).

Part B: To a slurry of NaH (60% suspension in mineral oil) in DMF (44 mL) cooled to 0° C. was added 4-(phenoxy)benzenethiol (5.87 g, 29.0 mmol). After 15 minutes the pyridyl lactone of part A (3.78 g, 22.3 mmol) was added and the solution was heated to eighty-seven degrees Celsius for 16 hours. The solution was concentrated in vacuo and the residue was partitioned between 2N HCl and ethyl ether and the aqueous was extracted with ethyl ether. The aqueous layer was concentrated in vacuo and the resulting oil crystallized upon standing to provide the sulfide hydrochloride salt as a white solid (4.07 g, 45%).

Part C: To a solution of the sulfide of part B (1.206 g, 2.96 mmol) in DMF (10 mL) was added 4-methylmorpholine (1.30 mL, 11.8 g), N-hydroxybenzotriazole (480 mg, 3.55 mmol), 1-(3-dimethylaminopropyl)-3-ethylcarbodiimide hydrochloride (737 mg, 3.84 mmol) and O-tetrahydropyranyl hydroxylamine (485 g, 4.14 mmol) and the solution stirred for 18 hours at ambient temperature. The solution was concentrated in vacuo and the residue was partitioned between dichloromethane and $H_2O$. The organic layer was washed with $H_2O$ and saturated NaCl and dried over $Na_2SO_4$. Chromatography (on silica, methanol($NH_3$)/dichloromethane) provided the ester as a colorless oil (1.08 g, 77%). MS(CI) $MH^+$ calculated for $C_{26}H_{34}N_2O_4S$: 471, found 471. Analytical calculation for $C_{26}H_{34}N_2O_4S$: C, 66.35; H, 7.28; N, 5.95; S, 6.81. Found: C, 65.97; H, 7.51; N, 5.98; S, 6.91.

Part D: To a solution of the ester of part C (234 mg, 0.50 mmol) in dichloromethane (3 mL) was added p-toluenesulfonic acid (95 mg, 0.50 mmol) followed by 3-chloroperbenzoic acid (57–86%, 257 mg, 1.50 mmol) and the solution stirred for 1.5 hours at ambient temperature. The solution was diluted with dichloromethane and washed with 10% $Na_2CO_3$, saturated $NaHCO_3$, $H_2O$ and saturated NaCl and dried over $Na_2SO_4$. Chromatography (on silica, methanol($NH_3$)/dichloromethane) provided the sulfone as a colorless oil (101 mg, 40%). MS(CI) $MH^+$ calculated for $C_{26}H_{34}N_2O_6S$: 503, found 503.

Part E: To a solution of the sulfone of part D (100 mg, 0.20 mmol) in methanol (2 mL) was added acetyl chloride (0.038 mL, 0.60 mmol) and the solution was stirred for 17 hours at ambient temperature. The solution was concentrated and the residue was diluted in ethyl acetate. The resulting precipitate was washed with ethyl acetate to provide the title compound as a white solid (62 mg, 69%). MS(CI) $MH^+$ calculated for $C_{21}H_{26}N_2O_5S$: 419, found 419. Analytical calculation for $C_{21}H_{26}N_2O_5S \cdot HCl$: C, 55.44; H, 5.98; N. 6.16; Cl, 7.79. Found: C, 55.60; H, 6.24; N, 6.03; Cl, 7.65.

EXAMPLE 16

1,1-Dimethylethyl Ester 4-[(Hydroxyamino)-carbonyl]-4-[2-[(4-phenoxyphenyl)sulfonyl]-ethyl]-1-piperidinecarboxylic Acid

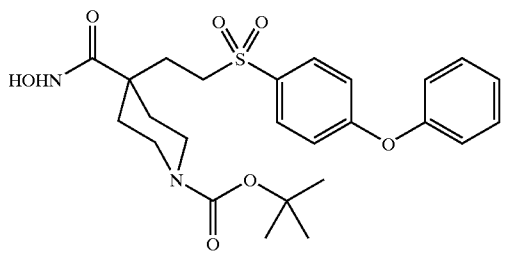

Part A: To a solution of ethyl isonipecotate (15.7 g, 0.1 mol) in tetrahydrofuran (100 mL) was added a solution of di-tert-butyl dicarbonate (21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (26.2 g, quantitative yield) as a clear, colorless oil.

Part B: To a solution of the BOC-piperidine of part A (5.14 g, 20.0 mmol) in THF (60 mL) cooled to –50° C. was added lithium diusopropyl amide (1.8 M in THF, 11.1 mL, 20.0 mmol). The solution stirred for 1 hour followed by the addition of 1-bromo-2-chloroethane (1.66 mL, 20.0 mmol). After stirring at –40° C. for 15 minutes, the solution returned to ambient temperature for 4 hours. The reaction was quenched with $H_2O$ and extracted with ethyl acetate and the organic layer was washed with $H_2O$ and satd. NaCl, and dried over $MgSO_4$. Concentration in vacuo provided the chlorinated compound as a yellow oil (5.98 g, 93%).

Part C: To a cooled (0° C.) suspension of sodium hydride (120 mg as a 60% dispersion in mineral oil, 3.0 mmol) in DMF (4 mL) was added 4-(phenoxy)benzenethiol (607 mg, 3.0 mmol) in DMF (2 mL) and the solution stirred for 15 minutes. To this solution was added the chlorinated compound of part A (960 mg, 3.0 mmol) in DMF (5 mL) and the solution stirred at ambient temperature for 4 hours. The solution was partitioned between ethyl acetate and $H_2O$ and the organic was washed with 15% $KHSO_4$ and satd. NaCl and dried over $MgSO_4$. Chromatography (1:9 ethyl acetate/hexane) provided the sulfide as an oil (1.26 g, 87%).

Part D: To a solution of the sulfide of Part C (1.25 g, 2.6 mmol) in dichloromethane (20 mL) cooled to 0° C., was added 3-chloroperbenzoic acid (80%, 1.11 g, 5.1 mmol). The solution stirred at ambient temperature for 2.5 hours. Additional dichloromethane was added and the organic layer was washed with $H_2O$, satd. $NaHCO_3$, and satd. NaCl and dried over $MgSO_4$. Chromatography (20 ethyl acetate/80 hexane) provided the sulfone as a solid (740 mg, 56%).

MS(CI) MH+ calcd. for $C_{27}H_{35}NO_7S$: 518, found 518. HRMS calcd. for $C_{27}H_{35}NO_7S$: 518.2212, found 518.2222.

Part E: To a solution of the sulfone of Part D (708 mg, 1.37 mmol) in THF (5 mL) and ethanol (5 mL) was added sodium hydroxide (547 mg, 13.7 mmol) in $H_2O$ (7 mL). The solution was heated to 65° C. for 18 hours. The solution was concentrated in vacuo and the residue was suspended in $H_2O$ and acidified with 2N HCl. The solution was extracted with ethyl acetate and the organic layer was washed with sat. NaCl and dried over $MgSO_4$. Concentration in vacuo provided the acid as a light yellow foam (500 mg, 75%). MS(CI) MH+ calcd. for $C_{25}H_{31}NO_7S$: , found. HRMS calcd. for $C_{25}H_{31}NO_7S$: , found. Anal. calcd. for $C_{25}H_{b31}NO_7S$ $0.3H_2O$: C, 60.66; H, 6.43; N, 2.83; S, 6.48. Found: C, 60.20; H, 6.59; N, 2.63; S, 5.85.

Part F: To a solution of the acid of part E (475 mg, 0.97 mmol) in DMF (10 mL) was added N-hydroxybenzotriazole·$H_2O$ (157 mg, 1.16 mmol) followed by 1-(3-dimethylaminopropyl)-3-ethylcarbodiimide hydrochloride(260 mg, 1.36 mmol). After 5 minutes of stirring at ambient temperature 4-methylmorpholine (0.32 mL, 2.91 mmol) was added followed by 50% aqueous $NH_2OH$ (0.192 mL, 2.91 mmol). The solution stirred for 7 hours. Additional N-hydroxybenzotriazole·$H_2O$ (157 mg), 1-(3-dimethylaminopropyl)-3-ethylcarbodiimide hydrochloride (260 mg), 4-methylmorpholine (0.32 mL) and 50% aqueous $NH_2OH$ were added and the solution stirred for 48 hours. The solution was diluted with $H_2O$, extracted with ethyl acetate and washed with satd. NaCl and dried over $MgSO_4$. Reverse phase HPLC (acetonitrile/$H_2O$) provided the title compound as a white solid (228 mg, 47%). HPLC purity: >99%. MS(CI) MH+ calcd. for $C_{25}H_{32}N_2O_7S$: 505, found 505. Anal. calcd. for $C_{25}H_{32}N_2O_7S·0.25H_2O$: C, 58.98; H, 6.43; N, 5.50. Found: C, 58.87; H, 6.40; N, 5.38.

EXAMPLE 17

N-Hydroxy-4-[2-[(4-phenoxyphenyl) sulfonyl]-ethyl]-4-piperidine carboxamide, Monohydrochloride

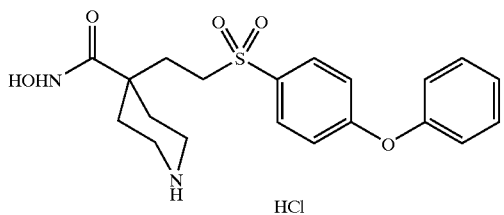

Part A: To a solution of ethyl isonipecotate (15.7 g, 0.1 mol) in tetrahydrofuran (100 mL) was added a solution of di-tert-butyl dicarbonate (21.8 g, 0.1 mol) in THF (5 mL) dropwise over 20 minutes. The solution stirred overnight at ambient temperature and concentrated in vacuo to yield a light oil. The oil was filtered through silica gel (7:3 ethyl acetate/hexane) and concentrated in vacuo to give the BOC-piperidine compound (26.2 g, quantitative yield) as a clear, colorless oil.

Part B: To a solution of the BOC-piperidine of part A (5.14 g, 20.0 mmol) in THF (60 mL) cooled to −50° C. was added lithium diisopropyl amide (1.8 M in THF, 11.1 mL, 20.0 mmol). The solution stirred for 1 hour followed by the addition of 1-bromo-2-chloroethane (1.66 mL, 20.0 mmol). After stirring at −40° C. for 15 minutes, the solution returned to ambient temperature for 4 hours. The reaction was quenched with $H_2O$ and extracted with ethyl acetate and the organic layer was washed with $H_2O$ and satd. NaCl, and dried over $MgSO_4$. Concentration in vacuo provided the chlorinated compound as a yellow oil (5.98 g, 93%).

Part C: To a cooled (0° C.) suspension of sodium hydride (120 mg as a 60% dispersion in mineral oil, 3.0 mmol) in DMF (4 mL) was added 4-(phenoxy)benzene (607 mg, 3.0 mmol) in DMF (2 mL) and the solution stirred for 15 minutes. To this solution was added the chlorinated compound of part A (960 mg, 3.0 mmol) in DMF (5 mL) and the solution stirred at ambient temperature for 4 hours. The solution was partitioned between ethyl acetate and $H_2O$ and the organic was washed with 15% $KHSO_4$ and satd. NaCl and dried over $MgSO_4$. Chromatography (1:9 ethyl acetate/hexane) provided the sulfide as an oil (1.26 g, 87%).

Part D: To a solution of the sulfide of Part C (1.25 g, 2.6 mmol) in dichloromethane (20 mL) cooled to 0° C., was added 3-chloroperbenzoic acid (80%, 1.11 g, 5.1 mmol). The solution stirred at ambient temperature for 2.5 hours. Additional dichloromethane was added and the organic layer was washed with $H_2O$, satd. $NaHCO_3$, and satd. NaCl and dried over $MgSO_4$. Chromatography (20 ethyl acetate/80 hexane) provided the sulfone as a solid (740 mg, 56%). HRMS calcd. for $C_{27}H_{35}NO_7S$: 518.2212, found 518.2222.

Part E: To a solution of the sulfone of Part D (708 mg, 1.37 mmol) in THF (5 mL) and ethanol (5 mL) was added sodium hydroxide (547 mg, 13.7 mmol) in $H_2O$ (7 mL). The solution was heated to 65° C. for 18 hours. The solution was concentrated in vacuo and the residue was suspended in $H_2O$ and acidified with 2N HCl. The solution was extracted with ethyl acetate and the organic layer was washed with satd. NaCl and dried over $MgSO_4$. Concentration in vacuo provided the acid as a light yellow foam (500 mg, 75%). Anal. calcd. for $C_{25}H_{31}NO_7S·0.3H_2O$: C, 60.64; H, 6.43; N, 2.83; S, 6.48. Found: C, 60.20; H, 6.59; N, 2.63; S, 5.85.

Part F: To a solution of the acid of part E (475 mg, 0.97 mmol) in DMF (10 mL) was added N-hydroxybenzotriazole·$H_2O$ (157 mg, 1.16 mmol) followed by 1-(3-dimethylaminopropyl)-3-ethylcarbodiimide hydrochloride (260 mg, 1.36 mmol). After 5 minutes of stirring at ambient temperature 4-methylmorpholine (0.32 mL, 2.91 mmol) was added followed by 50% aqueous $NH_2OH$ (0.192 mL, 2.91 mmol). The solution stirred for 7 hours. Additional N-hydroxybenzotriazole·$H_2O$ (157 mg), 1-(3-dimethylaminopropyl)-3-ethylcarbodiimide hydrochloride (260 mg), 4-methylmorpholine (0.32 mL) and 50% aqueous $NH_2OH$ were added and the solution stirred for 48 hours. The solution was diluted with $H_2O$, extracted with ethyl acetate and washed with satd. NaCl and dried over $MgSO_4$. Reverse phase HPLC (acetonitrile/$H_2O$) provided the hydroxamate as a white solid (228 mg, 47%). Anal. calcd. for $C_{25}H_{32}N_2O_7S·0.25H_2O$: C, 58.98; H, 6.43; N, 5.50. Found: C, 58.87; H, 6.40; N, 5.38.

Part G: To a cooled (0° C.) solution of the BOC-hydroxamate of Part F (205 mg, 0.41 mmol) was bubbled HCl gas for 5 minutes followed by standing for 1 hour. Concentration followed by trituration with ethyl ether provided the title compound as a white solid (183 mg, quantitative yield). MS (CI) MH+ calcd. for $C_{20}H_{24}N_2O_5S$: 405, found 405. HRMS calcd. for $C_{20}H_{24}N_2O_5S$: 405.1484, found 405.1484. Anal. calcd. for $C_{20}H_{24}N_2O_5S$ HCl $H_2O$: C, 52.34; H, 5.97; N, 6.10; Cl, 7.72. Found: C, 52.07; H, 5.97; N, 5.85; Cl, 8.04.

EXAMPLE 18

In Vitro Metalloprotease Inhibition

Several of the compounds prepared in the manner described in Examples 1 to 17 were assayed for activity by an in vitro assay. Following the procedures of Knight et al., *FEBS Lett.* 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM CaCl$_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 μM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The IC$_{50}$ values were calculated from those values. The results are set forth in the Inhibition Table below, reported in terms of IC$_{50}$ to three significant figures.

TABLE 37

Inhibition Table
(IC$_{50}$ values in nM)

| Example | MMP-13 | MMP-1 | MMP-2 |
|---|---|---|---|
| 1 | 1.9 | 6300 | 0.3 |
| 2 | 8.8 | >10,000 | 2.0 |
| 3 | 2600 | >10,000 | 1000 |
| 4 | 54.4 | >10,000 | 15.8 |
| 5 | 1.8 | >10,000 | 3.2 |
| 6 | 2000 | | |
| 7 | 400 | >10,000 | 120 |
| 8a | 5.0 | >10,000 | 2.2 |
| 9a | 3.0 | 7000 | 1.3 |
| 10 | 2.4 | 10,000 | 1.5 |
| 11 | <0.1 | 50 | <0.1 |
| 12 | 1.6 | 3300 | 0.3 |
| 13 | 1.4 | 770 | 0.3 |
| 13a | 1.8 | 1800 | 0.6 |
| 14 | 2.4 | >10,000 | 1.8 |
| 15 | 13.9 | >10,000 | 7.7 |

TABLE 37-continued

Inhibition Table
(IC$_{50}$ values in nM)

| Example | MMP-13 | MMP-1 | MMP-2 |
|---|---|---|---|
| 16 | 400 | >10,000 | 169 |
| 17 | 169 | >10,000 | 70 |

EXAMPLE 19

In Vivo Angiogenesis Assay

The study of angiogenesis depends on a reliable and reproducible model for the stimulation and inhibition of a neovascular response. The corneal micpocket assay provides such a model of angiogenesis in the cornea of a mouse. See, A Model of Angiogenesis in the Mouse Cornea; Kenyon, BM, et al., Investigative Ophthalmology & Visual Science, July 1996, Vol. 37, No. 8.

In this assay, uniformly sized Hydron™ pellets containing bFGF and sucralfate are prepared and surgically implanted into the stroma mouse cornea adjacent to the temporal limbus. The pellets are formed by making a suspension of 20 μL sterile saline containing 10 μg recombinant bFGF, 10 mg of sucralfate and 10 μL of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57Bl/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. an exemplary dose is 50 mg/kg bid, po. Neovascularization of the corneal stroma begins at about day three and is permitted to continue under the influence of the assayed compound until day five. At day five, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$area = \frac{(0.4 \times clock\ hours \times 3.14 \times vessel\ length\,(\text{in mm}))}{2}$$

The studied mice are thereafter compared to control mice and the difference in the area of neovascularization is recorded. A contemplated compound typically exhibits about 25 to about 75 percent inhibition, whereas the vehicle control exhibits zero percent inhibition.

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:

1. A compound or a salt thereof, wherein:

the compound corresponds in structure to Formula I:

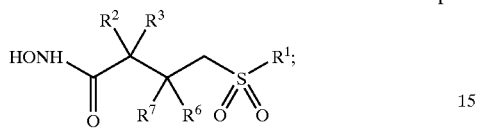

I $R^1$ is a substituted 5- or 6-membered cyclohydrocarbyl, heterocyclo, aryl, or heteroaryl;

the number of non-hydrogen atoms in the longest linear chain of atoms in $R^1$ is greater than 6 and less than about 20 atoms;

$R^1$ defines a three-dimensional volume, when rotated about an axis drawn through the $SO_2$-bonded 1-position and the 4-position of a 6-membered ring or drawn through the $SO_2$-bonded 1-position and the center of the 3,4-bond of a 5-membered ring, whose widest dimension in a direction transverse to the axis of rotation is about that of one furanyl ring to about that of two phenyl rings;

as to $R^2$ and $R^3$:

$R^1$ and $R^3$ are independently selected from the group consisting of hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl, aryl-$C_1$–$C_4$ hydrocarbyl, heteroaryl-$C_1$–$C_4$ hydrocarbyl, and benzyloxy-$C_1$–$C_4$ hydrocarbyl, except that only one of $R^2$ and $R^3$ may be other than hydrido or $C_1$–$C_4$ hydrocarbyl, or $R^2$ and $R^3$, together with the depicted carbon atom to which they are bonded, form a heterocyclic ring, wherein each heteroatom in the heterocyclic ring is: independently selected from the group consisting of oxygen, sulfur, and nitrogen, when sulfur, optionally substituted with one or two oxygens, and when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbyl sulfonyl;

as to $R^6$ and $R^7$:

$R^6$ and $R^7$ are independently selected from the group consisting of hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl, aryl-$C_1$–$C_4$ hydrocarbyl, heteroaryl-$C_1$–$C_4$ hydrocarbyl, and benzyloxy-$C_1$–$C_4$ hydrocarbyl, except that only one of $R^6$ and $R^7$ may be other than hydrido or $C_1$–$C_4$ hydrocarbyl, or $R^6$ and $R^7$, together with the depicted carbon atom to which they are bonded, form a heterocyclic ring, wherein each heteroatom in the heterocyclic ring is: independently selected from the group consisting of oxygen, sulfur, and nitrogen, when sulfur, optionally substituted with one or two oxygens, and when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl; and only one of $R^2$, $R^3$, $R^6$, and $R^7$ may be other than hydrido, $C_1$–$C_4$ hydrocarbyl, or a part of a heterocyclic ring structure.

2. The compound or salt according to claim 1, wherein:

said 5- or 6-membered cyclohydrocarbyl, heterocyclo, aryl, or heteroaryl of $R^1$ is substituted with a substituent, $R^4$; and the number of non-hydrogen atoms in the longest linear chain of atoms in $R^4$ is from 3 to about 14 atoms.

3. The compound or salt according to claim 2, wherein $R^4$ is selected from the group consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio.

4. The compound or salt according to claim 2, wherein $R^4$ is selected from the group consisting of phenyl, phenoxy, thiophenoxy, anilino, phenylazo, phenylureido, benzamido, nicotinamido, isonicotinamido, picolinamido, heterocyclo, heterocyclohydrocarbyl, arylheterocyclohydrocarbyl, arylhydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, and heteroarylthio, wherein:

any such substituent is itself substituted by one or more substituents independently selected from the group consisting of halogen, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonylhydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbylcarbonylamino, heterocyclohydrocarbyloxy, hydrocarbylsulfonylamino, arylsulfonylamino, arylhydrocarbylsulfonylamino, heteroarylsulfonylamino, heteroarylhydrocarbylsulfonylamino, cyclohydrocarbylsulfonylamino, heterocyclohydrocarbylsulfonylamino, and aminohydrocarbyl, wherein:
the aminohydrocarbyl nitrogen is substituted by one or two substituents independently selected from the group consisting of hydrocarbyl, aryl, arylhydrocarbyl, cyclohydrocarbyl, arylhydrocarbyloxycarbonyl, hydrocarbyloxycarbonyl, and hydrocarboyl, or
the aminohydrocarbyl nitrogen is substituted with two substituents such that the two substituents, together with the aminohydrocarbyl nitrogen, form a 5- to 8-membered heterocyclic or heteroaryl ring.

5. A compound or a salt thereof, wherein:
the compound corresponds in structure to Formula I:

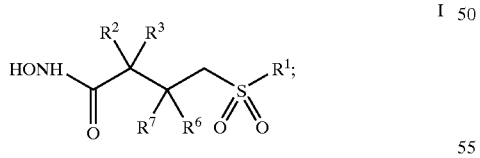

I $R^1$ is cyclohydrocarbyl, heterocyclo, aryl, or heteroaryl. wherein such substituent:
has 5 or 6 ring members, and
is substituted at its own 4-position when a 6-membered ring and at its own 3- or 4-position when a 5-membered ring with a substituent, $R^4$;
$R^4$ is selected from the group consisting of single-ringed cyclohydrocarbyl, single-ringed heterocyclo, single-ringed aryl, single-ringed heteroaryl, $C_3$–$C_{14}$ hydrocarbyl, $C_2$–$C_{14}$ hydrocarbyloxy, phenoxy, thiophenoxy group, 4-thiopyridyl, phenylazo, phenylureido, nicotinamido, isonicotinamido, picolinamido, anilino, and benzamido;

as to $R^2$ and $R^3$:
$R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
$R^2$ and $R^3$, together with the depicted carbon atom to which they are bonded, form a 6-membered heterocyclic ring, wherein each heteroatom in the heterocyclic ring is:
independently selected from the group consisting of oxygen, sulfur, and nitrogen,
when sulfur, optionally substituted with one or two oxygens, and
when nitrogen, optionally substituted with a substituent selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

as to $R^6$ and $R^7$:
$R^7$ is independently selected from the group consisting of hydrido and $C_1$–$C_4$ hydrocarbyl; and $R^6$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
$R^6$ and $R^7$, together with the depicted carbon atom to which they are bonded, form a 6-membered heterocyclic ring wherein each heteroatom in the heterocyclic ring is:
independently selected from the group consisting of oxygen, sulfur, and nitrogen,
when sulfur, optionally substituted with one or two oxygens, and
when nitrogen, optionally substituted with a substituent selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

each —Y is independently selected from the group consisting of —O— and —NR$^{11}$;
each $R^{11}$ is independently selected from the group consisting of hydrido and $C_1$–$C_4$ hydrocarbyl;
each —Z is independently selected from the group consisting of hydrido, $C_1$–$C_4$ hydrocarbyl, benzoyl, (2-pyridinyl)methyl, (3-pyridinyl)methyl, (4-pyridinyl) methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone) ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-pyridinyl, 3-pynidinyl, 4-pyndinyl, sulfonamido, $C_1$–$C_4$ hydrocarbylsulfonyl, $C_1$–$C_4$ hydrocarbylphosphonyl, and —C(O)—W;
each —W is independently selected from the group consisting of hydrido, $C_1$–$C_4$ hydrocarbyl, $C_1$–$C_4$ hydrocarbyloxy, and —CHR$^{12}$NH$_2$;
each $R^{12}$ is independently selected from the group consisting of a side chain of a D amino acid, a side chain of an L amino acid, benzyloxy, benzylamino, and amino; and only one of $R^2$, $R^3$, $R^6$, and $R^7$ may be other than hydrido, $C_1$–$C_4$ hydrocarbyl, or a part of a heterocyclic ring structure.

6. A compound or a salt thereof, wherein:
the compound corresponds in structure to Formula I:

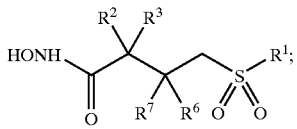

$R^1$ is phenyl substituted with $R^4$ at the 4-position; and
$R^4$ is selected from the group consisting of phenyl, phenoxy, thiophenoxy, phenylazo, benzamido, anilino, nicotinamido, isonicotinamido, picolinamido, and phenylureido, wherein any such substituent is optionally substituted:
  at the meta- or para-position or both with a substituent that is selected from the group consisting of halogen, $C_1$–$C_9$ hydrocarbyloxy, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl $C_1$–$C_4$ hydrocarbyl, $C_1$–$C_4$ hydrocarbyloxycarbonyl $C_1$–$C_4$ hydrocarbyl, and carboxamido $C_1$–$C_8$ hydrocarbyl, or
  at the meta- and para-positions by two methyl groups or by a methylenedioxy group;
as to $R^2$ and $R^3$:
  $R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^2$ and $R^3$, together with the depicted carbon atom to which they are bonded, form a 6-membered heterocyclic ring, wherein each heteroatom in the heterocyclic ring is:
    independently selected from the group consisting of oxygen, sulfur, and nitrogen,
    when sulfur, optionally substituted with one or two oxygens, and
    when nitrogen, optionally substituted with a substituent selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;
as to $R^6$ and $R^7$:
  $R^7$ is independently selected from the group consisting of hydrido and $C_1$–$C_4$ hydrocarbyl; and $R^6$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^6$ and $R^7$, together with the depicted carbon atom to which they are bonded, form a 6-membered heterocyclic ring wherein each heteroatom in the heterocyclic ring is:
    independently selected from the group consisting of oxygen, sulfur, and nitrogen,
    when sulfur, optionally substituted with one or two oxygens, and
    when nitrogen, optionally substituted with a substituent selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

each —Y is independently selected from the group consisting of —O and —$NR^{11}$;
each $R^{11}$ is independently selected from the group consisting of hydrido and $C_1$–$C_4$ hydrocarbyl;
each —Z is independently selected from the group consisting of hydrido, $C_1$–$C_4$ hydrocarbyl, benzoyl, (2-pyridinyl)methyl, (3-pyridinyl)methyl, (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone) ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-pyridinyl, 3-pyridinyl, 4-pyridinyl, sulfonamido, $C_1$–$C_4$ hydrocarbylsulfonyl, $C_1$–$C_4$ hydrocarbylphosphonyl, and —C(O)—W;
each —W is independently selected from the group consisting of hydrido, $C_1$–$C_4$ hydrocarbyl, $C_1$–$C_4$ hydrocarbyloxy, and —$CHR_{12}NH_2$;
each $R^{12}$ is independently selected from the group consisting of a side chain of a D amino acid, a side chain of an L amino acid, benzyloxy, benzylamino, and amino; and
only one of $R^2$, $R^3$, $R^6$, and $R^7$ may be other than hydrido, $C_1$–$C_4$ hydrocarbyl, or a part of a heterocyclic ring structure.

7. The compound or salt according to claim 5 wherein $R^6$ and $R^7$ are both hydrido.

8. The compound or salt according to claim 5 wherein $R^6$ and $R^7$ are both methyl.

9. The compound or salt according to claim 5, wherein the number of non-hydrogen atoms in the longest linear chain of atoms in $R^1$ is greater than 8 and less than 18 atoms.

10. A compound or a salt thereof, wherein:
the compound corresponds in structure to Formula II:

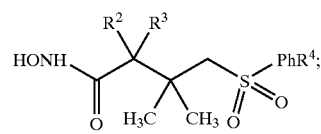

$PhR^4$ is phenyl substituted at its 4-position with $R^4$;
$R^4$ is selected from the group consisting of single-ringed aryl, single-ringed heteroaryl, $C_3$–$C_{14}$ hydrocarbyl, $C_2$–$C_{14}$ hydrocarbyloxy, phenoxy, thiophenoxy, 4-thiopyridyl, phenylazo, phenylureido, nicotinamido, isonicotinamido, picolinamido, anilino group, and benzamido;
as to $R^2$ and $R^3$:
  $R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^2$ and $R^3$, together with the depicted carbon atom to which they are bonded, form a 6-membered heterocyclic ring, wherein each heteroatom of the heterocyclic ring is:
    independently selected from the group consisting of oxygen, sulfur, and nitrogen,
    when sulfur, optionally substituted with one or two oxygens, and when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

—Y is selected from the group consisting of —O and —$NR^{11}$;

$R^{11}$ is selected from the group consisting of hydrido and $C_1$–$C_4$ hydrocarbyl;

—Z is selected from the group consisting of hydrido, $C_1$–$C_4$ hydrocarbyl, benzoyl, (2-pyridinyl)methyl, (3-pyridinyl)methyl, (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone) ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-pyridinyl, 3-pyridinyl, 4-pyridinyl, sulfonamide, $C_1$–$C_4$ hydrocarbylsulfonyl, $C_1$–$C_4$ hydrocarbylphosphonyl, and —C(O)—W;

—W is selected from the group consisting of hydrido, $C_1$–$C_4$ hydrocarbyl, $C_1$–$C_4$ hydrocarbyloxy, and —$CHR^{12}NH_2$; and $R^{12}$ is selected from the group consisting of a side chain of a D amino acid, a side chain of an L amino acid, benzyloxy, benzylamino, and amino.

11. A compound or a salt thereof, wherein:
the compound corresponds in structure to Formula II:

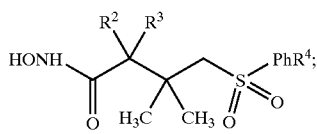

II $PhR^4$ is phenyl substituted at its 4-position with $R^4$;

$R^4$ is selected from the group consisting of phenyl, phenoxy, anilino, thiophenoxy, benzamido, nicotinamido, isonicotinamido, picolinamido, and phenylureido, wherein any such substituent is itself optionally substituted:
  at the meta or para position or both with a substituent that is selected from the group consisting of halogen, $C_1$–$C_9$ hydrocarbyloxy, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl $C_1$–$C_4$ hydrocarbyl, $C_1$–$C_4$ hydrocarbyloxycarbonyl $C_1$–$C_4$ hydrocarbyl, and carboxamido $C_1$–$C_8$ hydrocarbyl;
  at the meta- and para-positions by two methyl groups or by a $C_1$–$C_2$ alkylenedioxy group;

as to $R^2$ and $R^3$:
  $R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^2$ and $R^3$, together with the depicted carbon atom to which they are bonded, form a 6-membered heterocyclic ring, wherein each heteroatom of the heterocyclic ring is:
    independently selected from the group consisting of oxygen, sulfur, and nitrogen,
    when sulfur, optionally substituted with one or two oxygens, and
    when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

—Y is selected from the group consisting of —O and —$NR^{11}$;

$R^{11}$ is selected from the group consisting of hydrido and $C_1$–$C_4$ hydrocarbyl;

—Z is selected from the group consisting of hydrido, $C_1$–$C_4$ hydrocarbyl, benzoyl, (2-pyridinyl)methyl, (3-pyridinyl)methyl, (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone) ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl)amino]ethyl, carboxy $C_1$–$C_4$ hydrocarbyl, piperidinyl, 2-pyridinyl, 3-pyridinyl, 4-pyridinyl, sulfonamide, $C_1$–$C_4$ hydrocarbylsulfonyl, $C_1$–$C_4$ hydrocarbylphosphonyl, and —C(O)—W;

—W is selected from the group consisting of hydrido, $C_1$–$C_4$ hydrocarbyl, $C_1$–$C_4$ hydrocarbyloxy, and —$CHR^{12}NH_2$; and $R^{12}$ is selected from the group consisting of a side chain of a D amino acid, a side chain of an L amino acid, benzyloxy, benzylamino, and amino.

12. The compound or salt according to claim 11, wherein $R^4$ is unsubstituted phenoxy or thiophenoxy.

13. The compound or salt according to claim 10, wherein the compound corresponds in stereoconfiguration to Formula IIA:

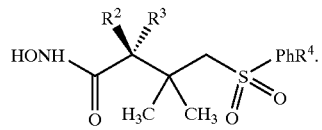

IIA

14. The compound or salt according to claim 10, wherein: the compound corresponds in structure to Formula III:

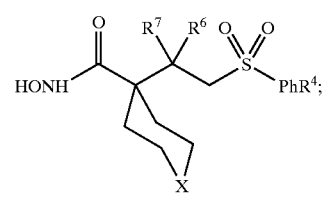

III

X is selected from the group consisting of O, S, S(O), $S(O_2)$, and $NR^5$;

$R^5$ is selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl; and $R^6$ and $R^7$ are independently selected from the group consisting of hydrido and methyl.

15. The compound or salt according to claim 10 wherein $PhR^4$ is 4-phenoxyphenyl.

16. The compound or salt according to claim 15, wherein the compound corresponds in structure to Formula V:

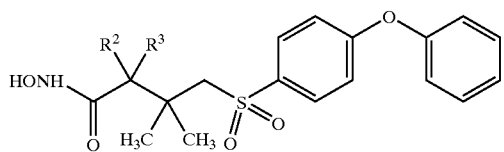

V

17. The compound or salt according to claim 16, wherein the compound corresponds in stereoconfiguration to Formula VA:

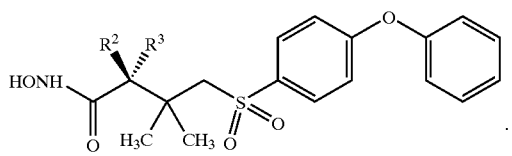

VA

18. The compound or salt according to claim 17, wherein the compound corresponds in structure to Formula VI:

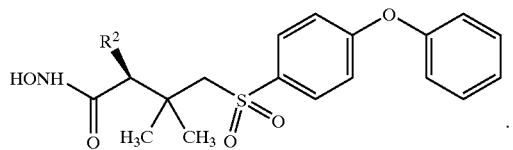

VI

19. A compound or a salt thereof, wherein:
the compound corresponds in structure to Formula VII:

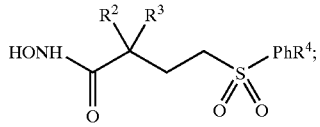

VII $PhR^4$ is phenyl substituted at its 4-position with $R^4$;
$R^4$ is selected from the group consisting of single-ringed aryl, single-ringed heteroaryl, $C_3$–$C_{14}$ hydrocarbyl, $C_2$–$C_{14}$ hydrocarbyloxy, phenoxy, thiophenoxy, 4-thiopyridyl, phenylazo, phenylureido, nicotinamido, isonicotinamido, picolinamido, anilino, and benzamido;
as to $R^2$ and $R^3$:
  $R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^2$ and $R^3$, together with the depicted carbon atom to which they are bonded, form a 6-membered heterocyclic ring, wherein each heteroatom in the heterocyclic ring is:
    independently selected from the group consisting of oxygen, sulfur, and nitrogen,
    when sulfur, optionally substituted with one or two oxygens, and
    when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl;

—Y is selected from the group consisting of —O— and —$NR^{11}$;

$R^{11}$ is selected from the group consisting of hydrido and $C_1$–$C_4$ hydrocarbyl;

—Z is selected from the group consisting of hydrido, $C_1$–$C_4$ hydrocarbyl, benzoyl, (2-pyridinyl)methyl, (3-pyridinyl)methyl, (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone)ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl]amino)ethyl, carboxy $C_1$–$C_4$ hydrocarbyl, piperidinyl, 2-pyridinyl, 3-pyridinyl, 4-pyridinyl, sulfonamido, $C_1$–$C_4$ hydrocarbylsulfonyl, $C_1$–$C_4$ hydrocarbylphosphonyl and —C(O)—W;

—W is selected from the group consisting of hydrido, $C_1$–$C_4$ hydrocarbyl, $C_1$–$C_4$ hydrocarbyloxy, and —$CHR^{12}NH_2$; and $R^{12}$ is selected from the group consisting of a side chain of a D amino acid, a side chain of an L amino acid, benzyloxy, benzylamino, and amino.

20. A compound or a salt thereof, wherein:
the compound corresponds in structure to Formula VII:

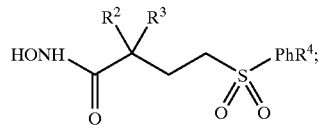

VII $PhR^4$ is phenyl substituted at its 4-position with $R^4$;
$R^4$ is selected from the group consisting of phenyl, phenoxy, anilino, thiophenoxy, benzamido, nicotinamido, isonicotinamido, picolinamido, and phenylureido, wherein any such substituent is itself optionally substituted:
  at the meta or para position or both with a substituent that is selected from the group consisting of halogen, $C_1$–$C_9$ hydrocarbyloxy, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl $C_1$–$C_4$ hydrocarbyl, $C_1$–$C_4$ hydrocarbyloxycarbonyl $C_1$–$C_4$ hydrocarbyl, and carboxamido $C_1$–$C_8$ hydrocarbyl group, or
  at the meta- and para-positions by two methyl groups or by a $C_1$–$C_2$ alkylenedioxy group;
as to $R^2$ and $R^3$:
  $R^3$ is selected from the group consisting of hydrido and $C_1$–$C_4$ hydrocarbyl; and $R^2$ is selected from the group consisting of hydrido, $C_1$–$C_4$ hydrocarbyl, N-piperidinyl, N-piperazinyl, N-($C_1$–$C_4$ hydrocarbyl)piperazinyl, N-pyrrolidinyl, N-morpholinyl, and —Y—Z, or
  $R^2$ and $R^3$, together with the depicted carbon atom to which they are bonded, form a 6-membered heterocyclic ring, wherein each heteroatom in the heterocyclic ring is:
    independently selected from the group consisting of oxygen, sulfur, and nitrogen,
    when sulfur, optionally substituted with one or two oxygens, and when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ carbonylhydrocarbyl, and sulfonyl $C_1$–$C_4$ hydrocarbyl;

—Y is selected from the group consisting of —O and —$NR^{11}$;

$R^{11}$ is selected from the group consisting of hydrido and $C_1$–$C_4$ hydrocarbyl;

—Z is selected from the group consisting of hydrido, $C_1$–$C_4$ hydrocarbyl, benzoyl, (2-pyridinyl)methyl, (3-pyridinyl)methyl, (4-pyridinyl)methyl, 2-(morpholinyl)ethyl, 2-(piperidinyl)ethyl, 2-(piperazinyl)ethyl, 2-(N-methylpiperazinyl)ethyl, 2-(thiomorpholinyl)ethyl, 2-(thiomorpholinyl sulfone)ethyl, 2-(succinimidyl)ethyl, 2-(hydantoinyl), 2-(3-methylhydantoinyl)ethyl, 2-(N-$C_1$–$C_4$ hydrocarbylamino)ethyl, 2-[N,N-di($C_1$–$C_4$ hydrocarbyl]amino)ethyl, carboxy $C_1$–$C_4$ hydrocarbyl, piperidinyl, 2-pyridinyl, 3-pyridinyl, 4-pyridinyl, sulfonamido, $C_1$–$C_4$ hydrocarbylsulfonyl, $C_1$–$C_4$ hydrocarbylphosphonyl and —C(O)—W;

—W is selected from the group consisting of hydrido, $C_1$–$C_4$ hydrocarbyl, $C_1$–$C_4$ hydrocarbyloxy, and —$CHR^{12}NH_2$; and $R^{12}$ is selected from the group consisting of a side chain of a D amino acid, a side chain of an L amino acid, benzyloxy, benzylamino, and amino.

21. The compound or salt according to claim 20, wherein $R^4$ is unsubstituted phenoxy or thiophenoxy.

22. The compound or salt according to claim 19, wherein the compound corresponds in stereoconfiguration to Formula VIIA:

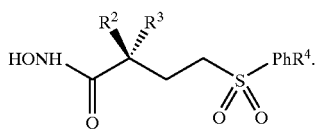

VIIA

23. The compound or salt according to claim 19, wherein:

the compound corresponds in structure to Formula VIII:

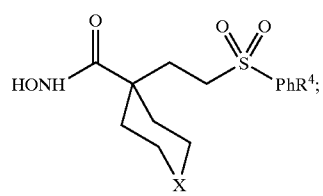

VIII

X is selected from the group consisting of O, S, S(O), S(O), and $NR^5$; and $R^5$ is selected from the group consisting of $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl.

24. The compound or salt according to claim 23, wherein the compound corresponds in structure to Formula IX:

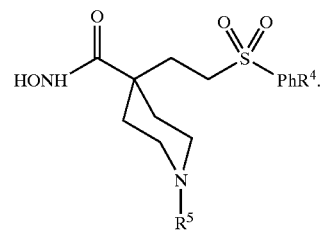

IX

25. A compound or a salt thereof, wherein the compound corresponds in structure to the following formula:

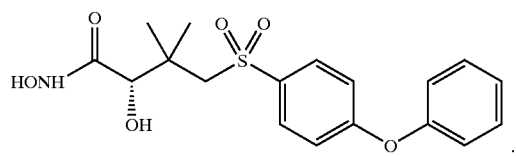

26. A compound or a salt thereof, wherein the compound corresponds in structure to the following formula:

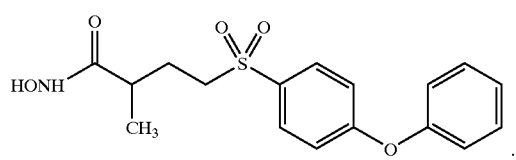

27. A compound or a salt thereof, wherein the compound corresponds in structure to the following formula:

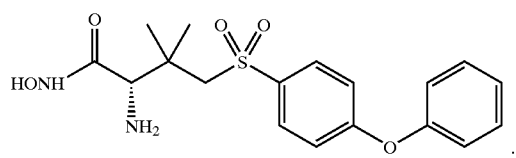

28. A process for treating a host mammal having a condition associated with pathological matrix metalloprotease activity, wherein:

the process comprises administering a compound or a salt thereof in an MMP enzyme-inhibiting effective amount to a mammalian host having such a condition;

the compound corresponds in structure to Formula I:

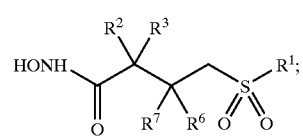

I $R^1$ is a substituted 5- or 6-membered cyclohydrocarbyl, heterocyclo, aryl, or heteroaryl;

the number of non-hydrogen atoms in the longest linear chain of atoms in $R^1$ is greater than 6 and less than about 20 atoms;

$R^1$ defines a three-dimensional volume, when rotated about an axis drawn through the $SO_2$-bonded 1-position and the 4-position of a 6-membered ring or drawn through the $SO_2$-bonded 1-position and the center of the 3,4-bond of a 5-membered ring, whose widest dimension in a direction transverse to the axis of rotation is about that of one furanyl ring to about that of two phenyl rings;

as to $R^2$ and $R^3$:

$R^2$ and $R^3$ are independently selected from the group consisting of hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamino-$C_1$–$C_4$ hydrocarbyl, aryl-$C_1$–$C_4$ hydrocarbyl, heteroaryl-$C_1$–$C_4$ hydrocarbyl, and benzyloxy-$C_1$–$C_4$ hydrocarbyl, except that only one of $R^2$ and $R^3$ may be other than hydrido or $C_1$–$C_4$ hydrocarbyl, or $R^2$ and $R^3$, together with the depicted carbon atom to which they are bonded, form a heterocyclic ring, wherein each heteroatom in the heterocyclic ring is:
  independently selected from the group consisting of oxygen, sulfur, and nitrogen,
  when sulfur, optionally substituted with one or two oxygens, and
  when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl;

as to $R^6$ and $R^7$:

$R^6$ and $R^7$ are independently selected from the group consisting of hydrido, $C_1$–$C_4$ hydrocarbyl, heteroaryl-$C_1$–$C_4$ hydrocarbyl, aryl-$C_1$–$C_4$ hydrocarbyl, hydroxy-$C_1$–$C_4$ hydrocarbyl, $C_1$–$C_4$ hydrocarbyloxy-$C_1$–$C_4$ hydrocarbyl, aryloxy-$C_1$–$C_4$ hydrocarbyl, amino-$C_1$–$C_4$ hydrocarbyl, $C_1$–$C_4$ hydrocarbylthio-$C_1$–$C_4$ hydrocarbyl, $C_1$–$C_4$ hydrocarbylsulfonyl-$C_1$–$C_4$ hydrocarbyl, aminosulfonylamino-$C_1$–$C_4$ hydrocarbyl, aminocarbonylamino-$C_1$–$C_4$ hydrocarbyl, $C_1$–$C_4$ hydrocarbylcarbonylamhio-$C_1$–$C_4$ hydrocarbyl, aryl-$C_1$–$C_4$ hydrocarbyl, heteroaryl-$C_1$–$C_4$ hydrocarbyl, and benzyloxy-$C_1$–$C_4$ hydrocarbyl, except that only one of $R^6$ and $R^7$ may be other than hydrido or $C_1$–$C_4$ hydrocarbyl, or $R^6$ and $R^7$, together with the depicted carbon atom to which they are bonded, form a heterocyclic ring, wherein each heteroatom in the heterocyclic ring is:
  independently selected from the group consisting of oxygen, sulfur, and nitrogen,
  when sulfur, optionally substituted with one or two oxygens, and
  when nitrogen, optionally substituted with a substituent, $R^5$, that is selected from the group consisting of hydrido, $C_1$–$C_4$ hydrocarbyl, $C_3$–$C_6$ cyclohydrocarbyl, $C_1$–$C_4$ hydrocarbylcarbonyl, and $C_1$–$C_4$ hydrocarbylsulfonyl; and only one of $R^2$, $R^3$, $R^6$, and $R^7$ may be other than hydrido, $C_1$–$C_4$ hydrocarbyl, or a part of a heterocyclic ring structure.

29. The process according to claim 28, wherein $R^1$ is single-ringed cyclohydrocarbyl, single-ringed heterocyclo, single-ringed aryl, single-ringed heteroaryl, wherein any such substituent is:

5- or 6-membered, and substituted at its own 4-position when a 6-membered ring and at its own 3- or 4-position when a 5-membered ring with $R^4$; and $R^4$ is selected from the group consisting of single-ringed aryl, single-ringed heteroaryl, $C_3$–$C_{14}$ hydrocarbyl, $C_2$–$C_{14}$ hydrocarbyloxy, phenoxy, thiophenoxy, anilino, 4-thiopyridyl, phenylazo, phenylureido, nicotinamido, isonicotinamido, picolinamido, and benzamido.

30. The process according to claim 28, wherein:

$R^1$ is phenyl substituted with $R^4$ at the 4-position; and $R^4$ is selected from the group consisting of phenyl, phenoxy, anilino, thiophenoxy, phenylazo, benzamido, nicotinamido, isonicotinamido, picolinamido, and phenylureido.

31. The process according to claim 28, wherein:

$R^1$ is phenyl substituted with $R^4$ at the 4-position, and $R^4$ is phenyl, phenoxy, anilino, thiophenoxy, phenylazo, benzamido, nicotinamido, isonicotinamido, picolinamido, and phenylureido, wherein any such substituent is substituted:

at the meta- or para-position or both with a substituent that is selected from the group consisting of halogen, $C_1$–$C_9$ hydrocarbyloxy, $C_1$–$C_{10}$ hydrocarbyl, di-$C_1$–$C_9$ hydrocarbylamino, carboxyl $C_1$–$C_8$ hydrocarbyl, $C_1$–$C_4$ hydrocarbyloxy carbonyl $C_1$–$C_4$ hydrocarbyl, $C_1$–$C_4$ hydrocarbyloxycarbonyl $C_1$–$C_4$ hydrocarbyl, and carboxamido $C_1$–$C_8$ hydrocarbyl, or at the meta- and para-positions by two methyl groups or by a methylenedioxy group.

32. The process according to claim 28, wherein the number of non-hydrogen atoms in the longest linear chain of atoms in $R^1$ is greater than 8 and less than 18 atoms.

33. The process according to claim 30, wherein $R^4$ is unsubstituted phenoxy or thiophenoxy.

34. The process according to claim 28, wherein said compound or salt is administered a plurality of times.

35. The compound or salt according to claim 18, wherein the compound corresponds in structure to the following formula:

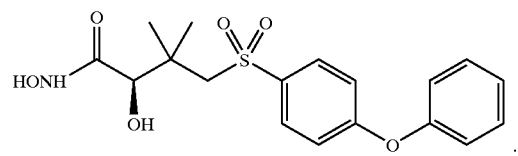

36. The compound or salt according to claim 21, wherein the compound corresponds in structure to the following formula:

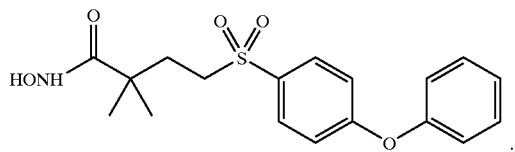

37. The compound or salt according to claim 21, wherein the compound corresponds in structure to the following formula:

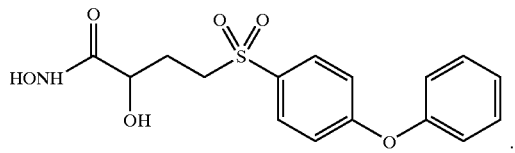

38. The compound or salt according to claim 21, wherein the compound corresponds in structure to the following formula:

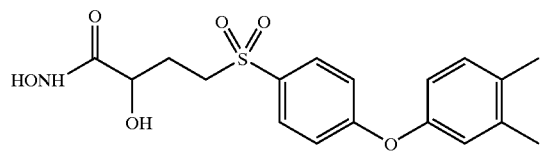

39. The compound or salt according to claim 18, wherein the compound corresponds in structure to the following formula:

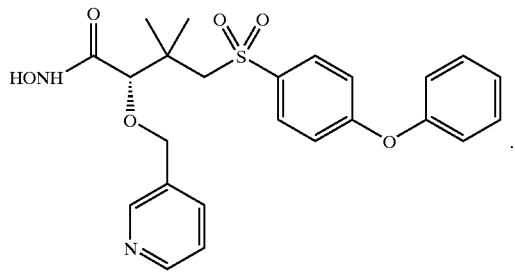

40. The compound or salt according to claim 18, wherein the compound corresponds in structure to the following formula:

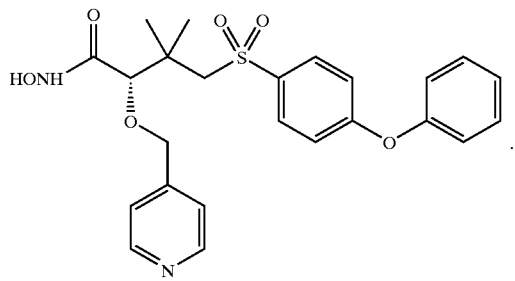

41. The compound or salt according to claim 18, wherein the compound corresponds in structure to the following formula:

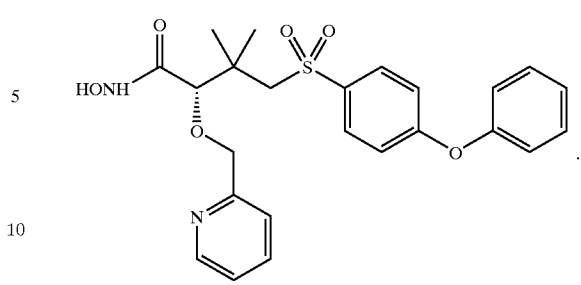

42. The compound or salt according to claim 18, wherein the compound corresponds in structure to the following formula:

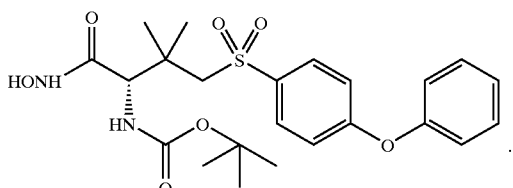

43. A compound or a salt thereof, wherein the compound corresponds in structure to the following formula:

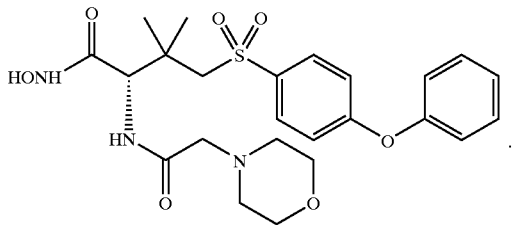

44. A compound or a salt thereof, wherein the compound corresponds in structure to the following formula:

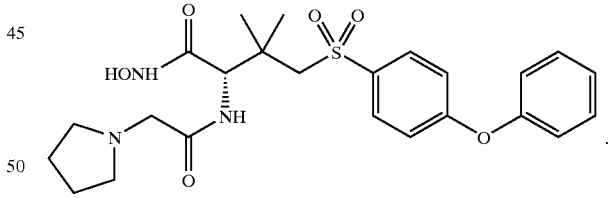

45. The compound or salt according to claim 21, wherein the compound corresponds in structure to the following formula:

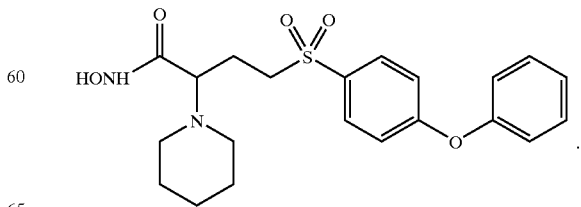

46. A compound or a salt thereof, wherein the compound corresponds in structure to the following formula:
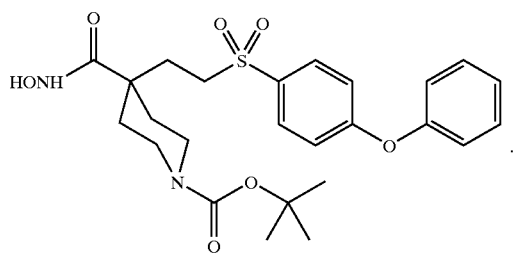
47. The compound or salt according to claim 24, wherein the compound corresponds in structure to the following formula:
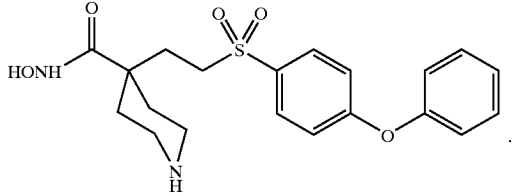
* * * * *